(12) United States Patent
Mizutani et al.

(10) Patent No.: US 8,163,770 B2
(45) Date of Patent: Apr. 24, 2012

(54) BENZOXATHIIN DERIVATIVE

(75) Inventors: Takashi Mizutani, Moriya (JP); Nagaaki Sato, Tsukuba (JP); Takahide Sasaki, Tsukuba (JP); Toshiyuki Takahashi, Tsukuba (JP)

(73) Assignee: MSD. K. K., Chiyoda-Ku (JP)

( * ) Notice: Subject to any disclaimer, the term of this patent is extended or adjusted under 35 U.S.C. 154(b) by 387 days.

(21) Appl. No.: 12/084,017

(22) PCT Filed: Oct. 25, 2006

(86) PCT No.: PCT/JP2006/321813
§ 371 (c)(1),
(2), (4) Date: Apr. 23, 2008

(87) PCT Pub. No.: WO2007/049798
PCT Pub. Date: May 3, 2007

(65) Prior Publication Data
US 2010/0168156 A1    Jul. 1, 2010

(30) Foreign Application Priority Data
Oct. 27, 2005    (JP) ................................. 2005-312956

(51) Int. Cl.
C07D 513/02    (2006.01)
C07D 515/02    (2006.01)
C07D 211/22    (2006.01)
C07D 327/06    (2006.01)
A01N 43/42    (2006.01)
A01N 43/40    (2006.01)
A61K 31/44    (2006.01)
A61K 31/445    (2006.01)

(52) U.S. Cl. ........ 514/301; 514/321; 514/338; 514/434; 546/114; 546/197; 546/276.4; 549/15

(58) Field of Classification Search .................. None
See application file for complete search history.

(56) References Cited

U.S. PATENT DOCUMENTS

| | | | |
|---|---|---|---|
| 6,750,213 B2 | 6/2004 | DiNinno et al. | |
| 2002/0165226 A1 | 11/2002 | DiNinno et al. | |
| 2003/0225132 A1* | 12/2003 | DiNinno et al. | 514/321 |
| 2004/0044226 A1* | 3/2004 | DiNinno et al. | 549/23 |
| 2005/0234245 A1 | 10/2005 | DiNinno et al. | |

FOREIGN PATENT DOCUMENTS

WO    WO 02/32373    * 4/2002

OTHER PUBLICATIONS

Kim et al. Bioorg. Med. Chem. Lett. 14(2004), 2741-2745.*

Schaefer et al. Failure is not an option: learning from unsuccessful proof-of-concept trials. Drug Discovery Today, 2008, 13(21/22), pp. 913-916.*

Horig et al. Review: From bench to clinic and back: Perspective on the 1st IQPC Translational Research Conference. Journal of Translational Medicine, 2004, 2(44).*

Burger's Medicinal Chemistry and Drug Discovery, Fifth Edition, vol. I: Principles and Practice, Wiley-Interscience, 1995, pp. 783-802.*

Williams et al. (Foye's Principles of Medicinal Chemistry, 5th Edition, pp. 50 and 59-61, 2002).*

H. Y. Chen, et al., "Estrogen receptor ligands. Part 3: the SAR of dihydrobenzoxathiin SERMs" Bioorganic & Medicinal Chemistry Letters, vol. 14, No. 10, pp. 2551-2554, 2004.

S. Kim, et al., "Estrogen receptor ligands. II. Discovery of Benzoxathiin as Potent, Selective Estrogen Receptor alpha Modulators", Journal of Medicinal Chemistry, vol. 47, No. 9, pp. 2171-2175, 2004.

Kim, et al.,"Estrogen receptor ligands. Part 4: The SAR of the syn-dihydrobenzoxathiin SERAMs", Bioorganic & Medicinal Chemistry Letters, vol. 14, No. 11, pp. 2741-2745, 2004.

* cited by examiner

*Primary Examiner* — Brandon Fetterolf
*Assistant Examiner* — Anna Pagonakis
(74) *Attorney, Agent, or Firm* — J. Eric Thies; Gerard M. Devlin

(57) ABSTRACT

Disclosed is a compound represented by the formula (I) below and a pharmaceutically acceptable salt thereof.

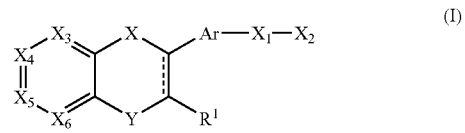

This compound is useful for treatment of obesity, diabetes and the like. [In the formula (I), Ar represents a benzene ring or the like; $X_1$ represents a nitrogen atom, a sulfur atom or the like; R1 represents an aryl group or the like; $X_2$ represents a group represented by the following formula (II): (wherein $R^4$ and $R^5$ respectively represent a lower alkyl group or the like, and m represents a number of 2-4) or the like; one of X and Y represents an oxygen atom and the other represents a sulfanyl group or the like; and $X_3$-$X_6$ respectively represent —CH—, a nitrogen atom or the like.

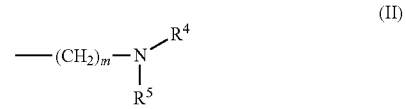

13 Claims, No Drawings

BENZOXATHIIN DERIVATIVE

CROSS REFERENCE TO RELATED APPLICATIONS

This application is a U.S. National Phase application under 35 U.S.C. §371 of PCT Application No. PCT/JP2006/321813, filed Oct. 25, 2006, which claims priority under 35 U.S.C. §119 from JP Application No. JP2005-312956, filed Oct. 27, 2005.

TECHNICAL FIELD

The present invention relates to a novel benzoxathiin derivative.

BACKGROUND ART

It has been known that, in organisms such as typically mammals, histamine that is a physiologically-active endogenous factor functions as a neurotransmitter and has extensive pharmacological activities (Life Science, Vol. 17, p. 503 (1975)).

Immunohistochemical studies have made it clear that a histamine-agonistic (producing) cell body exists in the nodal papillary nucleus in a posterior hypothalamic region and that histamine nerve fibers project in an extremely broad range in a brain, which supports various pharmacological effects of histamine (Journal of Comprehensive Neurology, Vol. 273, p. 283). The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (Progress in Neurobiology, Vol. 63, p. 637 (2001)).

The existence of the projection to the brain region that relates to vigilance sustenance, for example, to cerebral cortex suggests the role in control of vigilance or vigilance-sleep cycle. The existence of the projection to many peripheral structures such as hippocampus and amygdaloid complex suggests the role in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, a histamine-H3 receptor, has been shown by various pharmacological and physiological studies (Trends in Pharmacological Science, Vol. 8, p. 24 (1987)). Recently, human and rodent histamine-H3 receptor genes have been identified and their existence has been revealed (Molecular Pharmacology, Vol. 55, p. 1101 (1999)).

It is shown that the histamine-H3 receptor exists in the presynaptic membrane of central or peripheral neurocytes and functions as a self-receptor, therefore controlling the release of histamine and controlling even the release of other neurotransmitters. Specifically, it is reported that a histamine-H3 receptor agonist, or its antagonist or inverse-agonist controls the release of histamine, noradrenaline, serotonin, acetylcholine or dopamine from nerve ending. For example, the release of these neurotransmitters is inhibited by an agonist such as (R)-(α)-methylhistamine, and is promoted by an antagonist or inverse-agonist such as thioperamide (Trends in Pharmacological Science, Vol. 19, p. 177 (1998)).

A compound having a benzoxathiin skeleton is described, for example, in WO02/32377 or WO03/091239; however, the compounds described in these specifications differ from the invention in that a hydroxyl group is indispensable at the 6-position of benzoxathiin in the former, and in addition, these specifications do not have disclose the H3 receptor. Further, a benzoxathiin skeleton compound acting as a histamine H3 receptor antagonist or inverse-agonist is not known at all.

DISCLOSURE OF THE INVENTION

An object of the invention is to provide a novel substance having a histamine-H3 receptor antagonistic effect (an effect of inhibiting histamine from binding to a histamine-H3 receptor) or inverse-agonistic effect (an effect of inhibiting the homeostatic activity that a histamine-H3 receptor has), or that is, a novel substance that acts as a histamine-H3 receptor antagonist or inverse-agonist in living bodies.

To attain the above object, the present inventors provide the following compound or salt.

(1) A compound of a formula (I) or a pharmaceutically-acceptable salt thereof:

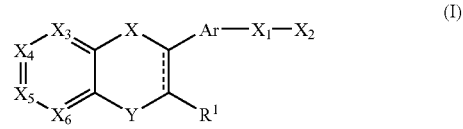

(I)

[wherein, $R^1$ represents a hydrogen atom, a lower alkyl group (the lower alkyl group may be substituted with a lower alkoxy group or a halogen atom), a lower alkoxy group (the lower alkoxy group may be substituted with a halogen atom), an aryl group (the aryl group may be substituted with a lower alkyl group (the lower alkyl group may be substituted with a halogen atom), a lower alkoxy group (the lower alkoxy group may be substituted with a halogen atom) or a halogen atom), or a heteroaryl group (the heteroaryl group may be substituted with a lower alkyl group (the lower alkyl group may be substituted with a halogen atom), a lower alkoxy group (the lower alkoxy group may be substituted with a halogen atom), or a halogen atom);

$R^2$ each independently represents a hydrogen atom, an amino group, an alkylamino group, a dialkylamino group, a nitro group, a cyano group, a hydroxyl group, a lower alkylsulfonyl group, a halogen atom, a lower alkyl group (the lower alkyl group may be substituted with a halogen atom), a cycloalkyl group (the cycloalkyl group may be substituted with a lower alkyl group or a halogen atom), a lower alkoxy group (the lower alkoxy group may be substituted with a halogen atom), a cycloalkoxy group, an aryloxy group, an aralkyloxy group, a heteroaryloxy group, a heteroarylalkyloxy group, an aryl group, a heteroaryl group, an arylcarbamoyl group, a heteroarylcarbamoyl group, an aralkylcarbamoyl group, a heteroarylalkylcarbamoyl group, a mono or di-lower alkylcarbamoyl group, an aryloxycarbonylamino group, an aralkyloxycarbonylamino group, a lower alkoxycarbonylamino group, an alkanoylamino group, an arylcarbonylamino group, a heteroarylcarbonylamino group, an aralkylcarbonylamino group, a heteroarylalkylcarbonylamino group, an alkanoyl group, an arylcarbonyl group, an aralkylcarbonyl group, a formyl group, an alkylthio group, an alkylsulfonylamino group, an arylsulfonylamino group, a mono or di-lower alkylsulfamoyl group, an arylsulfamoyl group, or an aralkyl group;

one of X and Y is an oxygen atom, and the other is a sulfanyl group, a sulfinyl group or a sulfonyl group;

Ar represents a divalent group derived from a benzene ring, a pyridine ring, a pyrimidine ring, a pyrazine ring or a pyridazine ring by removing two hydrogen atoms therefrom (the divalent group may be substituted with a halogen atom, a lower alkoxy group (the lower alkoxy group may be substituted with a halogen atom), a lower alkyl group (the lower alkyl group may be substituted with a halogen atom), or a hydroxyl group);

$X_1$ represents a carbon atom, a nitrogen atom, a sulfur atom or an oxygen atom;

$X_2$ represents a group of a formula (II):

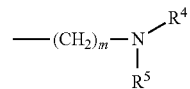

(II)

(wherein $R^4$ and $R^5$ are the same or different, each representing a lower alkyl group (the lower alkyl group may be substituted with a halogen atom), or a cycloalkyl group (the cycloalkyl group may be substituted with a lower alkyl group or a halogen atom), or $R^4$, $R^5$ and the nitrogen atom to which they bond, taken together, form a 4- to 9-membered monocyclic ring or a 4- to 8-membered bicyclic ring (the monocyclic ring or the bicyclic ring may be substituted with a lower alkyl group (the lower alkyl group may be substituted with the same or different halogen atoms), a halogen atom, a hydroxyl group or an oxo group; and the monocyclic ring may have, in the ring, still another hetero atom selected from a nitrogen atom, a sulfur atom and an oxygen atom, in addition to the nitrogen atom to which $R^4$ and $R^5$ bond), m indicates from 2 to 4); a group of a formula (III):

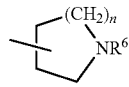

(III)

(wherein $R^6$ represents a lower alkyl group (the lower alkyl group may be substituted with a halogen atom), or a cycloalkyl group (the cycloalkyl group may be substituted with a lower alkyl group or a halogen atom), n indicates from 0 to 4), or a group of a formula (IV):

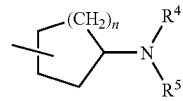

(IV)

(wherein the symbols are the same as above);

$X_3$ to $X_6$ each independently represent —$CR^2$— or a nitrogen atom; provided that 3 or more of $X_3$ to $X_6$ are not nitrogen atoms at the same time;

the formula (V):

═════ (V)

indicates a single bond or a double bond].

(2) The compound of (1) or the pharmaceutically-acceptable salt thereof, wherein $R^2$ each independently represents a hydrogen atom, a lower alkyl group (the lower alkyl group may be substituted with a halogen atom), a lower alkoxy group (the lower alkoxy group may be substituted with a halogen atom), or a halogen atom.

(3) A compound of a formula (I-1) or a pharmaceutically-acceptable salt thereof:

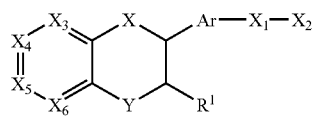

(I-1)

[wherein,
$R^1$ represents a hydrogen atom, a lower alkyl group (the lower alkyl group may be substituted with a lower alkoxy group or a halogen atom), a lower alkoxy group (the lower alkoxy group may be substituted with a halogen atom), an aryl group (the aryl group may be substituted with a lower alkyl group (the lower alkyl group may be substituted with a halogen atom), a lower alkoxy group (the lower alkoxy group may be substituted with a halogen atom) or a halogen atom), or a heteroaryl group (the heteroaryl group may be substituted with a lower alkyl group (the lower alkyl group may be substituted with a halogen atom), a lower alkoxy group (the lower alkoxy group may be substituted with a halogen atom), or a halogen atom);

$R^2$ each independently represents a hydrogen atom, a lower alkyl group (the lower alkyl group may be substituted with a halogen atom), a lower alkoxy group (the lower alkoxy group may be substituted with a halogen atom), or a halogen atom;

one of X and Y is an oxygen atom, and the other is a sulfanyl group, a sulfinyl group or a sulfonyl group;

Ar represents a divalent group derived from a benzene ring, a pyridine ring, a pyrimidine ring, a pyrazine ring or a pyridazine ring by removing two hydrogen atoms therefrom (the divalent group may be substituted with a halogen atom, a lower alkoxy group (the lower alkoxy group may be substituted with a halogen atom), a lower alkyl group (the lower alkyl group may be substituted with a halogen atom), or a hydroxyl group);

$X_1$ represents a carbon atom, a nitrogen atom, a sulfur atom or an oxygen atom;

$X_2$ represents a group of a formula (II):

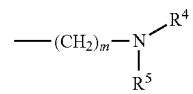

(II)

(wherein $R^4$ and $R^5$ are the same or different, each representing a lower alkyl group (the lower alkyl group may be substituted with a halogen atom), or a cycloalkyl group (the cycloalkyl group may be substituted with a lower alkyl group or a halogen atom), or $R^4$, $R^5$ and the nitrogen atom to which they bond, taken together, form a 4- to 9-membered monocyclic ring or a 4- to 8-membered bicyclic ring (the monocyclic ring or the bicyclic ring may be substituted with a lower alkyl group (the lower alkyl group may be substituted with a halogen atom), a halogen atom, a hydroxyl group or an oxo group; and the monocyclic ring may have, in the ring, still another hetero atom selected from a nitrogen atom, a sulfur atom and an oxygen atom, in addition to the nitrogen atom to which $R^4$ and $R^5$ bond), m indicates from 2 to 4);

a group of a formula (III):

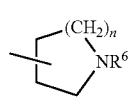

(III)

(wherein $R^6$ represents a lower alkyl group (the lower alkyl group may be substituted with a halogen atom), or a cycloalkyl group (the cycloalkyl group may be substituted with a lower alkyl group or a halogen atom), n indicates from 0 to 4), or a group of a formula (IV):

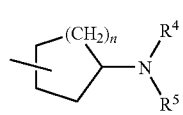

(IV)

(wherein the symbols are the same as above);

$X_3$ to $X_6$ each independently represent —$CR^2$— or a nitrogen atom; provided that 3 or more of $X_3$ to $X_6$ are not nitrogen atoms at the same time].

(4) The compound of (3) or the pharmaceutically-acceptable salt thereof, wherein $X_3$ to $X_6$ are all —$CR^2$—.

(5) The compound of (3) or the pharmaceutically-acceptable salt thereof, wherein one of $X_3$ to $X_6$ is a nitrogen atom, and the remaining three are —$CR^2$—.

(6) The compound of (3) or the pharmaceutically-acceptable salt thereof, wherein $X_2$ is a group of the formula (II).

(7) The compound of (3) or the pharmaceutically-acceptable salt thereof, wherein $X_2$ is a group of the formula (II); $R^4$, $R^5$ and the nitrogen atom to which they bond, taken together, form a pyrrolidine ring optionally substituted with a lower alkyl group, a piperidine ring optionally substituted with a lower alkyl group, an azepane ring optionally substituted with a lower alkyl group, or an azocane ring optionally substituted with a lower alkyl group; m is 3.

(8) The compound of (3) or the pharmaceutically-acceptable salt thereof, wherein $X_2$ is a group of the formula (III).

(9) The compound of (3) or pharmaceutically-acceptable salt thereof, wherein $X_2$ is a group of the formula (III), $R^6$ is a lower alkyl group or a cycloalkyl group, and n is 1 or 2.

(10) The compound of (3) or the pharmaceutically-acceptable salt thereof, wherein X is a sulfanyl group, a sulfinyl group or a sulfonyl group, and Y is an oxygen atom.

(11) The compound of (3) or the pharmaceutically-acceptable salt thereof, wherein X is an oxygen atom, and Y is a sulfanyl group, a sulfinyl group or a sulfonyl group.

(12) The compound of (3) or the pharmaceutically-acceptable salt thereof, wherein $R^1$ is a hydrogen atom, a lower alkyl group (the lower alkyl group may be substituted with a halogen atom), or a phenyl group.

The compound or its salt of above (1) to (12) acts as a histamine-H3 receptor antagonist or inverse-agonist in living bodies. Accordingly, the invention also provides a histamine-H3 receptor antagonist or inverse-agonist comprising the compound of above (1) to (12) or the pharmaceutically-acceptable salt thereof.

Recent studies have shown that a histamine-H3 receptor has extremely high homeostatic activities (activities observed in the absence of an endogenous agonistic factor (e.g., histamine)) in the receptor-expressing cells/tissues or in a membrane fraction derived from the expressing cells/tissues and even in living bodies (for example, see Nature, Vol. 408, p. 860). It is reported that these homeostatic activities are inhibited by an inverse-agonist. For example, thioperamide or syproxyfan inhibits the homeostatic self-receptor activity of a histamine-H3 receptor, and, as a result, promotes the release/liberation of neurotransmitters (e.g., histamine) from nerve ending.

Regarding rats, a high-level selective inhibitor of histamine synthase (histidine decarboxylase) inhibits the vigilance of rats, and therefore histamine participates in controlling motive vigilance. Regarding cats, administration of a histamine-H3 receptor agonist, (R)-(α)-methylhistamine to cats increases their deep slow-wave sleep (for example, see Brain Research, Vol. 523, p. 325 (1990)).

Contrary to this, thioperamide dose-dependently increases vigilance, and it decreases slow-wave and REM sleep (for example, see Life Science, Vol. 48, p. 2397 (1991)). A histamine-H3 receptor antagonist or inverse-agonist, thioperamide or GT-2331 reduces emotional cataplexy and sleep of narcoleptic dogs (for example, see Brain Research, Vol. 793, p. 279 (1998)).

These information suggests that the H3 receptor may participate in control of vigilance-sleep and in sleep disorder-associated diseases, further suggesting a possibility that a selective histamine-H3 agonist, antagonist or inverse-agonist may be useful for prevention or treatment of sleep disorders or various sleep disorder-associated diseases (for example, idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia). Accordingly, it may be considered that the compound or its salt of the invention may be effective for prevention and treatment of sleep disorders and various sleep disorder-associated diseases.

In rats, thioperamide or GT-2331 relieves the condition of learning disorder (LD) and attention deficit hyperactivity disorder (ADHD) (for example, see Life Science, Vol. 69, p. 469 (2001)). Further in rats, a histamine-H3 receptor agonist, (R)-(α)-methylhistamine lowers their object cognitive and learning effects in the object cognition test and the passive turnout test with them.

On the other hand, in a scopolamine-induced amnesia test, thioperamide dose-dependently relieves amnesia induced by the chemical (for example, see Pharmacology, Biochemistry and Behavior, Vol. 68, p. 735 (2001)).

These information suggests a possibility that a histamine-H3 receptor antagonist or inverse-agonist may be useful for prevention or treatment of memory/learning disorder and various diseases accompanied by it (e.g., Alzheimer's disease, Parkinson's disease, attention deficit/hyperactivity disorder). Accordingly, it may also be considered that the compound or its salt of the invention may be effective for prevention or treatment of such memory/learning disorder and various diseases accompanied by it.

Regarding rats, administration of histamine to their ventricle inhibits their eating action, therefore suggesting that histamine may participate in control of eating action (for example, see Journal of Physiology and Pharmacology, Vol. 49, p. 191 (1998)). In fact, thioperamide dose-dependently inhibits eating action and promotes intracerebral histamine release (for example, see Behavioral Brain Research, Vol. 104, p. 147 (1999)).

These information suggests that a histamine H3 receptor may participate in eating action control, further suggesting that a histamine-H3 antagonist or inverse-agonist may be useful for prevention or treatment of metabolic system diseases (metabolic syndromes) such as eating disorder, obesity, diabetes, emaciation, hyperlipemia. Accordingly, it may be considered that the compound or its salt of the invention may be effective also for prevention or treatment of such metabolic system diseases.

In rats, a histamine-H3 receptor agonist, (R)-(α)-methyl-histamine dose-dependently lowers their basal diastolic pressure, and its action is antagonized by thioperamide (for example, see European Journal of Pharmacology, Vol. 234, p. 129, (1993)).

These information suggests that a histamine-H3 receptor may participate in control of blood pressure, heart beat and cardiac output, further suggesting that a histamine-H3 receptor agonist, antagonist or inverse-agonist may be useful for prevention or treatment of circulatory system diseases such as hypertension and various cardiac disorders. Accordingly, it may be considered that the compound or its salt of the invention may be effective also for prevention or treatment of such circulatory system diseases.

In addition, it is shown that thioperamide dose-dependently inhibits the spasm induced by electric shock or the epileptoid seizure induced by pentylene tetrazole (PTZ) (for example, see European Journal of Pharmacology, Vol. 234, p. 129 (1993) and Pharmacology, Biochemistry and Behavior, Vol. 68, p. 735 (2001)).

These information suggests that a histamine-H3 receptor antagonist or inverse-agonist may be useful for prevention or treatment of epilepsy or central spasm. Accordingly, it may be considered that the compound or its salt of the invention may be effective also for prevention or treatment of such epilepsy or central spasm.

Accordingly, the invention further provides a preventive or remedy for metabolic system diseases, circulatory system diseases or nervous system diseases, which contains, as the active ingredient thereof, the compound of any one of above (1) to (12) or the pharmaceutically-acceptable salt thereof.

The metabolic system diseases are at least one selected from obesity, diabetes, hormone secretion disorder, hyperlipemia, gout and fatty liver.

The circulatory system diseases are at least one selected from stenocardia, acute/congestive cardiac insufficiency, cardiac infarction, coronary arteriosclerosis, hypertension, nephropathy and electrolyte disorder.

The nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism and tremor.

The nervous system diseases are also at least one selected from idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety and schizophrenia.

The compound or its salt of the invention may be used, as combined with co-drugs. Accordingly, the invention further provides a preventive or remedy for metabolic system diseases, circulator system diseases or nervous system diseases, which contains the compound of the invention or the pharmaceutically-acceptable salt thereof and a co-drug, as the active ingredients thereof. The co-drug includes a remedy for diabetes, a remedy for hyperlipemia, a remedy for hypertension, an anti-obesity drug. Two or more such co-drugs may be used herein, as combined.

As the preventive or remedy, the invention further provides a preventive or remedy for metabolic system diseases, circulator system diseases or nervous system diseases, which comprises the following (i), (ii) and (iii):

(i) a compound or a pharmaceutically-acceptable salt thereof of any one of above (1) to (12);
(ii) at least one selected from a group of the following (a) to (g):
(a) a histamine-H3 receptor antagonist or inverse-agonist except (i);
(b) a biguanide,
(c) a PPAR (peroxisome proliferator-activated receptor)-agonist;
(d) insulin,
(e) somatostatin,
(f) an α-glucosidase inhibitor,
(g) an insulin secretion promoter;
(iii) a pharmaceutically-acceptable carrier.

BEST MODE FOR CARRYING OUT THE INVENTION

The meanings of the terms used in this description are described first, and then the compounds of the invention are described.

"Aryl group" includes a hydrocarbon-ring aryl group having from 6 to 14 carbon atoms, for example, a phenyl group, a naphthyl group, a biphenyl group, an anthryl group et al.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group et al.

"Cycloalkyl group" means a cycloalkyl group having from 3 to 9 carbon atoms, concretely including, for example, a cyclopropyl group, a cyclobutyl group, a cyclopentyl group, a cyclohexyl group, a cycloheptyl group, a cyclooctyl group, a cyclononyl group et al.

"Lower alkoxy group" means a hydroxyl group of which the hydrogen atom is substituted with the above-mentioned lower alkyl group, including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group et al.

"Lower alkylsulfonyl group" means a sulfonyl group to which the above-mentioned alkyl group bonds, including a methylsulfonyl group, an ethylsulfonyl group, a propylsulfonyl group, an isopropylsulfonyl group, a butylsulfonyl group et al.

"Alkylsulfonylamino group" means an amino group of which one hydrogen atom is substituted with the above-mentioned lower alkylsulfonyl group, including, for example, a methylsulfonylamino group, an ethylsulfonylamino group, a propylsulfonylamino group, an isopropylsulfonylamino group, a butylsulfonylamino group, a sec-butylsulfonylamino group, a tert-butylsulfonylamino group, an N-methyl-methylsulfonylamino group, an N-methyl-ethylsulfonylamino group, an N-methyl-propylsulfonylamino group, an N-methyl-isopropylsulfonylamino group, an N-methyl-butylsulfonylamino group, an N-methyl-sec-butylsulfonylamino group, an N-methyl-tert-butylsulfonylamino group, an N-ethyl-methylsulfonylamino group, an N-ethyl-ethylsulfonylamino group, an N-ethyl-propylsulfonylamino group, an N-ethyl-isopropylsulfonylamino group, an N-ethyl-butylsulfonylamino group, an N-ethyl-sec-butylsulfonylamino group, an N-ethyl-tert-butylsulfonylamino group et al.

"Cycloalkylsulfonyl group" means a sulfonyl group to which the above-mentioned "cycloalkyl group" bonds, including, for example, a cyclopropylsulfonyl group, a cyclobutylsulfonyl group, a cyclopentylsulfonyl group, a cyclohexylsulfonyl group, a cycloheptylsulfonyl group, a cyclooctylsulfonyl group, a cyclononylsulfonyl group et al.

"Aralkyl group" means the above-mentioned lower alkyl group having the above-mentioned aryl group bonding thereto, including, for example, a benzyl group, a 1-phenylethyl group, a 2-phenylethyl group, a 1-naphthylmethyl group, a 2-naphthylmethyl group et al.

"Heteroaryl group" means a 5- to 7-membered monocyclic ring having from 1 to 3 hetero atoms selected from an oxygen atom, a sulfur atom and a nitrogen atom, or a bicyclic ring of the monocyclic ring condensed with a benzene ring or a pyridine ring, including, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolyl group, an isoquinolyl group, a quinazolyl group, a quinolidinyl group, an quinoxalinyl group, a cinnolinyl group, a benzimidazolyl group, a imidazopyridyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group et al.

"Halogen atom" is, for example, a fluorine atom, a chlorine atom, a bromine atom or an iodine atom.

"Lower alkoxycarbonylamino group" means a group formed of the above-defined lower alkoxy group bonding to a carbonylamino group, including, for example, a methoxycarbonylamino group, an ethoxycarbonylamino group, a propoxycarbonylamino group, an isopropoxycarbonylamino group, a butoxycarbonylamino group, a sec-butoxycarbonylamino group, a tert-butoxycarbonylamino group, a pentyloxycarbonylamino group, an N-methyl-methoxycarbonylamino group, an N-methyl-ethoxycarbonylamino group, an N-methyl-propoxycarbonylamino group, an N-methyl-isopropoxycarbonylamino group, an N-methyl-butoxycarbonylamino group, an N-methyl-sec-butoxycarbonylamino group, an N-methyl-tert-butoxycarbonylamino group, an N-ethyl-methoxycarbonylamino group, an N-ethyl-ethoxycarbonylamino group, an N-ethyl-propoxycarbonylamino group, an N-ethyl-isopropoxycarbonylamino group, an N-ethyl-butoxycarbonylamino group, an N-ethyl-sec-butoxycarbonylamino group, an N-ethyl-tert-butoxycarbonylamino group et al.

"Hydroxyalkyl group" means the above-mentioned lower alkyl group of which one hydrogen atom is substituted with a hydroxyl group, including a hydroxymethyl group, a hydroxyethyl group, a 1-hydroxypropyl group, a 1-hydroxyethyl group, a 2-hydroxypropyl group, a 2-hydroxy-1-methyl-ethyl group et al.

"Mono-lower alkylcarbamoyl group" means a carbamoyl group mono-substituted with the above-mentioned lower alkyl group, including a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group et al.

"Di-lower alkylcarbamoyl group" means a carbamoyl group di-substituted with the above-mentioned, same or different lower alkyl groups, including a dimethylcarbamoyl group, a diethylcarbamoyl group, an ethylmethylcarbamoyl group, a dipropylcarbamoyl group, a methylpropylcarbamoyl group, a diisopropylcarbamoyl group et al.

"Di-lower alkylcarbamoyl group" also includes a 4- to 9-membered monocyclic ring formed by the nitrogen atom of the carbamoyl group and the same or different lower alkyl groups bonding to the nitrogen atom, or a bicyclic ring formed through condensation of the monocyclic ring and a benzene ring or a pyridine ring, for example, the groups of the following formulae:

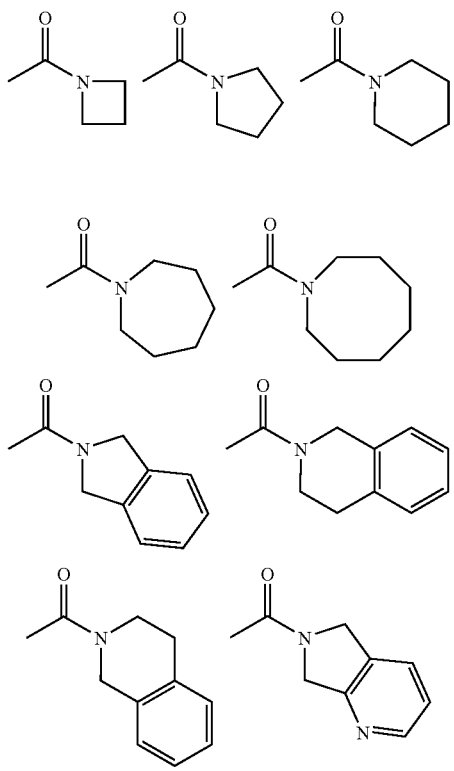

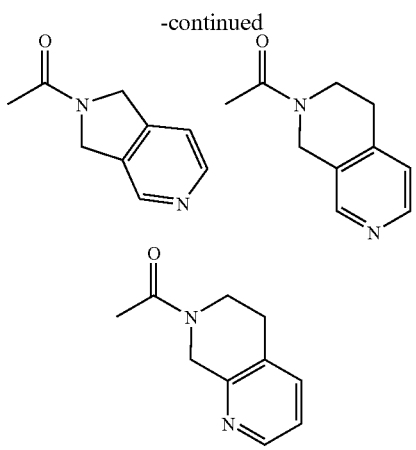

"Alkylamino group" means an amino group mono-substituted with the above-mentioned lower alkyl group, including a methylamino group, an ethylamino group, a propylamino group, an isopropylamino group, a butylamino group, a sec-butylamino group, a tert-butylamino group et al.

"Dialkylamino group" means an amino group di-substituted with the above-mentioned, same or different lower alkyl groups, including a dimethylamino group, a diethylamino group, a dipropylamino group, a methylpropylamino group, a diisopropylamino group et al.

"Aminoalkyl group" means the above-mentioned alkyl group of which one hydrogen atom is substituted with an amino group, including an aminomethyl group, an aminoethyl group, an aminopropyl group et al.

"Alkanoyl group" means a group of the above-mentioned lower alkyl group bonding to a carbonyl group, including an acetyl group, a propanoyl group, a butanoyl group, a pentanoyl group et al.

"Alkanoylamino group" means a group of the above-mentioned alkanoyl group bonding to an amino group, including an acetylamino group, a propanoylamino group, a butanoylamino group, a pentanoylamino group, an N-methyl-acetylamino group, an N-methyl-propanoylamino group, an N-methyl-butanoylamino group, an N-methyl-pentanoylamino group, an N-ethyl-acetylamino group, an N-ethyl-propanoylamino group, an N-ethyl-butanoylamino group, an N-ethyl-pentanoylamino group et al.

"Mono-lower alkylaminocarbonyloxy group" means an aminocarbonyloxy group mono-substituted with the above-mentioned lower alkyl group, including a methylaminocarbonyloxy group, an ethylaminocarbonyloxy group, a propylaminocarbonyloxy group, an isopropylaminocarbonyloxy group et al.

"Di-lower alkylaminocarbonyloxy group" means an aminocarbonyloxy group di-substituted with the above-mentioned, same or different lower alkyl groups, including a dimethylaminocarbonyloxy group, a diethylaminocarbonyloxy group, a diisopropylaminocarbonyloxy group, an ethylmethylaminocarbonyloxy group et al.

"Alkylthio group" means a group of the above-mentioned alkyl group bonding to a sulfur atom, including a methylthio group, an ethylthio group, a propylthio group, an isopropylthio group et al.

"Cycloalkoxy group" means a hydroxy group of which the hydrogen atom is substituted with the above-mentioned cycloalkyl group, including a cyclopropoxy group, a cyclobutoxy group, a cyclopentyloxy group, a cyclohexyloxy group, a cycloheptyloxy group.

"Aryloxy group" means the above-mentioned aryl group bonding to an oxygen atom, including a phenoxy group, a naphthalene-1-yloxy group, a naphthalene-2-yloxy group et al.

"Heteroaryloxy group" means the above-mentioned heteroaryl group bonding to an oxygen atom, including, for example, a furan-2-yloxy group, a furan-3-yloxy group, a thiophen-2-yloxy group, a thiophen-3-yloxy group, a 1H-pyrrol-2-yloxy group, a 1H-pyrrol-3-yloxy group, a 1H-imidazol-2-yloxy group, a 1H-imidazol-4-yloxy group, a 3H-imidazol-4-yloxy group, a 4H-[1,3,4]triazol-3-yloxy group, a 2H-[1,2,4]triazol-3-yloxy group, a 1H-[1,2,4]triazol-3-yloxy group, a thiazol-2-yloxy group, a thiazol-4-yloxy group, a thiazol-5-yloxy group, a pyridin-2-yloxy group, a pyridin-3-yloxy group, a pyridin-4-yloxy group, a pyrimidin-2-yloxy group, a pyrimidin-4-yloxy group, a pyrimidin-5-yloxy group, a pyridazin-3-yloxy group, a pyridazin-4-yloxy group, a 2H-pyrazol-3-yloxy group, a 1H-pyrazol-4-yloxy group, a 1H-pyrazol-yl-3-oxy group, a pyrazin-3-yloxy group, a pyrazin-4-yloxy group, a quinolin-2-yloxy group, a quinolin-3-yloxy group, a quinolin-4-yloxy group, an isoquinolin-1-yloxy group, an isoquinolin-3-yloxy group, an isoquinolin-4-yloxy group, a quinazolin-2-yloxy group, a quinazolinyl-3-yloxy group, a quinoxalin-2-yloxy group, a quinoxalin-3-yloxy group, a cinnolin-3-yloxy group, a cinnolin-4-yloxy group, a 1H-benzimidazol-2-yloxy group, a 1H-imidazo[4,5-b]pyridin-5-yloxy group, a 1H-imidazo[4,5-b]pyridin-6-yloxy group, a 1H-imidazo[4,5-b]pyridin-7-yloxy group, a benzo[d]isoxazol-4-yloxy group, a benzo[d]isoxazol-5-yloxy group, a benzo[d]isoxazol-6-yloxy group, a benzoxazol-4-yloxy group, a benzoxazol-5-yloxy group, a benzoxazol-6-yloxy group et al.

"Heteroarylalkyl group" means the above-mentioned heteroaryl group bonding to the above-mentioned alkyl group, including, for example, a furan-3-yl-methyl group, a furan-2-ylmethyl group, a furan-3-ylethyl group, a furan-2-ylethyl group, a furan-3-ylpropyl group, a furan-2-ylpropyl group, a thiophen-3-ylmethyl group, a thiophen-2-ylmethyl group, a thiophen-3-ylethyl group, a thiophen-2-ylethyl group, a thiophen-3-ylpropyl group, a thiophen-2-ylpropyl group, a 1H-pyrrol-3-ylmethyl group, a 1H-pyrrol-2-ylmethyl group, a 1H-pyrrol-3-ylethyl group, a 1H-pyrrol-2-ylethyl group, a 1H-pyrrol-3-ylpropyl group, a 1H-pyrrol-2-ylpropyl group, a 1H-imidazol-4-ylmethyl group, a 1H-imidazol-2-ylmethyl group, a 1H-imidazol-5-ylmethyl group, a 1H-imidazol-4-ylethyl group, a 1H-imidazol-2-ylethyl group, 1H-imidazol-5-ylethyl group, a 1H-imidazol-4-ylpropyl group, a 1H-imidazol-2-ylpropyl group, a 1H-imidazol-5-ylpropyl group, a 1H-[1,2,3]triazol-4-ylmethyl group, a 1H-[1,2,3]triazol-5-ylmethyl group, a 1H-[1,2,3]triazol-4-ylethyl group, a 1H-[1,2,3]triazol-5-ylethyl group, a 1H-[1,2,3]triazol-4-ylpropyl group, a 1H-[1,2,3]triazol-5-ylpropyl group, a 1H-[1,2,4]triazol-3-ylmethyl group, a 1H[1,2,4]triazol-5-ylmethyl group, a 1H-[1,2,4]triazol-3-ylethyl group, a 1H-[1,2,4]triazol-5-ylethyl group, a 1H-[1,2,4]triazol-3-ylpropyl group a 1H-[1,2,4]triazol-5-ylpropyl group, a thiazol-4-ylmethyl group, a thiazol-3-ylmethyl group, a thiazol-2-ylmethyl group, a thiazol-4-ylethyl group, a thiazol-3-ylethyl group, a thiazol-2-ylethyl group, a thiazol-4-ylpropyl group, a thiazol-3-ylpropyl group, a thiazol-2-ylpropyl group, a [1,2,4]thiadiazol-3-ylmethyl group, a [1,2,4]thiadiazol-3-ylethyl group, a [1,2,4]thiadiazol-3-ylpropyl group, a [1,2,4]thiadiazol-5-ylmethyl group, a 1,2,4]thiadiazol-5-ylethyl group, a [1,2,4]thiadiazol-5-ylpropyl group, a [1,3,4]thiadiazol-2-ylmethyl group, a [1,3,4]thiadiazol-2-ylethyl group, a [1,3,4]thiadiazol-2-ylpropyl group et al.

"Arylcarbamoyl group" means a carbamoyl group monosubstituted with the above-mentioned aryl group, including a phenylcarbamoyl group.

Next described are the symbols used in the formula (I) in the invention.

$R^1$ represents a hydrogen atom, a lower alkyl group (the lower alkyl group may be substituted with a lower alkoxy group or a halogen atom), a lower alkoxy group (the lower alkoxy group may be substituted with a halogen atom), an aryl group (the aryl group may be substituted with a lower alkyl group (the lower alkyl group may be substituted with a halogen atom), a lower alkoxy group (the lower alkoxy group may be substituted with a halogen atom) or a halogen atom), or a heteroaryl group (the heteroaryl group may be substituted with a lower alkyl group (the lower alkyl group may be substituted with a halogen atom), a lower alkoxy group (the lower alkoxy group may be substituted with a halogen atom), or a halogen atom).

"Lower alkyl group" for R' means the same group as the above-defined lower alkyl group, or the above-defined lower alkyl group substituted with a lower alkoxy group or a halogen atom et al.

The lower alkyl group concretely includes, for example, a methyl group, an ethyl group, a propyl group, an isopropyl group, a methoxymethyl group, a trifluoromethyl group, a difluoromethyl group, a fluoromethyl group et al.

"Lower alkoxy group" for $R^1$ means the same group as the above-defined lower alkoxy group, or the above-defined lower alkoxy group substituted with a halogen atom, concretely including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group, a methoxymethoxy group, a trifluoromethoxy group, a difluoromethoxy group, a fluoromethoxy group et al.

"Aryl group" for $R^1$ means the same group as the above-defined aryl group, or the above-defined aryl group substituted with the above-defined lower alkyl group (the lower alkyl group may be substituted with a halogen atom), a lower alkoxy group (the lower alkoxy group may be substituted with a halogen atom) or a halogen atom.

The aryl group concretely includes, for example, a phenyl group, a 2-methylphenyl group, a 3-methylphenyl group, a 4-methylphenyl group, a 2-trifluoromethylphenyl group, a 3-trifluoromethylphenyl group, a 4-trifluoromethylphenyl group, a 2-methoxymethylphenyl group, a 3-methoxymethylphenyl group, a 4-methoxymethylphenyl group, a 2-fluorophenyl group, a 3-fluorophenyl group, a 4-fluorophenyl group et al.

"Heteroaryl group" for $R^1$ means the same group as the above-defined heteroaryl group, or the above-defined heteroaryl group substituted with the above-defined lower alkyl group (the lower alkyl group may be substituted with a halogen atom), a lower alkoxy group (the lower alkoxy group may be substituted with a halogen atom) or a halogen atom.

$R^1$ is preferably a hydrogen atom, or a lower alkyl group or a phenyl group optionally substituted with a halogen atom, more recommendably a methyl group, an ethyl group, a propyl group, an isopropyl group, a tert-butyl group et al.

$R^2$ each independently represents a hydrogen atom, an amino group, an alkylamino group, a dialkylamino group, a nitro group, a cyano group, a hydroxyl group, a lower alkylsulfonyl group, a halogen atom, a lower alkyl group (the lower alkyl group may be substituted with a halogen atom), a cycloalkyl group (the cycloalkyl group may be substituted with a lower alkyl group or a halogen atom), a lower alkoxy group (the lower alkoxy group may be substituted with a halogen atom), a cycloalkoxy group, an aryloxy group, an aralkyloxy group, a heteroaryloxy group, a heteroarylalkyloxy group, an aryl group, a heteroaryl group, an arylcarbamoyl group, a heteroarylcarbamoyl group, an aralkylcarbamoyl group, a heteroarylalkylcarbamoyl group, a mono or di-lower alkylcarbamoyl group, an aryloxycarbonylamino group, an aralkyloxycarbonylamino group, a lower alkoxycarbonylamino group, an alkanoylamino group, an arylcarbonylamino group, a heteroarylcarbonylamino group, an aralkylcarbonylamino group, a heteroarylalkylcarbonylamino group, an alkanoyl group, an arylcarbonyl group, an aralkylcarbonyl group, a formyl group, an alkylthio group, an alkylsulfonylamino group, an arylsulfonylamino group, a mono or di-lower alkylsulfamoyl group, an arylsulfamoyl group, or an aralkyl group.

"Alkylamino group" for $R^2$ means the same group as the above-defined alkylamino group.

"Dialkylamino group" for $R^2$ means the same group as the above-defined dialkylamino group.

"Lower alkylsulfonyl group" for $R^2$ means the same group as the above-defined lower alkylsulfonyl group.

"Halogen atom" for $R^2$ means the same group as the above-defined halogen atom.

"Lower alkyl group" for $R^2$ means the same group as the above-defined lower alkyl group, or the above-defined lower alkyl group substituted with a lower alkoxy group or a halogen atom, and concretely includes, for example, a methyl group, an ethyl group, an isopropyl group, a propyl group, a trifluoromethyl group, a difluoromethyl group, a fluoromethyl group, a methoxymethyl group et al.

"Cycloalkyl group" for $R^2$ means the same group as the above-defined "cycloalkyl group", or the above-defined cycloalkyl group substituted with a lower alkyl group or a halogen atom, and concretely includes, for example, a cyclopropyl group, a cyclobutyl group, a cyclopentyl group, a cyclohexyl group, a cycloheptyl group, a cyclooctyl group, a cyclononyl group, a 2-fluorocyclopentyl group, a 3-fluorocyclopentyl group, a 3,3-difluorocyclohexyl group, a 2-methylcyclobutyl group, a 3-methylcyclobutyl group et al.

"Aralkyl group" for $R^2$ means the same group as the above-defined aralkyl group.

"Lower alkoxy group" for $R^2$ means the same group as the above-defined lower alkoxy group, or the above-defined lower alkoxy group substituted with a halogen atom, and concretely includes, for example, a methoxy group, an ethoxy group, a propoxy group, an isopropoxy group, a butoxy group, an isobutoxy group, a tert-butoxy group, a pentyloxy group, an isopentyloxy group, a hexyloxy group, an isohexyloxy group, a methoxymethoxy group, a trifluoromethoxy group, a difluoromethoxy group, a fluoromethoxy group et al.

"Cycloalkoxy group" for $R^2$ means the same group as the above-defined cycloalkoxy group.

"Aryloxy group" for $R^2$ means the same group as the above-defined aryloxy group.

"Heteroaryloxy group" for $R^2$ means the same group as the above-defined heteroaryloxy group.

"Aralkyloxy group" for $R^2$ means the above-defined aralkyl group to which an oxy group bonds, and is concretely, for example, a benzyloxy group.

"Aryl group" for $R^2$ means the same group as the above-defined aryl group.

"Heteroaryl group" for $R^2$ means the same group as the above-defined heteroaryl group.

"Heteroarylalkyloxy group" for $R^2$ means the above-defined heteroarylalkyl group to which an oxygen atom bonds, including, for example, a furan-3-yl-methoxy group, a furan-2-ylmethoxy group, a furan-3-ylethoxy group, a furan-2- ylethoxy group, a furan-3-ylpropoxy group, a furan-2-ylpropoxy group, a thiophen-3-ylmethoxy group, a thiophen-2-ylmethoxy group, a thiophen-3-ylethoxy group, a thiophen-2-ylethoxy group, a thiophen-3-ylpropoxy group, a thiophen-2-ylpropoxy group, a 1H-pyrrol-3-ylmethoxy group, a 1H-pyrrol-2-ylmethoxy group, a 1H-pyrrol-3-ylethoxy group, a 1H-pyrrol-2-ylethoxy group, a 1 h-pyrrol-3-ylpropoxy group, a 1H-pyrrol-2-ylpropoxy group, a 1H-imidazol-4-ylmethoxy group, a 1H-imidazol-2-ylmethoxy group, a 1H-imidazol-5-ylmethoxy group, a 1H-imidazol-4-ylethoxy group, a 1H-imidazol-2-ylethoxy group, a 1H-imidazol-5-ylethoxy group, a 1H-imidazol-4-ylpropoxy group, a 1H-imidazol-2-ylpropoxy group, a 1H-imidazol-5-ylpropoxy group, a 1H-[1,2,3]triazol-4-ylmethoxy group, a 1H-[1,2,3]triazol-5-ylmethoxy group, a 1H-[1,2,3]triazol-4-ylethoxy group, a 1H-[1,2,3]triazol-5-ylethoxy group, a 1H-[1,2,3]triazol-4-ylpropoxy group, a 1H-[1,2,3]triazol-5-ylpropoxy group, a 1H-[1,2,4]triazol-3-ylmethoxy group, a 1H-[1,2,4]triazol-5-ylmethoxy group, a 1H-[1,2,4]triazol-3-ylethoxy group, a 1H-[1,2,4]triazol-5-ylethoxy group, a 1H-[1,2,4]triazol-3-ylpropoxy group, a 1H-[1,2,4]triazol-5-ylpropoxy group, a thiazol-4-ylmethoxy group, a thiazol-3-ylmethoxy group, a thiazol-2-ylmethoxy group, a thiazol-4-ylethoxy group, a thiazol-3-ylethoxy group, a thiazol-2-ylethoxy group, a thiazol-4-ylpropoxy group, a thiazol-3-ylpropoxy group, a thiazol-2-ylpropoxy group, a [1,2,4]thiadiazol-3-ylmethoxy group, a [1,2,4]thiadiazol-3-ylethoxy group, a [1,2,4]thiadiazol-3-ylpropoxy group, a [1,2,4]thiadiazol-5-ylmethoxy group, a [1,2,4]thiadiazol-5-ylethoxy group, a [1,2,4]thiadiazol-5-ylpropoxy group, a [1,3,4]thiadiazol-2-ylmethoxy group, a [1,3,4]thiadiazol-2-ylethoxy group, a [1,3,4]thiadiazol-2-ylpropoxy group et al.

"Arylcarbamoyl group" for $R^2$ means the same group as the above-defined arylcarbamoyl group.

"Heteroarylcarbamoyl group" for $R^2$ means the above-defined heteroaryl group bonding to a carbamoyl group, including, for example, a furan-3-ylcarbamoyl group, a furan-2-ylcarbamoyl group, a thiophen-3-ylcarbamoyl group, a thiophen-2-ylcarbamoyl group et al.

"Heteroarylalkylcarbamoyl group" for $R^2$ means the above-defined heteroarylalkyl group bonding to a carbamoyl group, including, for example, a furan-3-yl-methylcarbamoyl group, a furan-2-ylmethylcarbamoyl group, a furan-3-ylethylcarbamoyl group, a furan-2-ylethylcarbamoyl group, a furan-3-ylpropylcarbamoyl group, a furan-2-ylpropylcarbamoyl group, a thiophen-3-ylmethylcarbamoyl group, a thiophen-2-ylmethylcarbamoyl group, a thiophen-3-ylethylcarbamoyl group, a thiophen-2-ylethylcarbamoyl group, a thiophen-3-ylpropylcarbamoyl group, a thiophen-2-ylpropylcarbamoyl group et al.

"Aralkylcarbamoyl group" for $R^2$ means the above-defined aralkyl group bonding to a carbamoyl group, including, for example, a benzylcarbamoyl group et al.

"Mono or di-lower alkylcarbamoyl group" for $R^2$ means the same group as the above-defined "mono-lower alkylcarbamoyl group" or "di-lower alkylcarbamoyl group".

"Aryloxycarbonylamino group" for $R^2$ means the above-defined aryloxy group bonding to a carbonylamino group, concretely including, for example, a phenoxycarbonylamino group.

"Aralkyloxycarbonylamino group" for $R^2$ means the above-defined "aralkyloxy group" bonding to a carbonylamino group, concretely including, for example, a benzyloxycarbonylamino group et al.

"Lower alkoxycarbonylamino group" for $R^2$ means the same group as the above-defined "lower alkoxycarbonylamino group".

"Alkanoylamino group" for $R^2$ means the same group as the above-defined "alkanoylamino group".

"Arylcarbonylamino group" for $R^2$ means the above-defined aryl group bonding to a carbonylamino group, concretely including, for example, a phenylcarbonylamino group et al.

"Heteroarylcarbonylamino group" for $R^2$ means the above-defined heteroaryl group bonding to a carbonylamino group, concretely including, for example, a furan-3-ylcarbonylamino group, a furan-2-ylcarbonylamino group, a thiophen-3-ylcarbonylamino group, a thiophen-2-ylcarbonylamino group et al.

"Aralkylcarbonylamino group" for $R^2$ means the above-defined aralkyl group bonding to a carbonylamino group, concretely including, for example, a benzylcarbonylamino group et al.

"Heteroarylalkylcarbonylamino group" for $R^2$ means the above-defined heteroarylalkyl group bonding to a carbonylamino group, concretely including, for example, a furan-3-yl-methylcarbonylamino group, a furan-2-ylmethylcarbonylamino group, a furan-3-ylethylcarbonylamino group, a furan-2-ylethylcarbonylamino group, a furan-3-ylpropylcarbonylamino group, a furan-2-ylpropylcarbonylamino group, a thiophen-3-ylmethylcarbonylamino group, a thiophen-2-ylmethylcarbonylamino group, a thiophen-3-ylethylcarbonylamino group, a thiophen-2-ylethylcarbonylamino group, a thiophen-3-ylpropylcarbonylamino group, a thiophen-2-ylpropylcarbonylamino group et al.

"Alkanoyl group" for $R^2$ means the same group as the above-defined "alkanoyl group".

"Arylcarbonyl group" for $R^2$ means the above-defined "aryl group" bonding to a carbonyl group, concretely including, for example, a phenylcarbonyl group et al.

"Aralkylcarbonyl group" for $R^2$ means the above-defined "aralkyl group" bonding to a carbonyl group, concretely including, for example, a benzylcarbonyl group et al.

"Alkylthio group" for $R^2$ means the same group as the above-defined "alkylthio group".

"Alkoxycarbonylamino group" for $R^2$ means the above-defined "lower alkoxy group" bonding to a carbonylamino group, concretely including, for example, a methoxycarbonylamino group, an ethoxycarbonylamino group, a propylcarbonylamino group et al.

"Alkylsulfonylamino group" for $R^2$ means the same group as the above-defined alkylsulfonylamino group.

"Arylsulfonylamino group" for $R^2$ means the above-defined aryl group bonding to a sulfonylamino group, concretely including, for example, a phenylsulfonylamino group et al.

"Mono or di-lower alkylsulfamoyl group" for $R^2$ means a sulfamoyl group substituted with the above-defined, same or different lower alkyl group(s), concretely including, for example, a methylsulfamoyl group, an ethylmethylsulfamoyl group, an ethylsulfamoyl group, a propylsulfamoyl group et al.

"Arylsulfamoyl group" for $R^2$ means a sulfamoyl group substituted with the above-defined aryl group, concretely including, for example, a phenylsulfamoyl group et al.

Preferably and recommendably, $R^2$ is each independently a hydrogen atom, a lower alkyl group (the lower alkyl group may be substituted with the same or different halogen atoms), a halogen atom or a lower alkoxy group (the lower alkoxy group may be substituted with the same or different halogen atoms).

One of X and Y is an oxygen atom, and the other is a sulfanyl group, a sulfinyl group or a sulfonyl group.

The group of a formula (II):

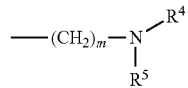

(II)

[wherein the symbols are the same as above] for $X_2$ is described.

"Lower alkyl group" for $R^4$ and $R^5$ means the same group as the above-defined lower alkyl group, or the above-defined lower alkyl group substituted with a halogen atom.

"Cycloalkyl group" for $R^4$ and $R^5$ means the same group as the above-defined cycloalkyl group, or the above-defined "cycloalkyl" group substituted with a lower alkyl group or a halogen atom.

$R^4$ and $R^5$ may be the same or different.

In the formula (II), $R^4$, $R^5$ and the nitrogen atom, taken together, may form a 4- to 9-membered monocyclic ring (the monocyclic ring may have, in the ring, still another hetero atom selected from a nitrogen atom, a sulfur atom and an oxygen atom, in addition to the nitrogen atom to which $R^4$ and $R^5$ bond). The monocyclic ring may be substituted with a lower alkyl group (the lower alkyl group may be substituted with a halogen atom), a halogen atom, a hydroxyl group or an oxo group.

The monocyclic ring includes, for example a pyrrolidine ring, a (2R)-2-methylpyrrolidine ring, a (2S)-2-methylpyrrolidine ring, a (3R)-3-methylpyrrolidine ring, a (3S)-3-methylpyrrolidine ring, a (2R)-2-fluoropyrrolidine ring, a (2S)-2-fluoropyrrolidine ring, a 2,2-difluoropyrrolidine ring, a (3R)-3-hydroxypyrrolidine ring, a (3S)-3-hydroxypyrrolidine ring, a piperidine ring, a (2R)-2-methylpiperidine ring, a (2S)-2-methylpiperidine ring, a (3R)-3-methylpiperidine ring, a (3S)-3-methylpiperidine ring, a (4R)-4-methylpiperidine ring, a (4S)-4-methylpiperidine ring, a (2R)-2-fluoropiperidine ring, a (2S)-2-fluoropiperidine ring, a 2,2-difluoropiperidine ring, an azepane ring, a (2R)-2-methylazepane ring, a (2S)-2-methylazepane ring, a (3R)-3-methylazepane ring, a (3S)-3-methylazepane ring, an azocane ring, a piperazine ring, a morpholine ring, a homomorpholine ring et al.

In the formula (II), $R^4$, $R^5$ and the nitrogen, taken together, may form a bicyclic ring. The bicyclic ring is an azabicyclic ring, and this is a non-aromatic ring that contains, as only one hetero atom constituting the ring, the nitrogen atom to which $R^4$ and $R^5$ bond in the formula (II). The bicyclic ring preferably has from 6 to 10 ring-constituting atoms, more preferably from 7 to 9 ring-constituting atoms. The bicyclic ring may be substituted with a lower alkyl group (the lower alkyl group may be substituted with a halogen atom), a halogen atom, a hydroxyl group or an oxo group.

The bicyclic ring includes, for examples, groups of a formula (V):

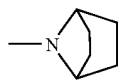 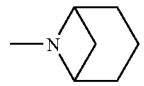 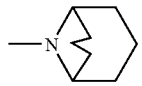

(V)

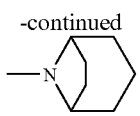

$CH_2$ in the formula (II) may be substituted with a lower alkyl group having 1 or 2 carbon atoms. The lower alkyl group includes a methyl group, an ethyl group, an n-propyl group, an isopropyl group.

m indicates an integer of from 2 to 4.

Preferably, $R^4$ and $R^5$ are each independently a methyl group, an ethyl group, an n-propyl group, an isopropyl group et al.

Specific examples of the 4- to 9-membered monocyclic or bicyclic ring to be formed by $R^4$, $R^5$ and the nitrogen taken together are preferably, for example, a pyrrolidine ring, a (2R)-2-methylpyrrolidine ring, a (2S)-2-methylpyrrolidine ring, a (3R)-3-methylpyrrolidine ring, a (3S)-3-methylpyrrolidine ring, a piperidine ring, a (2R)-2-methylpiperidine ring, a (2S)-2-methylpiperidine ring, a (3R)-3-methylpiperidine ring, a (3S)-3-methylpiperidine ring, a (4R)-4-methylpiperidine ring, a (4S)-4-methylpiperidine ring, an azepane ring, a (2R)-2-methylazepane ring, a (2S)-2-methylazepane ring, a (3R)-3-methylazepane ring, a (3S)-3-methylazepane ring, an azocane ring et al.

The group of a formula (III):

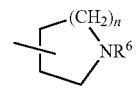

(III)

[wherein the symbols are the same as above] for $X_2$ is described.

n indicates from 0 to 4.

$R^6$ is a lower alkyl group (the lower alkyl group may be substituted with a halogen atom), or a cycloalkyl group (the cycloalkyl group may be substituted with a lower alkyl group or a halogen atom).

"Lower alkyl group" for $R^6$ means the same group as the above-defined lower alkyl group, or the above-defined lower alkyl group substituted with a halogen atom, concretely including, for example, a methyl group, an ethyl group, an n-propyl group, an isopropyl group, a butyl group, an isobutyl group, a sec-butyl group, a tert-butyl group, a pentyl group, an isoamyl group, a neopentyl group, a trifluoromethyl group, a difluoromethyl group, a fluoromethyl group et al.

"Cycloalkyl group" for $R^6$ means the same group as the above-defined cycloalkyl group, or the above-defined cycloalkyl group substituted with a lower alkyl group or a halogen atom, concretely including, for example, a cyclopropyl group, a cyclobutyl group, a cyclopentyl group, a cyclohexyl group, a cycloheptyl group, a cyclooctyl group, a cyclononyl group, a 2-fluorocyclopentyl group, a 3-fluorocyclopentyl group, a 3,3-difluorocyclohexyl group, a 2-methylcyclobutyl group, a 3-methylcyclobutyl group.

$R^6$ is preferably and recommendably an n-propyl group, an isopropyl group, an n-butyl group, an isobutyl group, a sec-butyl group, a tert-butyl group, an n-pentyl group, an isoamyl group, a neopentyl group, a cyclopropyl group, a cyclobutyl group, a cyclopentyl group, a cyclohexyl group et al.

Preferably and recommendably, n is 1 or 2.

In case where $X_2$ is represented by the formula (III), two different carbon atoms of the carbon atoms constituting $X_2$ may bond via $-(CH_2)_{n11}-$ (n11 indicates an integer of from 1 to 3), thereby forming a bicyclic ring. The bicyclic ring includes, for example, groups of a formula (III-2):

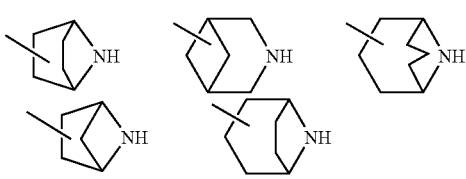

The group of a formula (IV):

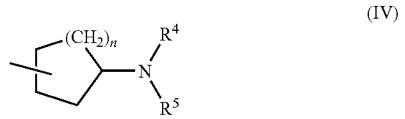

[wherein the symbols are the same as above] for $X_2$ is described.

n indicates from 0 to 4.

$R^4$ and $R^5$ have the same meanings as above, and their preferred embodiments are also the same as above.

In case where $X_2$ is represented by the formula (IV), two different carbon atoms of the carbon atoms constituting $X_2$ (but excepting the carbon atoms in $R^4$ and $R^5$) may bond via a single bond or —$(CH_2)_{n11}$— (n11 indicates an integer of from 1 to 3), thereby forming a bicyclic ring. The bicyclic ring includes, for example, groups of a formula (IV-2):

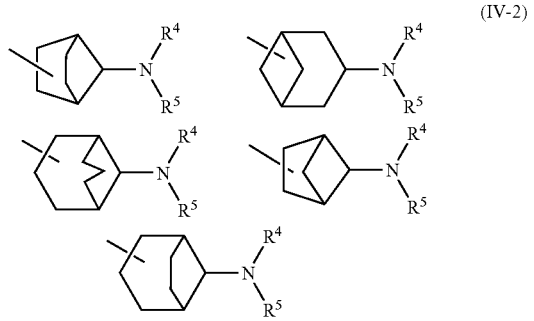

[wherein the symbols have the same meanings as above.]

In case where $X_2$ is a bicyclic ring of the above formula (IV-2), the preferred embodiments of $R^4$ and $R^5$ are the same as above.

From the above, $X_2$ includes, for example, a 2-dimethylamino-ethyl group, a 2-diethylamino-ethyl group, a 2-di-n-propylamino-ethyl group, a 2-diisopropylamino-ethyl group, a 3-dimethylamino-propyl group, a 3-diethylamino-propyl group, a 3-di-n-propylamino-propyl group, a 3-diisopropylamino-propyl group, a 4-dimethylamino-butyl group, a 4-diethylamino-butyl group, a 4-di-n-propylamino-butyl group, a 4-diisopropylamino-butyl group, a 2-(ethylmethylamino)ethyl group, a 2-(ethylpropylamino)ethyl group, a 2-(ethylisopropylamino)ethyl group, a 2-(methylisopropylamino)ethyl group, a 2-(ethyl-n-propyl-amino)ethyl group, a 3-(ethylmethylamino)propyl group, a 3-(ethylpropylamino)propyl group, a 3-(ethylisopropylamino)propyl group, a 3-(methylisopropylamino)propyl group, a 2-(ethyl-n-propyl-amino)propyl group, a 4-(ethylmethylamino)butyl group, a 4-(ethylpropylamino)butyl group, a 4-(ethylisopropylamino) butyl group, a 2-(ethyl-n-propyl-amino)butyl group, a 2-dicyclopropylamino-ethyl group, a 2-dicyclobutylamino-ethyl group, a 2-dicyclopentylamino-ethyl group, a 2-dicyclohexylamino-ethyl group, a 3-dicyclopropylamino-propyl group, a 3-dicyclobutylamino-propyl group, a 3-dicyclopentylamino-propyl group, a 3-dicyclohexylamino-propyl group, a 4-dicyclopropylamino-butyl group, a 4-dicyclobutylamino-butyl group, a 4-dicyclopentylamino-butyl group, a 4-dicyclohexylamino-butyl group, a 2-(cyclobutyl-cyclopropylamino)ethyl group, a 2-(cyclobutyl-cyclopentyl-amino)ethyl group, a 2-(cyclohexyl-cyclopentyl-amino)ethyl group, a 3-(cyclobutyl-cyclopropyl-amino)propyl group, a 3-(cyclobutyl-cyclopentyl-amino)propyl group, a 3-(cyclohexyl-cyclopentyl-amino)propyl group, a 4-(cyclobutyl-cyclopropyl-amino) butyl group, a 4-(cyclobutyl-cyclopentyl-amino)butyl group, a 4-(cyclohexyl-cyclopentyl-amino)butyl group, a 2-(cyclopropyl-methyl-amino)ethyl group, a 2-(cyclopropyl-ethyl-amino)ethyl group, a 2-(cyclopropyl-n-propyl-amino)ethyl group, a 2-(cyclopropyl-isopropyl-amino)ethyl group, a 2-(cyclobutyl-methyl-amino)ethyl group, a 2-(cyclobutyl-ethyl-amino)ethyl group, a 2-(cyclobutyl-n-propyl-amino) ethyl group, a 2-(cyclobutyl-isopropyl-amino)ethyl group, a 2-(cyclopentyl-methyl-amino)ethyl group, a 2-(cyclopentyl-ethyl-amino)ethyl group, a 2-(cyclopentyl-n-propyl-amino) ethyl group, a 2-(cyclopentyl-isopropyl-amino)ethyl group, a 2-(cyclohexyl-methyl-amino)ethyl group, a 2-(cyclohexyl-ethyl-amino)ethyl group, a 2-(cyclohexyl-n-propyl-amino) ethyl group, a 2-(cyclohexyl-isopropyl-amino)ethyl group, a 3-(cyclopropyl-methyl-amino)propyl group, a 3-(cyclopropyl-ethyl-amino)propyl group, a 3-(cyclopropyl-n-propyl-amino)propyl group, a 3-(cyclopropyl-isopropyl-amino)propyl group, a 3-(cyclobutyl-methyl-amino)propyl group, a 3-(cyclobutyl-ethyl-amino)propyl group, a 3-(cyclobutyl-n-propyl-amino)propyl group, a 3-(cyclobutyl-isopropyl-amino)propyl group, a 3-(cyclopentyl-methyl-amino)propyl group, a 3-(cyclopentyl-ethyl-amino)propyl group, a 3-(cyclopentyl-n-propyl-amino)propyl group, a 3-(cyclopentyl-isopropyl-amino)propyl group, a 3-(cyclohexyl-methyl-amino)propyl group, a 3-(cyclohexyl-ethyl-amino)propyl group, a 3-(cyclohexyl-n-propyl-amino)propyl group, a 3-(cyclohexyl-isopropyl-amino)propyl group, a 4-(cyclopropyl-methyl-amino)butyl group, a 4-(cyclopropyl-ethyl-amino)butyl group, a 4-(cyclopropyl-n-propyl-amino)butyl group, a 4-(cyclopropyl-isopropyl-amino)butyl group, a 4-(cyclobutyl-methyl-amino)butyl group, a 4-(cyclobutyl-ethyl-amino)butyl group, a 4-(cyclobutyl-n-propyl-amino) butyl group, a 4-(cyclobutyl-isopropyl-amino)butyl group, a 4-(cyclopentyl-methyl-amino)butyl group, a 4-(cyclopentyl-ethyl-amino)butyl group, a 4-(cyclopentyl-n-propyl-amino) butyl group, a 4-(cyclopentyl-isopropyl-amino)butyl group, a 4-(cyclohexyl-methyl-amino)butyl group, a 4-(cyclohexyl-ethyl-amino)butyl group, a 4-(cyclohexyl-n-propyl-amino) butyl group, a 4-(cyclohexyl-isopropyl-amino)butyl group, a 2-azetidin-1-ylethyl group, a 2-pyrrolidin-1-ylethyl group, a 2-piperidin-1-ylethyl group, a 2-azepan-1-ylethyl group, a 2-azocan-1-ylethyl group, a 2-azonan-1-ylethyl group, a 2-morpholin-4-ylethyl group, a 2-homomorpholin-4-ylethyl group, a 3-azetidin-1-ylpropyl group, a 3-pyrrolidin-1-ylpropyl group, a 3-piperidin-1-ylpropyl group, a 3-azepan-1-ylpropyl group, a 3-azocan-1-ylpropyl group, a 3-azonan-1-ylpropyl group, a 3-morpholin-4-ylpropyl group, a 3-homomorpholin-4-ylpropyl group, a 4-azetidin-1-ylbutyl group, a 4-pyrrolidin-1-ylbutyl group, a 4-piperidin-1-ylbutyl group, a 4-azepan-1-ylbutyl group, a 4-azocan-1-ylbutyl group, a 4-azonan-1-ylbutyl group, a 4-morpholin-4-ylbutyl group, a 4-homomorpholin-4-ylbutyl group, a 2-(5-aza-bicyclo[2.1.1]hexan-5-yl)ethyl group, a 2-(6-aza-bicyclo[3.1.1] heptan-6-yl)ethyl group, a 2-(7-aza-bicyclo[2.1.1]heptan-7-yl)ethyl group, a 2-(8-aza-bicyclo[3.2.1]octan-8-yl)ethyl group, a 2-(9-aza-bicyclo[3.3.1]nonan-9-yl)ethyl group, a 3-(5-aza-bicyclo[2.1.1]hexan-5-yl)propyl group, a 3-(6-aza-bicyclo[3.1.1]heptan-6-yl)propyl group, a 3-(7-aza-bicyclo[2.2.1]heptan-7-yl)propyl group, a 3-(8-aza-bicyclo[3.2.1]octan-8-ylpropyl group, a 3-(9-aza-bicyclo[3.3.1]nonan-9-yl)propyl group, a 4-(5-aza-bicyclo[2.1.1]hexan-5-yl)butyl group, a 4-(6-aza-bicyclo[3.1.1]heptan-6-yl)butyl group, a 4-(7-aza-bicyclo[2.2.1]heptan-7-yl)butyl group, a 4-(8-aza-bicyclo[3.2.1]octan-8-ylbutyl group, a aza-bicyclo[3.3.1]nonan-9-ylbutyl group, a 1-methylazetidin-3-yl group, a 1-methylazetidin-2-yl group, a 1-ethylazetidin-3-yl group, a 1-ethylazetidin-2-yl group, a 1-isopropylazetidin-3-yl group, a 1-isopropylazetidin-2-yl group, a 1-cyclopropylazetidin-3-yl group, a 1-cyclopropylazetidin-2-yl group, a 1-cyclobutylazetidin-3-yl group, a 1-cyclobutylazetidin-2-yl group, a 1-cyclopentylazetidin-3-yl group, a 1-cyclopentylazetidin-2-yl group, a 1-cyclohexylazetidin-3-yl group, a 1-cyclohexylazetidin-2-yl group, a 1-methylpyrrolidin-3-yl group, a 1-methylpyrrolidin-2-yl group, a 1-ethylpyrrolidin-3-yl group, a 1-ethylpyrrolidin-3-yl group, a 1-isopropylpyrrolidin-3-yl group, a 1-isopropyl-pyrrolidin-2-yl group, a 1-cyclopropylpyrrolidin-3-yl group, a 1-cyclopropylpyrrolidin-2-yl group, a 1-cyclobutylpyrrolidin-3-yl group, a 1-cyclobutylpyrrolidin-2-yl group, a 1-cyclopentylpyrrolidin-3-yl group, a 1-cyclopentylpyrrolidin-2-yl group, a 1-cyclohexylpyrrolidin-3-yl group, a 1-cyclohexylpyrrolidin-2-yl group, a 1-methylpiperidin-4-yl group, a 1-methylpiperidin-3-yl group, a 1-methylpiperidin-2-yl group, a 1-ethylpiperidin-4-yl group, a 1-ethylpiperidin-3-yl group, a 1-ethylpiperidin-2-yl group, a 1-isopropylpiperidin-4-yl group, a 1-isopropylpiperidin-3-yl group, a 1-isopropylpiperidin-2-yl group, a 1-propylpiperidin-4-yl group, a 1-propylpiperidin-3-yl group, a 1-propylpiperidin-2-yl group, a 1-butylpiperidin-4-yl group, a 1-butylpiperidin-3-yl group, a 1-butylpiperidin-2-yl group, a 1-sec-butylpiperidin-4-yl group, a 1-sec-butylpiperidin-3-yl group, a 1-sec-butylpiperidin-2-yl group, a 1-tert-butylpiperidin-4-yl group, a 1-tert-butylpiperidin-3-yl group, a 1-tert-butylpiperidin-2-yl group, a 1-pentylpiperidin-4-yl group, a 1-pentylpiperidin-3-yl group, a 1-pentylpiperidinpiperidin-2-yl group, a 1-isoamylpiperidin-4-yl group, a 1-isoamylpiperidin-3-yl group, a 1-isoamylpiperidin-2-yl group, a 1-neopentylpiperidin-4-yl group, a 1-neopentylpiperidin-3-yl group, a 1-neopentylpiperidin-2-yl group, a 1-cyclopropylpiperidin-4-yl group, a 1-cyclopropylpiperidin-3-yl group, a 1-cyclopropylpiperidin-2-yl group, a 1-cyclobutylpiperidin-4-yl group, a 1-cyclobutylpiperidin-3-yl group, a 1-cyclobutylpiperidin-2-yl group, a 1-cyclopentylpiperidin-4-yl group, a 1-cyclopentylpiperidin-3-yl group, a 1-cyclopentylpiperidin-2-yl group, a 1-cyclohexylpiperidin-4-yl group, a 1-cyclohexylpiperidin-3-yl group, a 1-cyclohexylpiperidin-2-yl group, a 3-dimethylaminocyclobutyl group, a 3-diethylaminocyclobutyl group, a 3-diisopropylaminocyclobutyl group, a 3-dicyclopropylaminobutyl group, a 3-dicyclobutylaminobutyl group, a 3-dicyclopentylaminobutyl group, a 3-dicyclohexylaminobutyl group, a 2-dimethylaminocyclobutyl group, a 2-diethylaminocyclobutyl group, a 2-diisopropylaminocyclobutyl group, a 2-dicyclopropylaminobutyl group, a 2-dicyclobutylaminobutyl group, a 2-dicyclopentylaminobutyl group, a 2-dicyclohexylaminobutyl group; a 3-(cyclopropyl-methylamino)cyclobutyl group, a 3-(cyclopropyl-ethyl-amino)cyclobutyl group, a 3-(cyclobutyl-methyl-amino)cyclobutyl group, a 3-(cyclobutyl-ethyl-amino)cyclobutyl group, a 3-(cyclopentyl-methyl-amino)cyclobutyl group, a 3-(cyclopentyl-ethyl-amino)cyclobutyl group, a 3-(cyclohexyl-methyl-amino)cyclobutyl group, a 2-(cyclopropyl-methyl-amino)cyclobutyl group, a 2-(cyclopropyl-ethyl-amino)cyclobutyl group, a 2-(cyclobutyl-methyl-amino)cyclobutyl group, a 2-(cyclobutyl-ethyl-amino)cyclobutyl group, a 2-(cyclopentyl-methyl-amino)cyclobutyl group, a 2-(cyclopentyl-ethyl-amino)cyclobutyl group, a 2-(cyclohexyl-methyl-amino)cyclobutyl group, a 3-pyrrolidin-1-yl-cyclobutyl group, a 2-pyrrolidin-1-yl-cyclobutyl group, a 3-pyrrolidin-1-yl-cyclopentyl group, a 2-pyrrolidin-1-yl-cyclopentyl group, a 4-pyrrolidin-1-yl-cyclohexyl group, a 3-pyrrolidin-1-yl-cyclohexyl group, a 2-pyrrolidin-1-yl-cyclohexyl group, a 3-piperidin-1-yl-cyclobutyl group, a 2-piperidin-1-yl-cyclobutyl group, a 3-piperidin-1-yl-cyclopentyl group, a 2-piperidin-1-yl-cyclopentyl group, a 4-piperidin-1-yl-cyclohexyl group, a 3-piperidin-1-yl-cyclohexyl group, a 2-piperidin-1-yl-cyclohexyl group, a 3-azepan-1-yl-cyclobutyl group, a 2-azepan-1-yl-cyclobutyl group, a 3-azepan-1-yl-cyclopentyl group, a 2-azepan-1-yl-cyclopentyl group, a 4-azepan-1-yl-cyclohexyl group, a 3-azepan-1-yl-cyclohexyl group, a 2-azepan-1-yl-cyclohexyl group, a 3-azocan-1-yl-cyclobutyl group, a 2-azocan-1-yl-cyclobutyl group, a 3-azocan-1-yl-cyclopentyl group, a 2-azocan-1-yl-cyclopentyl group, a 4-azocan-1-yl-cyclohexyl group, a 3-azocan-1-yl-cyclohexyl group, a 2-azocan-1-yl-cyclohexyl group, a 2-morpholin-4-yl-cyclobutyl group, a 3-morpholin-4-yl-cyclobutyl group, a 2-morpholin-4-yl-cyclopentyl group, a 3-morpholin-4-yl-cyclopentyl group, a 2-morpholin-4-yl-cyclohexyl group, a 3-morpholin-4-yl-cyclohexyl group, a 4-morpholin-4-yl-cyclohexyl group, a 2-homomorpholin-4-yl-cyclobutyl group, a 3-homomorpholin-4-yl-cyclobutyl group, a 4-homomorpholin-4-yl-cyclobutyl group, a 2-homomorpholin-4-yl-cyclopentyl group, a 3-homomorpholin-4-yl-cyclopentyl group, a 4-homomorpholin-4-yl-cyclopentyl group, a 2-homomorpholin-4-yl-cyclohexyl group, a 3-homomorpholin-4-yl-cyclohexyl group, a 4-homomorpholin-4-yl-cyclohexyl group, a 2-(5-aza-bicyclo[2.1.1]hexan-5-yl)cyclobutyl group, a 2-(6-aza-bicyclo[3.1.1]heptan-6-yl)cyclobutyl group, a 2-(7-aza-bicyclo[2.2.1]heptan-7-yl)cyclobutyl group, a 2-(8-aza-bicyclo[3.2.1]octan-8-yl)cyclobutyl group, a 2-(9-aza-bicyclo[3.3.1]nonan-9-yl)cyclobutyl group, a 3-(5-aza-bicyclo[2.1.1]hexan-5-yl)cyclobutyl group, a 3-(6-aza-bicyclo[3.1.1]heptan-6-yl)cyclobutyl group, a 3-(7-aza-bicyclo[2.2.1]heptan-7-yl)cyclobutyl group, a 3-(8-aza-bicyclo[3.2.1]octan-8-yl)cyclobutyl group, a 3-(9-aza-bicyclo[3.3.1]nonan-9-yl)cyclobutyl group, a 2-(5-aza-bicyclo[2.1.1]hexan-5-yl)cyclopentyl group, a 2-(6-aza-bicyclo[3.1.1]heptan-6-yl)cyclopentyl group, a 2-(7-aza-bicyclo[2.2.1]heptan-7-yl)cyclopentyl group, a 2-(8-aza-bicyclo[3.2.1]octan-8-yl)cyclopentyl group, a 2-(9-aza-bicyclo[3.3.1]nonan-9-yl)cyclopentyl group, a 3-(5-aza-bicyclo[2.1.1]hexan-5-yl)cyclopentyl group, a 3-(6-aza-bicyclo[3.1.1]heptan-6-yl)cyclopentyl group, a 3-(7-aza-bicyclo[2.2.1]heptan-7-yl)cyclopentyl group, a 3-(8-aza-bicyclo[3.2.1]octan-8-yl)cyclopentyl group, a 3-(9-aza-bicyclo[3.3.1]nonan-9-yl)cyclopentyl group, a 2-(5-aza-bicyclo[2.1.1]hexan-5-yl)cyclohexyl group, a 2-(6-aza-bicyclo[3.1.1]heptan-6-yl)cyclohexyl group, a 2-(7-aza-bicyclo[2.2.1]heptan-7-yl)cyclohexyl group, a 2-(8-aza-bicyclo[3.2.1]octan-8-yl)cyclohexyl group, a 2-(9-aza-bicyclo[3.3.1]nonan-9-yl)cyclohexyl group, a 3-(5-aza-bicyclo[2.1.1]hexan-5-yl)cyclohexyl group, a 3-(6-aza-bicyclo[3.1.1]heptan-6-yl)cyclohexyl group, a 3-(7-aza-bicyclo[2.2.1]heptan-7-yl)cyclohexyl group, a 3-(8-aza-bicyclo[3.2.1]octan-8-yl)cyclohexyl group, a 3-(9-aza-bicyclo[3.3.1]nonan-9-yl)cyclohexyl group, a 4-(5-aza-bicyclo[2.1.1]hexan-5-yl)cyclohexyl group, a 4-(6-aza-bicyclo

[3.1.1]heptan-6-yl)cyclohexyl group, a 4-(7-aza-bicyclo [2.2.1]heptan-7-yl)cyclohexyl group, a 4-(8-aza-bicyclo [3.2.1]octan-8-yl)cyclohexyl group, a 4-(9-aza-bicyclo [3.3.1]nonan-9-yl)cyclohexyl group, a 3-(3,3-difluoropyrrolidin-1-yl)propyl group, a 3-(3-fluoropiperidin-1-yl)propyl group, a 3-[(3R)-3-fluoropyrrolidin-1-yl]propyl group, a 3-(4,4-difluoropiperidin-1-yl)propyl group, a 3-(4-fluoropiperidin-1-yl)propyl group, a 3-(3,3-difluoropiperidin-1-yl)propyl group, a 3-[(2S)-2-methylpiperidin-1-yl]propyl group, a 3-[(2R)-2-methylpiperidin-1-yl]propyl group, a 3-(3-methylpiperidin-1-yl)propyl group, a 3-[(3S)-3-methylpiperidin-1-yl]propyl group, a 3-[(3R)-3-methylpiperidin-1-yl]propyl group, a 3-[(4S)-4-methylpiperidin-1-yl]propyl group, a 3-[(4R)-4-methylpiperidin-1-yl]propyl group, a 3-[(2R,5R)-2,5-dimethylpyrrolidin-1-yl]propyl group, a 3-(3-methylpyrrolidin-1-yl)propyl group, a 3-[(2S)-2-methylpyrrolidin-1-yl]propyl group, a 3-[(2R)-2-methylpyrrolidin-1-yl]propyl group, a 3-[(3S)-3-methylpyrrolidin-1-yl]propyl group, a 3-[(3R)-3-methylpyrrolidin-1-yl]propyl group, a 3-[(2-oxopyrrolidin-1-yl)]propyl group, a 3-[(2S)-2-methylpiperidin-1-yl]propyl group, a 3-[(2S)-2-methylazepan-1-yl]propyl group, a 3-[(2R)-2-methylazepan-1-yl]propyl group, a 3-[(3S)-3-methylazepan-1-yl]propyl group, a 3-[(3R)-3-methylazepan-1-yl]propyl group et al. Of those, preferred are a 3-pyrrolidin-1-ylpropyl group, a 3-piperidin-1-ylpropyl group, a 3-[(2S)-2-methylpiperidin-1-yl]propyl group, a 3-[(2R)-2-methylpiperidin-1-yl]propyl group, a 3-[(3S)-3-methylpiperidin-1-yl]propyl group, a 3-[(3R)-3-methylpiperidin-1-yl]propyl group, a 3-[(4S)-4-methylpiperidin-1-yl]propyl group, a 3-[(4R)-4-methylpiperidin-1-yl]propyl group, a 3-[(2S)-2-methylpyrrolidin-1-yl]propyl group, a 3-[(2R)-2-methylpyrrolidin-1-yl]propyl group, a 3-[(3S)-3-methylpyrrolidin-1-yl]propyl group, a 3-[(3R)-3-methylpyrrolidin-1-yl]propyl group, a 3-azepan-1-ylpropyl group, a 3-[(2S)-2-methylazepan-1-yl]propyl group, a 3-[(2R)-2-methylazepan-1-yl]propyl group, a 3-[(3S)-3-methylazepan-1-yl]propyl group, a 3-[(3R)-3-methylazepan-1-yl]propyl group, a 3-azocan-1-ylpropyl group, a 1-propylpiperidin-4-yl group, a 1-isopropylpiperidin-4-yl group, a 1-butylpiperidin-4-yl group, a 1-isobutylpiperidin-4-yl group, a 1-sec-butylpiperidin-4-yl group, a 1-tert-butylpiperidin-4-yl group, a 1-pentylpiperidin-4-yl group, a 1-isoamylpiperidin-4-yl group, a 1-neopentylpiperidin-4-yl group, a 1-cyclopropylpiperidin-4-yl group, a 1-cyclobutylpiperidin-4-yl group, a 1-cyclopentylpiperidin-4-yl group, a 1-cyclohexylpiperidin-4-yl group et al.

$X_1$ represents a carbon atom, a nitrogen atom, a sulfur atom or an oxygen atom, and is preferably an oxygen atom.

Ar represents a divalent group derived from a benzene ring, a pyridine ring, a pyrimidine ring, a pyrazine ring or a pyridazine ring by removing two hydrogen atoms therefrom (the divalent group may be substituted with a halogen atom, a lower alkoxy group (the lower alkoxy group may be substituted with a halogen atom), a lower alkyl group (the lower alkyl group may be substituted with a halogen atom), or a hydroxyl group). Ar is preferably a divalent group derived from a benzene ring or a pyridine ring by removing two hydrogen atoms therefrom.

$X_3$ to $X_6$ are the same or different, each representing —$CR^2$— or a nitrogen atom; however, 3 or more of $X_3$ to $X_6$ are not nitrogen atoms at the same time.

Preferably and recommendably, $X_3$ to $X_6$ are all —$CR^2$—, or any one of them is a nitrogen atom and the remaining three are —$CR^2$—.

Concretely, for example, the following are exemplified as the compounds of the formula (I). In the following, for example, the expression of (2S*,3S*) means (2S,3S) or (2R, 3R); however, since the asymmetric configuration is not determined, it is expressed as (2S*,3S*) for convenience' sake. Similarly, the expression of (2R*,3R*) means (2R,3R) or (2S,3S).

3-phenyl-2-[4-[3-(1-pyrrolidinyl)propoxy]phenyl]-1,4-benzoxathiin, 3-phenyl-2-[4-[3-(1-piperidinyl)propoxy]phenyl]-1,4-benzoxathiin, (2,3-cis)-2,3-dihydro-3-phenyl-2-[4-[3-(1-piperidinyl)propoxy]phenyl]-1,4-benzoxathiin, (2,3-cis)-2,3-dihydro-3-phenyl-2-[4-[3-(1-pyrrolidinyl)propoxy]phenyl]-1,4-benzoxathiin, 3-methyl-2-[4-[3-(1-pyrrolidinyl)propoxy]phenyl]-1,4-benzoxathiin, 3-ethyl-2-[4-[3-(1-pyrrolidinyl)propoxy]phenyl]-1,4-benzoxathiin, (2,3-cis)-2,3-dihydro-3-methyl-2-[4-[3-(1-pyrrolidinyl)propoxy]phenyl]-1,4-benzoxathiin, (2,3-cis)-2,3-dihydro-3-ethyl-2-[4-[3-(1-pyrrolidinyl)propoxy]phenyl]-1,4-benzoxathiin, (2,3-cis)-2,3-dihydro-3-methyl-2-[4-[3-(1-pyrrolidinyl)propoxy]phenyl]-1,4-benzoxathiin-4,4-dioxide, (2,3-cis)-2,3-dihydro-3-ethyl-2-[4-[3-(1-pyrrolidinyl)propoxy]phenyl]-1,4-benzoxathiin-4,4-dioxide, (2,3-trans)-2,3-dihydro-3-methyl-2-[4-[3-(1-pyrrolidinyl)propoxy]phenyl]-1,4-benzoxathiin, (2,3-trans)-2,3-dihydro-3-ethyl-2-[4-[3-(1-pyrrolidinyl)propoxy]phenyl]-1,4-benzoxathiin, (2,3-trans)-2,3-dihydro-4,4-dioxido-3-methyl-2-[4-[3-(1-pyrrolidinyl)propoxy]phenyl]-1,4-benzoxathiin, (2,3-trans)-2,3-dihydro-3-ethyl-2-[4-[3-(1-pyrrolidinyl)propoxy]phenyl]-1,4-benzoxathiin-4,4-dioxide, (2,3-cis)-2,3-dihydro-3-methyl-2-[4-[3-(1-pyrrolidinyl)propoxy]phenyl]-1,4-benzoxathiin-4-oxide, (2,3-cis)-2,3-dihydro-3-ethyl-2-[4-[3-(1-pyrrolidinyl)propoxy]phenyl]-1,4-benzoxathiin-4-oxide, (2,3-cis)-2,3-dihydro-2-methyl-3-[4-[3-(1-pyrrolidinyl)propoxy]phenyl]-1,4-benzoxathiin, (2,3-cis)-2,3-dihydro-2-methyl-3-[4-[3-(1-pyrrolidinyl)propoxy]phenyl]-1,4-benzoxathiin-4,4-dioxide, 2,3-dihydro-2-[4-[3-(1-pyrrolidinyl)propoxy]phenyl]-1,4-benzoxathiin, (2,3-trans)-2,3-dihydro-3-methyl-2-[4-[3-(1-pyrrolidinyl)propoxy]phenyl]-1,4-benzoxathiin-4-oxide, (2,3-trans)-2,3-dihydro-3-ethyl-2-[4-[3-(1-pyrrolidinyl)propoxy]phenyl]-1,4-benzoxathiin-4-oxide, (2,3-trans)-2,3-dihydro-3-ethyl-2-[4-[3-((3S)-3-methyl-1-piperidinyl)propoxy]phenyl]-1,4-benzoxathiin, (2,3-trans)-2,3-dihydro-3-ethyl-2-[4-[(1-cyclobutylpiperidin-4-yl)oxy]phenyl]-1,4-benzoxathiin, (2,3-trans)-2,3-dihydro-3-methyl-2-[4-[3-(1-pyrrolidinyl)propoxy]phenyl]-[1,4]oxathiino[3,2-b]pyridine, (2,3-trans)-2,3-dihydro-3-ethyl-2-[4-[3-((3S)-3-methyl-1-piperidinyl)propoxy]phenyl]-1,4-benzoxathiin-4,4-dioxide, (2,3-trans)-2,3-dihydro-3-ethyl-2-[4-[(1-cyclobutylpiperidin-4-yl)oxy]phenyl]-1,4-benzoxathiin-4,4-dioxide, (2S,3S)-2,3-dihydro-3-methyl-2-[4-[3-(1-pyrrolidinyl)propoxy]phenyl]-1,4-benzoxathiin-4,4-dioxide, (2R,3R)-2,3-dihydro-3-methyl-2-[4-[3-(1-pyrrolidinyl)propoxy]phenyl]-1,4-benzoxathiin-4,4-dioxide, (2,3-trans)-2,3-dihydro-3-methyl-2-[4-[3-(1-pyrrolidinyl)propoxy]phenyl]-[1,4]oxathiino[3,2-b]pyridine-4,4-dioxide, (2,3-trans)-2,3-dihydro-3-methyl-2-[4-[(1-cyclobutylpiperidin-4-yl)oxy]phenyl]-1,4-benzoxathiin-4,4-dioxide, (2,3-trans)-2,3-dihydro-3-methyl-2-[4-[3-((3S)-3-methyl-1-piperidinyl)propoxy]phenyl]-1,4-benzoxathiin-4,4-dioxide, (2,3-trans)-2,3-dihydro-8-methoxy-3-methyl-2-[4-[(1-cyclobutylpiperidin-4-yl)oxy]phenyl]-1,4-benzoxathiin-4,4-dioxide, 1-[3-[4-[(2,3-trans)-2,3-dihydro-4,4-dioxido-8-methoxy-3-methyl-1,4-benzoxathiin-2-yl]phenoxy]propyl]-(3S)-3-methylpiperidine, 1-[3-[4-[(2,3-trans)-2,3-dihydro-4,4-dioxido-8-methoxy-3-methyl-1,4-benzoxathiin-2-yl]phenoxy]propyl]-pyrrolidine, 1-[3-[4-[(2,3-trans)-2,3-dihydro-4,4-dioxido-8-methoxy-3-methyl-1,4-benzoxathiin-2-yl]phenoxy]propyl]-piperidine, 1-[3-[4-[(2,3-trans)-2,3-dihydro-4,4-dioxido-5-methoxy-3-methyl-1,4-benzoxathiin-2-yl]phenoxy]propyl]-pyrrolidine, 1-[3-[4-[(2,3-trans)-2,3-dihydro-4,4-dioxido-5-methoxy-3-methyl-1,4-benzoxathiin-2-yl]phenoxy]propyl]-piperidine, 1-[3-[5-[(2,3-trans)-2,3-dihydro-4,4-dioxido-3-methyl-1,4-benzoxathiin-2-yl]pyridin-2-yloxy]propyl-pyrrolidine, 1-[3-[4-[(2,3-trans)-2,3-dihydro-4,4-dioxido-6-methoxy-3-methyl-1,4-benzoxathiin-2-yl]phenoxy]propyl]-pyrrolidine, 1-[3-[4-[(2,3-trans)-2,3-dihydro-4,4-dioxido-6-methoxy-3-methyl-1,4-benzoxathiin-2-yl]phenoxy]propyl]-piperidine, 1-[3-[4-[(2S,3S)-2,3-dihydro-4,4-dioxido-8-methoxy-3-methyl-1,4-benzoxathiin-2-yl]phenoxy]propyl]-pyrrolidine, 1-[3-[4-[(2R,3R)-2,3-dihydro-4,4-dioxido-8-methoxy-3-methyl-1,4-benzoxathiin-2-yl]phenoxy]propyl]-pyrrolidine, (2S,3S)-2,3-dihydro-8-methoxy-3-methyl-2-[4-[(1-cyclobutylpiperidin-4-yl)oxy]phenyl]-1,4-benzoxathiin-4,4-dioxide, (2R,3R)-2,3-dihydro-8-methoxy-3-methyl-2-[4-[(1-cyclobutylpiperidin-4-yl)oxy]phenyl]-1,4-benzoxathiin-4,4-dioxide, 1-[3-[4-[(2,3-trans)-2,3-dihydro-4,4-dioxido-7-methoxy-3-methyl-1,4-benzoxathiin-2-yl]phenoxy]propyl]-pyrrolidine, 1-[3-[4-[(2,3-trans)-2,3-dihydro-4,4-dioxido-7-methoxy-3-methyl-1,4-benzoxathiin-2-yl]phenoxy]propyl]-piperidine, 1-[3-[4-[(2,3-trans)-2,3-dihydro-4,4-dioxido-3-methyl-[1,4]oxathiino[3,2-b]pyridin-2-yl]phenoxy]propyl]-piperidine, (2,3-trans)-2,3-dihydro-5-methoxy-3-methyl-2-[4-[(1-cyclobutylpiperidin-4-yl)oxy]phenyl]-1,4-benzoxathiin-4,4-dioxide, (2S,3S)-2,3-dihydro-5-methoxy-3-methyl-2-[4-[(1-cyclobutylpiperidin-4-yl)oxy]phenyl]-1,4-benzoxathiin-4,4-dioxide, (2R,3R)-2,3-dihydro-5-methoxy-3-methyl-2-[4-[(1-cyclobutylpiperidin-4-yl)oxy]phenyl]-1,4-benzoxathiin-4,4-dioxide, (2S,3S)-2,3-dihydro-3-methyl-2-[4-[3-(1-pyrrolidinyl)propoxy]phenyl]-[1,4]oxathiino[3,2-b]pyridin-4,4-dioxide, (2R,3R)-2,3-dihydro-3-methyl-2-[4-[3-(1-pyrrolidinyl)propoxy]phenyl]-[1,4]oxathiino[3,2-b]pyridin-4,4-dioxide, 1-[3-[4-[(2S,3S)-2,3-dihydro-4,4-dioxido-5-methoxy-3-methyl-1,4-benzoxathiin-2-yl]phenoxy]propyl]-piperidine, 1-[3-[4-[(2R,3R)-2,3-dihydro-4,4-dioxido-5-methoxy-3-methyl-1,4-benzoxathiin-2-yl]phenoxy]propyl]-piperidine, (2R,3R)-2-{4-[(1-cyclobutylpiperidin-4-yl)oxy]phenyl}-3-methyl-2,3-dihydro[1,4]oxathiino[3,2-b]pyridine 4,4-dioxide, (2S,3S)-2-{4-[(1-cyclobutylpiperidin-4-yl)oxy]phenyl}-3-methyl-2,3-dihydro[1,4]oxathiino[3,2-b]pyridine 4,4-dioxide, 1-[3-[4-[(2S,3S)-2,3-dihydro-4,4-dioxido-3-methyl-[1,4]oxathiino[3,2-b]pyridin-2-yl]phenoxy]propyl]-piperidine, 1-[3-[4-[(2R,3R)-2,3-dihydro-4,4-dioxido-3-methyl-[1,4]oxathiino[3,2-b]pyridin-2-yl]phenoxy]propyl]-piperidine, (2S,3S)-3-methyl-2-(4-{3-[(2R)-2-methylpyrrolidin-1-yl]propoxy}phenyl)-2,3-dihydro[1,4]oxathiino[3,2-b]pyridine 4,4-dioxide, (2R,3R)-3-methyl-2-(4-{3-[(2R)-2-methylpyrrolidin-1-yl]propoxy}phenyl)-2,3-dihydro[1,4]oxathiino[3,2-b]pyridine 4,4-dioxide, (2S,3S)-2-{4-[(1-isopropylpiperidin-4-yl)oxy]phenyl}-3-methyl-2,3-dihydro[1,4]oxathiino[3,2-b]pyridine 4,4-dioxide, (2R,3R)-2-{4-[(1-isopropylpiperidin-4-yl)oxy]phenyl}-3-methyl-2,3-dihydro[1,4]oxathiino[3,2-b]pyridine 4,4-dioxide, (2S*,3S*)-2-[3-bromo-4-(3-pyrrolidin-1-ylpropoxy)phenyl]-3-methyl-2,3-dihydro[1,4]oxathiino[3,2-b]pyridine 4,4-dioxide, 1-(3-{2-bromo-4-[(2S*,3S*)-8-methoxy-3-methyl-4,4-dioxido-2,3-dihydro-1,4-benzoxathiin-2-yl]phenoxy}propyl)pyrrolidine, 1-{3-[4-(3-methyl-4,4-dioxido-1,4-benzoxathiin-2-yl)phenoxy]propyl]pyrrolidine, 1-{2-[4-(3-phenyl-1,4-benzoxathiin-2-yl)phenoxy]ethyl}pyrrolidine, 1-(2-{4-[(2,3-cis)-3-phenyl-2,3-dihydro-1,4-benzoxathiin-2-yl]phenoxy}ethyl)pyrrolidine, 1-{2-[4-(3-phenyl-1,4-benzoxathiin-2-yl)phenoxy]ethyl}piperidine, or 1-(2-{4-[(2,3-cis)-3-phenyl-2,3-dihydro-1,4-benzoxathiin-2-yl]phenoxy}ethyl)piperidine et al.

Above all, recommended are 1-[3-[4-[(2S,3S)-2,3-dihydro-4,4-dioxido-8-methoxy-3-methyl-1,4-benzoxathiin-2-yl]phenoxy]propyl]-pyrrolidine or 1-[3-[4-[(2R,3R)-2,3-dihydro-4,4-dioxido-8-methoxy-3-methyl-1,4-benzoxathiin-2-yl]phenoxy]propyl]-pyrrolidine, (2R,3R)-2,3-dihydro-8-methoxy-3-methyl-2-[4-[(1-cyclobutylpiperidin-4-yl)oxy]phenyl]-1,4-benzoxathiin-4,4-dioxide or (2S,3S)-2,3-dihydro-8-methoxy-3-methyl-2-[4-[(1-cyclobutylpiperidin-4-yl)oxy]phenyl]-1,4-benzoxathiin-4,4-dioxide, (2S,3S)-2,3-dihydro-3-methyl-2-[4-[3-(1-pyrrolidinyl)propoxy]phenyl]-[1,4]oxathiino[3,2-b]pyridine-4,4-dioxide or (2R,3R)-2,3-dihydro-3-methyl-2-[4-[3-(1-pyrrolidinyl)propoxy]phenyl]-[1,4]oxathiino[3,2-b]pyridine-4,4-dioxide, (2R,3R)-2-{4-[(1-cyclobutylpiperidin-4-yl)oxy]phenyl}-3-methyl-2,3-dihydro[1,4]oxathiino[3,2-b]pyridine 4,4-dioxide or (2S,3S)-2-{4-[(1-cyclobutylpiperidin-4-yl)oxy]phenyl}-3-methyl-2,3-dihydro[1,4]oxathiino[3,2-b]pyridine 4,4-dioxide, (2S,3S)-3-methyl-2-(4-{3-[(2R)-2-methylpyrrolidin-1-yl]propoxy}phenyl)-2,3-dihydro[1,4]oxathiino[3,2-b]pyridine 4,4-dioxide or (2R,3R)-3-methyl-2-(4-{3-[(2R)-2-methylpyrrolidin-1-yl]propoxy}phenyl)-2,3-dihydro[1,4]oxathiino[3,2-b]pyridine 4,4-dioxide et al.

Compounds (I-1) or compound (I-1-1) of the invention may be produced, for example, according to the following methods.

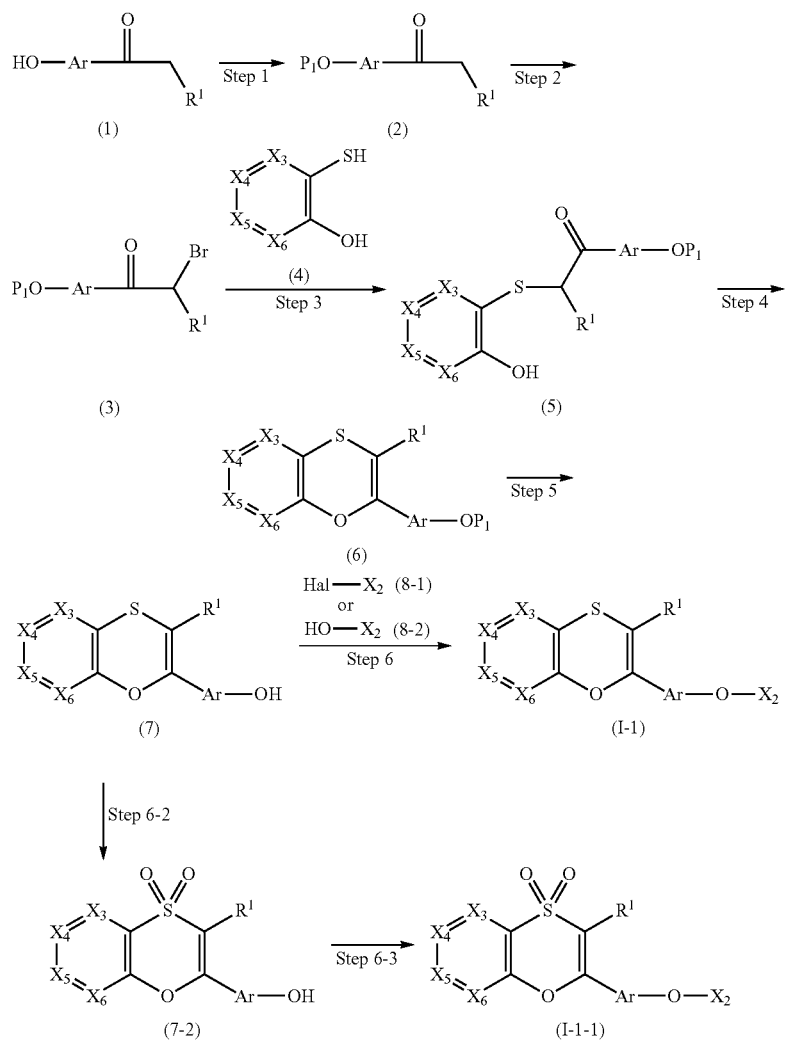

[In the formula, $P_1$ represents a protective group for a hydroxyl group; Hal represents a halogen atom; and the other symbols are the same as above.]

(Step 1)

This step is a method for producing a compound (2) by introducing a protective group into the hydroxyl group of a compound (1). The introduction of the hydroxyl-protective group may be attained according to a method described in literature (for example, Protective Groups in Organic Synthesis), or according to a method similar to it, or according to a combination of the method and an ordinary method.

The compound (1) for use in this step includes, for example, 4'-hydroxypropiophenone, 4'-hydroxybutyrophenone, 1-(4-hydroxyphenyl)-2-phenylethanone et al.

Concretely as the method of introducing a protective group to the hydroxyl group of the compound (1), for example, the compound (1) is reacted with generally from 1 equivalent to 1.5 equivalents, preferably from 1 to 1.2 equivalents, relative to 1 equivalent of compound (1), of NaH, and with generally from 1 to 2 equivalent, preferably from 1 to 1.5 equivalents, relative to 1 equivalent of compound (1), of triisopropylsilyl chloride, thereby obtaining a compound in which the hydroxy group is protected with a triisopropyl group.

Not specifically defined, the reaction solvent may be any one not interfering with the reaction, including, for example, N,N-dimethylformamide (hereinafter abbreviated as "DMF"), tetrahydrofuran (hereinafter abbreviated as "THF"), 1,4-dioxane, chloroform, dichloromethane et al. Of those, preferred are DMF, THF et al.

The reaction temperature may be generally from −20° C. to 40° C., preferably from 0° C. to 30° C.

The reaction time may be generally from 1 to 24 hours, preferably from 1 to 8 hours.

The compound (2) thus obtained may be subjected to the next step, after isolated and purified in any known manner for separation and purification, for example, through concentration under reduced pressure, crystallization, solvent extraction, reprecipitation, chromatography, or not after isolated and purified. (The same shall apply to the following steps.)

(Step 2)

This step is a method for producing a compound (3) by reacting the compound (2) obtained in the above step 1 with bromine.

Bromine to be used in this step may be generally from 0.8 equivalents to 1.2 equivalents relative to 1 equivalent of the compound (2), preferably from 0.9 equivalents to 1.1 equivalents.

Not specifically defined, the reaction solvent may be any one not interfering with the reaction, including, for example, dichloromethane, chloroform, 1,2-dichloroethane, acetic acid et al. Of those, preferred are dichloromethane, chloroform.

The reaction temperature may be generally from −30° C. to 80° C., preferably from 0° C. to 40° C.

The reaction time may be generally from 1 to 24 hours, preferably from 1 to 6 hours.

The compound (3) thus obtained may be subjected to the next step, after isolated and purified in any known manner for separation and purification, for example, through concentration under reduced pressure, crystallization, solvent extraction, reprecipitation, chromatography, or not after isolated and purified.

(Step 3)

This step is a method for producing a compound (5) by reacting the compound (3) obtained in the above step 2 with a compound (4) in the presence of a base.

The base to be used in this step includes, for example, N,N-diisopropylethylamine, triethylamine, potassium carbonate, sodium carbonate, cesium carbonate et al.

The amount of the base may be generally from 1 to 5 equivalents relative to 1 equivalent of the compound (4), preferably from 1 to 2 equivalents.

Not specifically defined, the reaction solvent may be any one not interfering with the reaction, including, for example, DMF, THF, 1,4-dioxane, dimethyl sulfoxide, chloroform, methylene chloride, ethyl acetate, acetonitrile, methanol, ethanol et al. Of those, preferred are DMF, THF et al.

The reaction temperature may be generally from −78° C. to 60° C., preferably from −30° C. to 40° C.

The reaction time may be generally from 1 to 24 hours, preferably from 1 to 3 hours.

The compound (5) thus obtained may be subjected to the next step, after isolated and purified in any known manner for separation and purification, for example, through concentration under reduced pressure, crystallization, solvent extraction, reprecipitation, chromatography, or not after isolated and purified.

(Step 4)

This step is a method for producing a compound (6) by processing the compound (5) obtained in the above step 3 with an acid.

The acid to be used in this step includes, for example, p-toluenesulfonic acid, Amberlyst 15 (by Aldrich) et al.

The amount of the acid may be generally from 0.05 to 0.5 equivalents relative to 1 equivalent of the compound (5), preferably from 0.1 to 0.3 equivalents.

Not specifically defined, the reaction solvent may be any one not interfering with the reaction, including, for example, toluene, benzene, chloroform et al. Of those, preferred is toluene.

The reaction temperature may be generally from 20 to 200° C., preferably from 80 to 150° C.

The reaction time may be generally from 1 to 24 hours, preferably from 1 to 5 hours.

The compound (6) thus obtained may be subjected to the next step, after isolated and purified in any known manner for separation and purification, for example, through concentration under reduced pressure, crystallization, solvent extraction, reprecipitation, chromatography, or not after isolated and purified.

(Step 5)

This step is a method for producing a compound (7) by removing the hydroxyl-protective group of the compound (6) obtained in the above step 4.

The removal of the hydroxyl-protective group may be attained according to the method described in the above-mentioned Protective Groups in Organic Synthesis, or according to a method similar to it, or according to a combination of the method with an ordinary method.

For example, when the hydroxyl-protective group is a tri-isopropylsilyl group, the compound (6) is reacted with generally from 1 to 2 equivalents, preferably from 1 to 1.2 equivalents, relative to 1 equivalent of the compound (6), of tetrabutylammonium fluoride, thereby removing the hydroxyl-protective group.

In the removal of the protective group, an acid may be present in the reaction system, in an amount of generally from 1 to 5 equivalents relative to 1 equivalent of the compound (6), preferably from 1 to 1.5 equivalents.

The acid may be, for example, acetic acid.

The compound (7) thus obtained may be subjected to the next step, after isolated and purified in any known manner for separation and purification, for example, through concentration under reduced pressure, crystallization, solvent extraction, reprecipitation, chromatography, or not after isolated and purified.

(Step 6)

This step includes a step 6a and a step 6b.

(Step 6a)

This step is a method for producing a compound (I-1) of the invention by reacting the compound (7) obtained in the above step 5 with a compound (8-1) in the presence of a base.

The base to be used in this step includes, for example, potassium carbonate, cesium carbonate, sodium carbonate et al.

The amount of the base may be generally from 1 to 5 equivalents relative to 1 equivalent of the compound (7), preferably from 1 to 3 equivalents.

The compound (8-1) for use in this step includes, for example, 1-(3-bromopropyl)piperidine, 1-(3-bromopropyl) pyrrolidine et al.

The amount of the compound (8-1) may be generally from 1 to 5 equivalents relative to 1 equivalent of the compound (7), preferably from 1 to 2 equivalents.

Not specifically defined, the reaction solvent may be any one not interfering with the reaction, including, for example, DMF, THF, 1,4-dioxane, dimethyl sulfoxide, chloroform, ethyl acetate, acetonitrile et al. Of those, preferred are DMF, THF, dimethyl sulfoxide.

The reaction temperature may be generally from 0° C. to 150° C., preferably from 0° C. to 100° C.

The reaction time may be generally from 0.5 to 5 hours, preferably from 0.5 to 2 hours.

(Step 6B)

This step is a method for producing a compound (I-1) of the invention by reacting the compound (7) obtained in the above step 5 with a compound (8-2).

The reaction of the compound (7) with a compound (8-2) is so-called Mitsunobu reaction. The Mitsunobu reaction may be attained according to a method described in literature (for example, Mitsunobu. O., "The use of diethyl azodicarboxylate and triphenylphosphine in synthesis and transformation of natural products" Synthesis, Vol. 1, 1981, pp. 1-28) in the presence of a phosphine compound and an azo compound, or according a method similar to it, or according to a combination of the method with an ordinary method.

The amount of the compound (8-2) to be used may be generally from 0.5 to 10 equivalents relative to 1 equivalent of the compound (7), preferably from 1 to 3 equivalents.

The compound (8-2) for use in this step includes, for example, 1-(3-hydroxypropyl)pyrrolidine, 1-(3-hydroxypropyl)piperidine et al.

The phosphine compound for use herein includes triphenyl phosphine, tri-n-butyl phosphine et al. The amount of the phosphine compound to be used may be generally from 1 to 10 equivalents relative to 1 equivalent of the compound (8-2), preferably from 1 to 3 equivalents.

The azo compound to be used includes, for example, diethyl azodicarboxylate, diisopropyl azodicarboxylate, 1,1-(azodicarbonyl)dipiperidine et al. The amount of the azo compound to be used may be generally from 1 to 10 equivalents relative to 1 equivalent of the compound (8-2), preferably from 1 to 3 equivalents.

The reaction time may be generally from 1 to 48 hours, preferably from 4 to 12 hours. The reaction temperature may be generally from room temperature to the boiling temperature of the reaction solvent, preferably from 15° C. to 30° C.

Not specifically defined, the reaction solvent may be any one not interfering with the reaction, including THF, toluene et al.

(Step 6-2)

This step is for converting the compound (7) into a sulfone compound (7-2). To this step, applicable is the same method as that for the (step 11-1) to be mentioned hereinunder.

(Step 6-3)

This step is a method for producing a compound (I-1-1) starting from a compound (7-2). This reaction may be attained according to (step 6), and the reaction condition and others described for (step 6) are applicable to it.

The compound (I-1) and the compound (I-1-1) thus obtained may be isolated and purified in a known separation and purification method of, for example, concentration under reduced pressure, crystallization, solvent extraction, reprecipitation, chromatography.

Compounds (I-2) of the invention may be produced, for example, according to the following method.

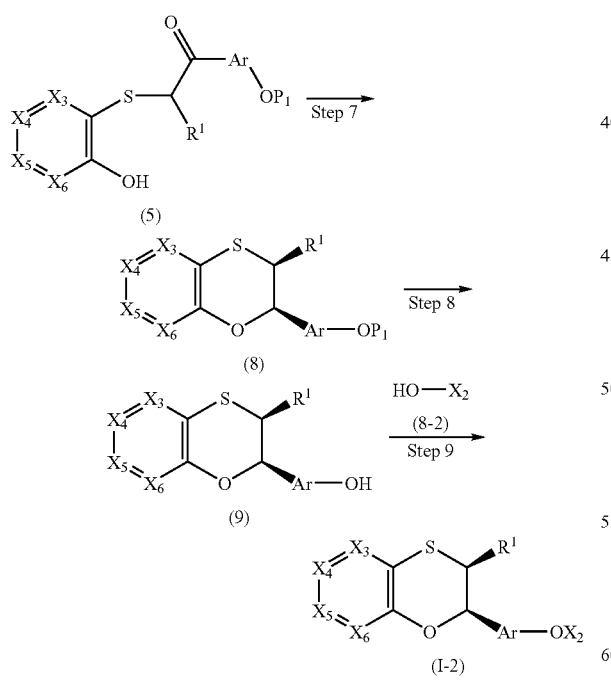

[In the formula, the symbols are the same as above.]

(Step 7)

This step is a method for producing a compound (8) by reacting the compound (5) obtained in the above step 3 with trifluoroacetic acid and triethylsilane.

The amount of trifluoroacetic acid to be used in this step may be generally from 5 to 20 equivalents relative to 1 equivalent of the compound (5), preferably from 7 to 15 equivalents.

The amount of triethylsilane to be used in this step may be generally from 1 to 8 equivalents relative to 1 equivalent of the compound (5), preferably from 3 to 6 equivalents.

Not specifically defined, the reaction solvent may be any one not interfering with the reaction, including, for example, dichloromethane, chloroform, toluene, THF, 1,4-dioxane et al. Of those, preferred are dichloromethane, chloroform.

The reaction temperature may be generally from −78° C. to 30° C., preferably from −10° C. to 10° C.

The reaction time may be generally from 1 to 24 hours, preferably from 1 to 12 hours.

The compound (8) thus obtained may be subjected to the next step, after isolated and purified in any known manner for separation and purification, for example, through concentration under reduced pressure, crystallization, solvent extraction, reprecipitation, chromatography, or not after isolated and purified.

(Step 8)

This step is a method for producing a compound (9) by removing the hydroxyl-protective group of the compound (8) obtained in the above step 7.

The removal of the hydroxyl-protective group may be attained according to the same method as that for the above step 5, or according to a method similar to it, or according to a combination of the method with an ordinary method.

The compound (9) thus obtained may be subjected to the next step, after isolated and purified in any known manner for separation and purification, for example, through concentration under reduced pressure, crystallization, solvent extraction, reprecipitation, chromatography, or not after isolated and purified.

(Step 9)

This step is a method for producing a compound (I-2) of the invention by reacting the compound (9) obtained in the above step 8 with the above-mentioned compound (8-2).

The reaction in this step may be attained according to the same method as that for the above step 6b, or according to a method similar to it, or according to a combination of the method with an ordinary method.

The compound (I-2) thus obtained may be isolated and purified in any known manner for separation and purification, for example, through concentration under reduced pressure, crystallization, solvent extraction, reprecipitation, chromatography.

Compounds (I-2-1) of the invention may be produced, for example, according to the following method.

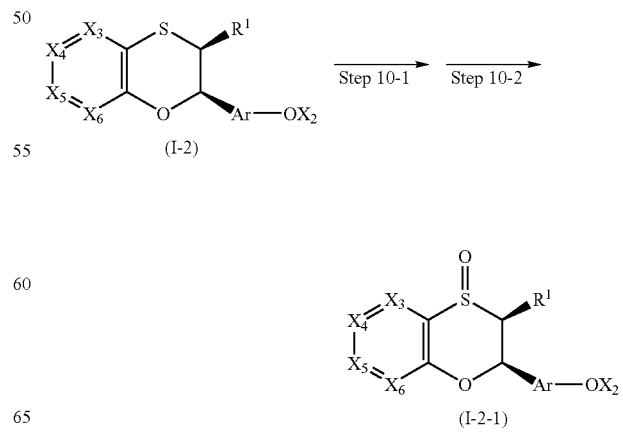

[In the formula, the symbols are the same as above.]
(Step 10)

This step is a method for producing a compound (I-2-1) by reacting the compound (I-2) obtained in the above step 9 with m-chloroperbenzoic acid (hereinafter referred to as "mCPBA") (step 10-1), and then selectively reducing the resulting tertiary amine-N-oxide with an aqueous saturated sodium hydrogensulfite solution (step 10-2).
(Step 10-1)

The amount of mCPBA to be used in this step may be generally from 1.5 to 2.1 equivalents relative to 1 equivalent of the compound (1-2), preferably from 1.7 to 2 equivalents.

Not specifically defined, the reaction solvent may be any one not interfering with the reaction, including, for example, dichloromethane, chloroform, 1,2-dichloroethane et al. Of those, preferred are dichloromethane, chloroform.

The reaction temperature may be generally from −78° C. to 40° C., preferably from 0° C. to 10° C.

The reaction time may be generally from 5 minutes to 24 hours, preferably from 30 minutes to 2 hours.
(Step 10-2)

The amount of the aqueous saturated sodium hydrogensulfite solution to be used in this step may be generally from 1 equivalent to an excessive amount relative to 1 equivalent of the compound (I-2).

The reaction temperature may be generally from −78° C. to 40° C., preferably from 0° C. to 30° C.

The reaction time may be generally from 5 minutes to 48 hours, preferably from 30 minutes to 24 hours.

In this step, an aqueous saturated sodium hydrogencarbonate solution may be present in the reaction liquid, in an amount of generally from 1 equivalent to an excessive amount relative to 1 equivalent of the compound (I-2).

The compound (I-2-1) thus obtained may be isolated and purified in any known manner for separation and purification, for example, through concentration under reduced pressure, crystallization, solvent extraction, reprecipitation, chromatography.

Compounds (I-2-2) of the invention may be produced, for example, according to the following method.

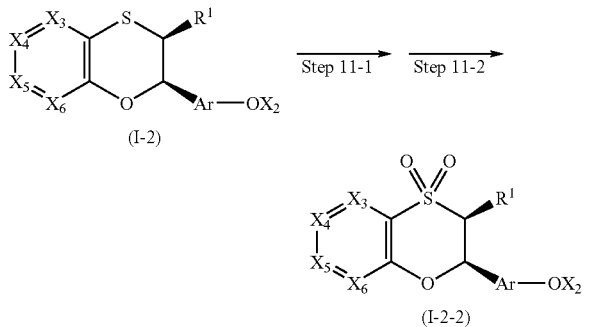

[In the formula, the symbols are the same as above.]
(Step 11)

This step is a method for producing a compound (I-2-2) by reacting the compound (I-2) obtained in the above step 9 with mCPBA (step 11-1), and then selectively reducing the resulting tertiary amine-N-oxide with an aqueous saturated sodium hydrogensulfite solution (step 11-2).
(Step 11-1)

The amount of mCPBA to be used in this step may be generally from 3 to 7 equivalents relative to 1 equivalent of the compound (I-1), preferably from 3.5 to 6 equivalents.

Not specifically defined, the reaction solvent may be any one not interfering with the reaction, including, for example, dichloromethane, chloroform, 1,2-dichloroethane et al. Of those, preferred are dichloromethane, chloroform.

The reaction time may be generally from 10 minutes to 24 hours, preferably from 30 minutes to 2 hours.

The reaction temperature may be generally from −78° C. to 40° C., preferably from 0° C. to 30° C.
(Step 11-2)

The amount of the aqueous saturated sodium hydrogensulfite solution to be used in this step may be generally from 1 equivalent to an excessive amount relative to 1 equivalent of the compound (1-2).

The reaction temperature may be generally from −78° C. to 40° C., preferably from 0° C. to 30° C.

The reaction time may be generally from 5 minutes to 48 hours, preferably from 30 minutes to 24 hours.

In this step, an aqueous saturated sodium hydrogencarbonate solution may be present in the reaction liquid, in an amount of generally from 1 equivalent to an excessive amount relative to 1 equivalent of the compound (I-2).

The compound (I-2-2) thus obtained may be isolated and purified in any known manner for separation and purification, for example, through concentration under reduced pressure, crystallization, solvent extraction, reprecipitation, chromatography.

Compounds (I-3) or compounds (I-3-1) of the invention may be produced according to the following method.

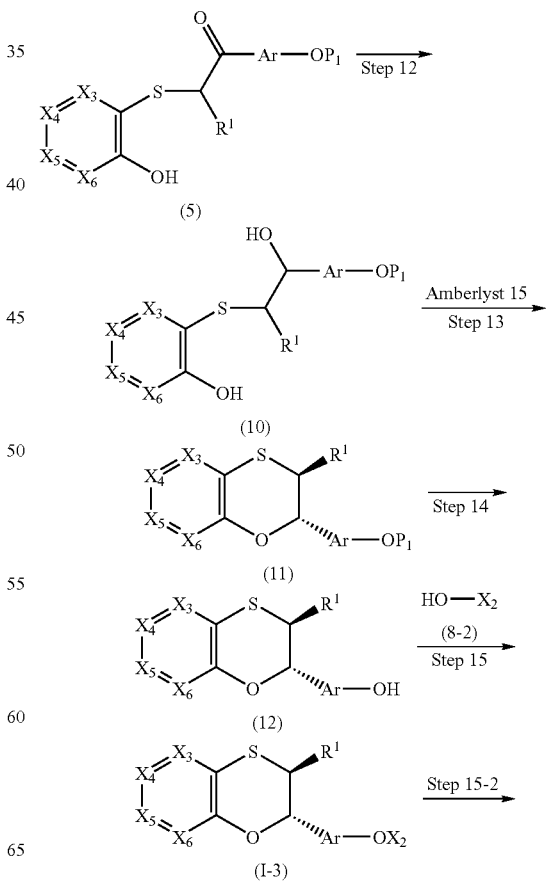

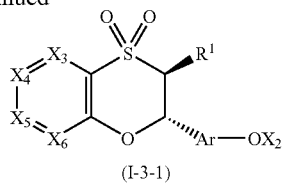

(I-3-1)

[In the formula, the symbols are the same as above.]
(Step 12)

This step is a method for producing a compound (10) by reacting the compound (5) obtained in the above step 3 with a reducing agent.

The reducing agent to be used in this step includes, for example, sodium borohydride, lithium borohydride et al.

The amount of the reducing agent may be generally from 1 to 5 equivalents relative to 1 equivalent of the compound (5), preferably from 1 to 2 equivalents.

Not specifically defined, the reaction solvent may be any one not interfering with the reaction, including, for example, methanol, ethanol, THF, 1,4-dioxane, chloroform et al. Of those, preferred are methanol, ethanol.

The reaction temperature may be generally from −78° C. to 40° C., preferably from 0° C. to 25° C.

The reaction time may be generally from 10 minutes to 24 hours, preferably from 30 minutes to 1 hour.
(Step 13)

This step is a method for producing a compound (11) by reacting the compound (10) obtained in the above step 12 with an ion-exchange resin for acid catalyst, Amberlyst 15 (by Aldrich).

The amount of Amberlyst 15 to be used in this step may be generally from 10 to 200% by weight relative to the weight of the compound (10), preferably from 20 to 70% by weight.

Not specifically defined, the reaction solvent may be any one not interfering with the reaction, including, for example, toluene, benzene et al. Of those, preferred is toluene.

The reaction temperature may be generally from 0° C. to 100° C., preferably from 20 to 50° C.

The reaction time may be generally from 1 to 48 hours, preferably from 1 to 24 hours.

The compound (11) thus obtained may be subjected to the next step, after isolated and purified in any known manner for separation and purification, for example, through concentration under reduced pressure, crystallization, solvent extraction, reprecipitation, chromatography, or not after isolated and purified.
(Step 14)

This step is a method for producing a compound (12) by removing the hydroxyl-protective group from the compound (11) obtained in the above step 13.

The reaction in this step may be attained according the same method as in the above step 5 or 8, or according to a method similar to it, or according to a method similar to those methods.

The compound (12) thus obtained may be subjected to the next step, after isolated and purified in any known manner for separation and purification, for example, through concentration under reduced pressure, crystallization, solvent extraction, reprecipitation, chromatography, or not after isolated and purified.
(Step 15)

This step is a method for producing a compound (I-3) of the invention by reacting the compound (12) obtained in the above step 14 with the above-mentioned compound (8-2).

The reaction in this step is so-called Mitsunobu reaction, and this may be attained according to the same method as in the above step 6b, or according to a method similar to it, or according to a combination of the method with an ordinary method.
(Step 15-2)

This step is a method for producing a compound (I-3-1) of the invention by oxidizing the compound (I-3) with hydrogen peroxide in the presence of sodium tungstate and acetic acid.

The amount of sodium tungstate to be used may be generally from 0.01 to 1 equivalent relative to 1 equivalent of the compound (I-3), preferably from 0.05 to 0.5 equivalent.

The amount of hydrogen peroxide to be used may be generally from 2 to 100 equivalents relative to 1 equivalent of the compound (I-3), preferably from 10 to 50 equivalents.

The amount of acetic acid to be used may be from 1 equivalent to an excessive amount relative to 1 equivalent of the compound (I-3).

The reaction temperature may be generally from 0 to 80° C., preferably from 10 to 50° C.

The reaction time may be generally from 3 to 48 hours, preferably from 6 to 24 hours.

This step may also be attained according to (step 11-1) and (step 11-2).

The compound (I-3) of the compound (I-3-1) thus obtained may be isolated and purified in any known manner for separation and purification, for example, through concentration under reduced pressure, crystallization, solvent extraction, reprecipitation, chromatography.

Compounds (I-4) or compounds (I-4-1) of the invention may be produced, for example, according to the following method.

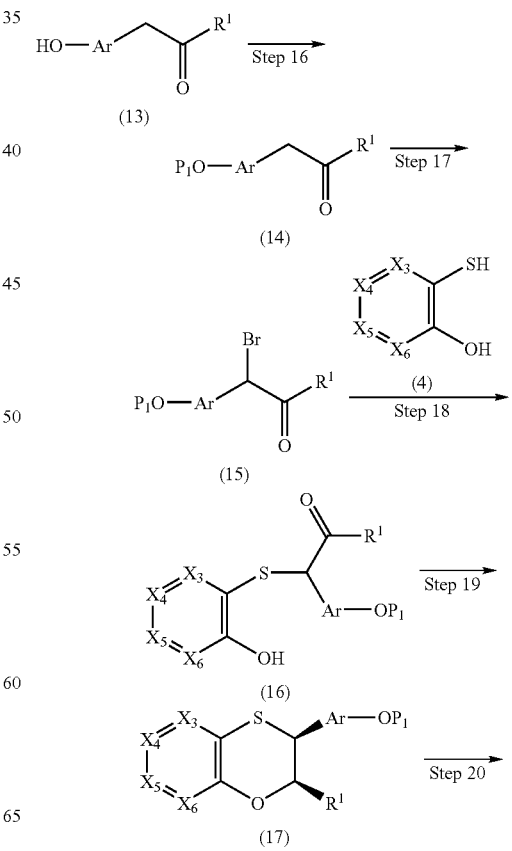

-continued

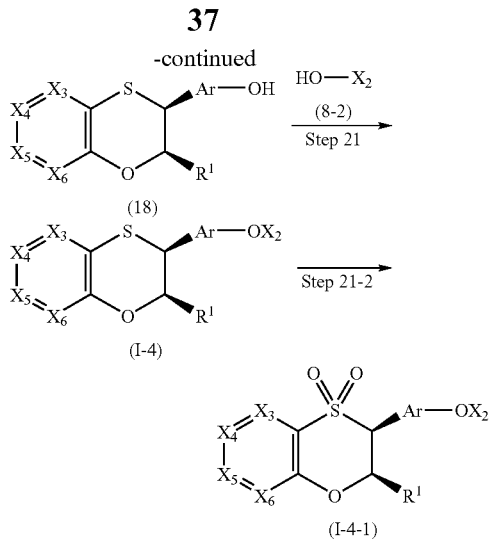

[In the formula, the symbols are the same as above.]

(Step 16)

This step is a method for producing a compound (14) by introducing a protective group into the hydroxyl group of the compound (13).

The hydroxyl-protective group P₁ is, for example, a triisopropylsilyl group et al.

The reaction in this step may be attained according to the same method as in the above step 1, or according to a method similar to it, or according to a combination of the method with an ordinary method.

The compound (14) thus obtained may be subjected to the next step, after isolated and purified in any known manner for separation and purification, for example, through concentration under reduced pressure, crystallization, solvent extraction, reprecipitation, chromatography, or not after isolated and purified.

(Step 17)

This step is a method for producing a compound (15) by reacting the compound (14) obtained in the above step 16 with bromine. The reaction in this step may be attained according to the same method as in the above step 2, or according to a method similar to it, or according to a combination of the method with an ordinary method.

The compound (15) thus obtained may be subjected to the next step, after isolated and purified in any known manner for separation and purification, for example, through concentration under reduced pressure, crystallization, solvent extraction, reprecipitation, chromatography, or not after isolated and purified.

(Step 18)

This step is a method for producing a compound (16) by reacting the compound (15) obtained in the above step 17 with a compound (4). The reaction in this step may be attained according to the same method as in the above step 3, or according to a method similar to it, or according to a combination of the method with an ordinary method. The compound (16) thus obtained may be subjected to the next step, after isolated and purified in any known manner for separation and purification, for example, through concentration under reduced pressure, crystallization, solvent extraction, reprecipitation, chromatography, or not after isolated and purified.

(Step 19)

This step is a method for producing a compound (17) by reacting the compound (16) obtained in the above step 18 with triethylsilane and trifluoroacetic acid. The reaction in this step may be attained according to the same method as in the above step 7, or according to a method similar to it, or according to a combination of the method with an ordinary method. The compound (17) thus obtained may be subjected to the next step, after isolated and purified in any known manner for separation and purification, for example, through concentration under reduced pressure, crystallization, solvent extraction, reprecipitation, chromatography, or not after isolated and purified.

(Step 20)

This step is a method for producing a compound (18) by removing the hydroxyl-protective group from the compound (17) obtained in the step 19. The reaction in this step may be attained according to the same method as in the above step 5 or 8, or according to a method similar to it, or according to a combination of the method with an ordinary method.

The compound (18) thus obtained may be subjected to the next step, after isolated and purified in any known manner for separation and purification, for example, through concentration under reduced pressure, crystallization, solvent extraction, reprecipitation, chromatography, or not after isolated and purified.

(Step 21)

This step is a method for producing a compound (1-4) of the invention by reacting the compound (18) obtained in the above step 20 with a compound (8-2). The reaction in this step may be attained according to the same method as in the above step 6b, or according to a method similar to it, or according to a combination of the method with an ordinary method.

(Step 21-2)

This step is a method for producing a compound (I-4-1) from the compound (I-4). This step may be attained according to (step 11-1) and (step 11-2).

The compound (I-4) or (I-4-1) thus obtained may be isolated and purified in any known manner for separation and purification, for example, through concentration under reduced pressure, crystallization, solvent extraction, reprecipitation, chromatography.

Optically-active compounds (I-5) or optically-active compounds (I-5-1) of the invention are enantiomers of racemates (I-3) or racemates (I-3-1), respectively, and they may be produced according to the following method.

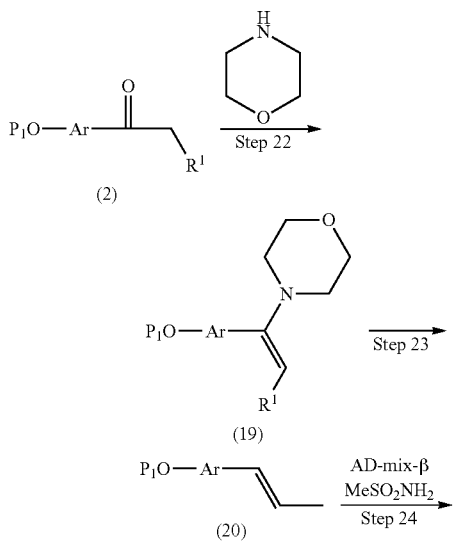

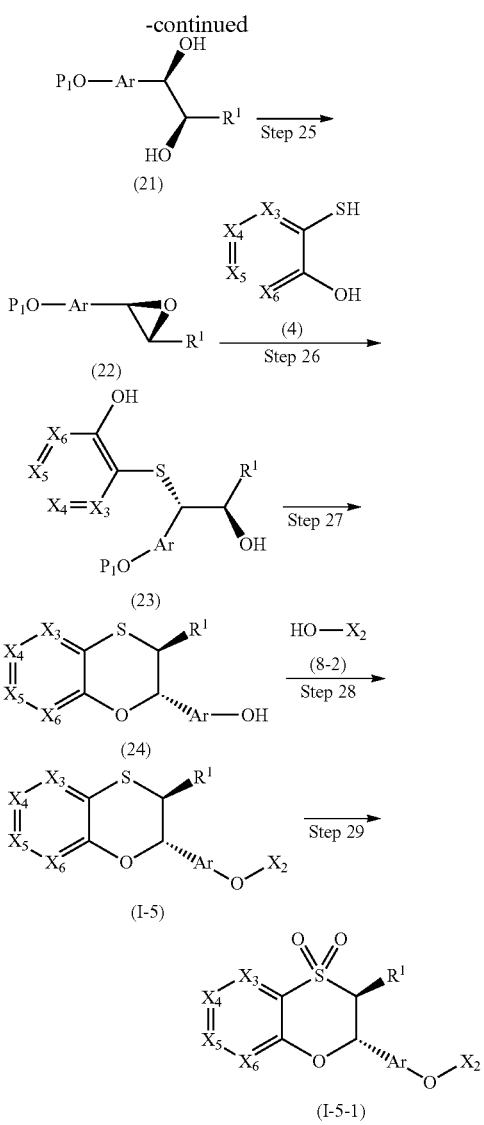

[In the formula, the symbols are the same as above.]

(Step 22)

This step is a method for producing a compound (19) by reacting a compound (2) with morpholine in the presence of titanium tetrachloride.

The amount of titanium tetrachloride to be used may be from 0.3 to 2 equivalents relative to 1 equivalent of the compound (2), preferably from 0.5 to 1 equivalent.

The amount of morpholine to be used may be from 1 to 50 equivalents relative to 1 equivalent of the compound (2), preferably from 5 to 30 equivalents.

The reaction temperature may be generally from 0 to 130° C., preferably from 20 to 130° C.

The reaction time may be generally from 1 to 48 hours, preferably from 6 to 24 hours.

Not specifically defined, the reaction solvent may be any one not interfering with the reaction, including, for example, hexane, toluene, benzene, xylene et al. Of those, preferred is toluene.

The compound (19) thus obtained may be subjected to the next step, after isolated and purified in any known manner for separation and purification, for example, through concentration under reduced pressure, crystallization, solvent extraction, reprecipitation, chromatography, or not after isolated and purified.

(Step 23)

This step is a method for producing a compound (20) by processing the compound (19) with borane/dimethyl sulfide complex, then processing the intermediate with methanol, and oxidizing it with hydrogen peroxide.

The amount of borane/dimethyl sulfide complex to be used may be from 1 to 3 equivalents relative to 1 equivalent of the compound (2), preferably from 1 to 1.5 equivalents.

The reaction temperature may be generally from 0 to 50° C., preferably from 0 to 30° C.

The reaction time may be generally from 10 minutes to 5 hours, preferably from 30 minutes to 3 hours.

The reaction solvent includes hexane, THF, diethyl ether et al, preferably THF.

Next, an excessive amount of methanol is added to the reaction system for methanol treatment.

The amount of methanol to be used may be from 2 to 10 equivalents relative to 1 equivalent of the compound (19), preferably from 2 to 5 equivalents. The reaction temperature may be generally from 0 to 50° C., preferably from 0 to 30° C.

The reaction time may be generally from 1 to 24 hours, preferably from 1 to 12 hours.

After the reaction solvent is evaporated off under reduced pressure, the obtained intermediate is oxidized with hydrogen peroxide.

The amount of hydrogen peroxide to be used may be from 1 to 3 equivalents relative to 1 equivalent of the compound (19), preferably from 1 to 1.5 equivalents.

The reaction temperature may be generally from 0 to 40° C., preferably from 0 to 30° C.

The reaction time may be generally from 1 to 5 hours, preferably from 1 to 3 hours.

The reaction solvent includes THF, 1,4-dioxane, acetonitrile, methanol et al, preferably THF.

The compound (20) thus obtained may be subjected to the next step, after isolated and purified in any known manner for separation and purification, for example, through concentration under reduced pressure, crystallization, solvent extraction, reprecipitation, chromatography, or not after isolated and purified.

(Step 24)

This step is a method for producing a compound (21) by oxidizing the compound (20) in the presence of AD-mix-β and methanesulfonamide.

The amount of AD-mix-β to be used may be 1.4 g relative to 1 mmol of the compound (20).

The amount of methanesulfonamide to be used may be from 1 to 5 equivalents relative to 1 equivalent of the compound (20), preferably from 1 to 3 equivalents.

The reaction solvent includes mixed solvent of t-butanol and water, or mixed solvent of t-butanol, t-butyl methyl ether and water, preferably mixed solvent of t-butanol and water.

The reaction temperature may be generally from 0 to 30° C., preferably from 0 to 10° C.

The reaction time may be generally from 4 to 24 hours, preferably from 6 to 12 hours.

The compound (21) thus obtained may be subjected to the next step, after isolated and purified in any known manner for separation and purification, for example, through concentration under reduced pressure, crystallization, solvent extraction, reprecipitation, chromatography, or not after isolated and purified.

(Step 25)

This step is a method for producing a compound (22) by epoxidizing the compound (21). This step is attained in two stages.

(25-1) A step of reacting the compound (21) with trimethoxyethane in the presence of chlorotrimethylsilane.

(25-2) A step of processing the compound obtained in the previous step with a base in methanol.

(25-1)

The amount of trimethoxyethane to be used may be from 1 to 5 equivalents relative to 1 equivalent of the compound (21), preferably from 1 to 3 equivalents.

The amount of chlorotrimethylsilane to be used may be from 1 to 5 equivalents relative to 1 equivalent of the compound (21), preferably from 1 to 3 equivalents.

The reaction temperature may be generally from 0 to 60° C., preferably from 0 to 30° C.

The reaction time may be generally from 1 to 8 hours, preferably from 1 to 4 hours.

The reaction solvent includes chloroform, dichloromethane, 1,2-dichloroethane, THF, ethyl acetate, toluene et al, preferably chloroform.

After the reaction, the reaction solvent was evaporated off under reduced pressure, and the resulting compound may be directly used in the next step without being purified.

(25-2)

The base to be used includes potassium carbonate, sodium carbonate, cesium carbonate et al, preferably potassium carbonate.

The amount of the base to be used may be from 1 to 10 equivalents relative to 1 equivalent of the compound (21), preferably from 1 to 5 equivalents.

The reaction solvent includes methanol, ethanol et al, preferably methanol.

The reaction temperature may be generally from 0 to 60° C., preferably from 0 to 30° C.

The reaction time may be generally from 1 to 12 hours, preferably from 2 to 6 hours.

The compound (22) thus obtained may be subjected to the next step, after isolated and purified in any known manner for separation and purification, for example, through concentration under reduced pressure, crystallization, solvent extraction, reprecipitation, chromatography, or not after isolated and purified.

(Step 26)

This step is a method for producing a compound (23) by reacting the compound (22) with a compound (4) in the presence of a base.

The amount of the compound (4) to be used may be from 1 to 5 equivalents relative to 1 equivalent of the compound (22), preferably from 1 to 3 equivalents.

The base includes potassium carbonate, sodium carbonate, cesium carbonate et al, preferably potassium carbonate.

The amount of the base to be used may be from 1 to 6 equivalents relative to 1 equivalent of the compound (22), preferably from 1 to 3 equivalents.

Not specifically defined, the reaction solvent may be any one not interfering with the reaction, including, for example, THF, DMF, chloroform, dichloromethane, toluene, benzene, methanol, ethanol et al. Of those, preferred is methanol.

The reaction temperature may be generally from 0° C. to 80° C., preferably from 0° C. to 40° C.

The reaction time may be generally from 1 to 48 hours, preferably from 1 to 24 hours.

The compound (23) thus obtained may be subjected to the next step, after isolated and purified in any known manner for separation and purification, for example, through concentration under reduced pressure, crystallization, solvent extraction, reprecipitation, chromatography, or not after isolated and purified.

(Step 27)

This step is for obtaining a compound (24) by processing the compound (23) according to the step 13 for ring closure reaction, and then removing the hydroxyl-protective group P1 from the obtained compound according to the step 5. The reaction conditions and others described in the step 13 and the step 5 are applicable to this step.

The compound (24) thus obtained may be subjected to the next step, after isolated and purified in any known manner for separation and purification, for example, through concentration under reduced pressure, crystallization, solvent extraction, reprecipitation, chromatography, or not after isolated and purified.

(Step 28)

This step is a method for producing a compound (I-5) by reacting the compound (24) and a compound (8-2) in a mode of Mitsunobu reaction. This reaction may be attained according to the step 6b.

(Step 29)

This step is a method for producing a compound (I-5-1) by oxidizing the compound (I-5).

This reaction may be attained according to the (step 11-1) and (11-2), or the (step 15-2).

The compound (I-5) or the compound (I-5-1) thus obtained may be isolated and purified in any known manner for separation and purification, for example, through concentration under reduced pressure, crystallization, solvent extraction, reprecipitation, chromatography.

Optically-active compounds (I-5') and (I-5'-1) having a configuration opposite to that of the compounds (I-5) and (I-5-1) of the invention may be produced from the compound (20) in the (step 24) in which AD-mix-α is used in place of AD-mix-β.

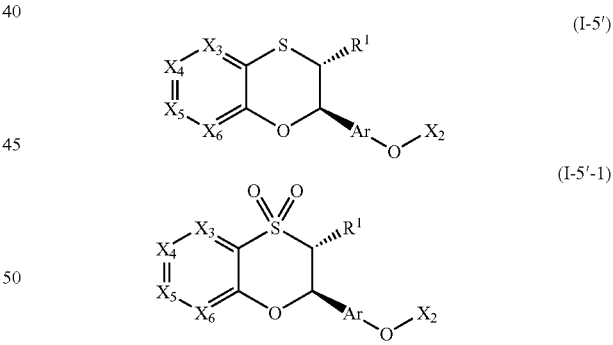

[In the formulae, the symbols are the same as above.]

The compounds (I-5) and (I-5-1) of the invention may also be obtained through optical resolution with chiral column chromatography of racemates (I-3) and (I-3-1).

Optically-active compounds (24) of the invention may also be produced according to the following method.

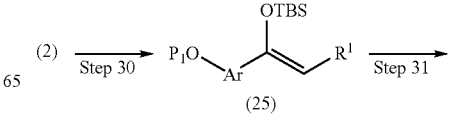

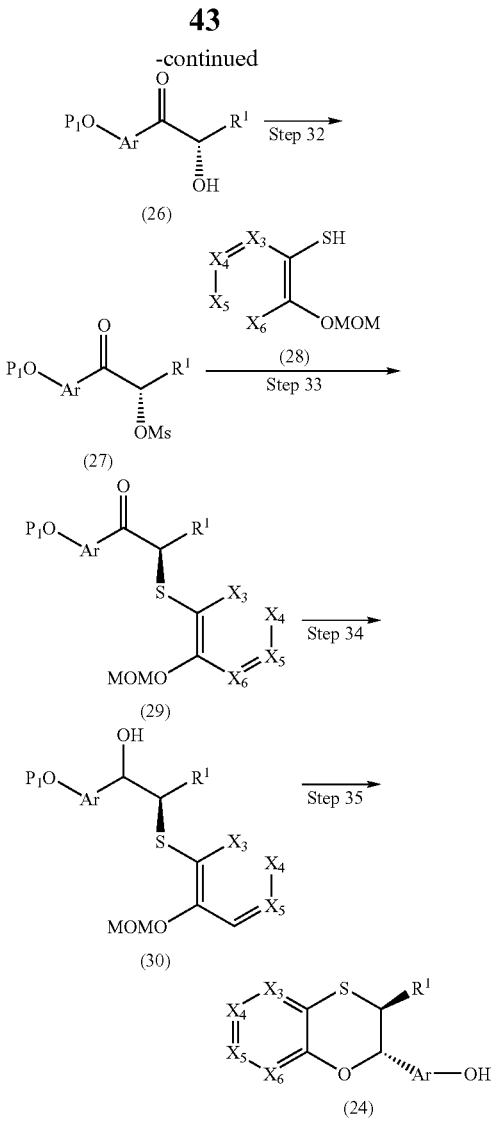

[In the formula, the symbols are the same as above.]

(Step 30)

This step is a method for producing a compound (25) by reacting a compound (2) with t-butyldimethylsilyl chloride in the presence of potassium hexamethyldisilazide.

The amount of t-butyldimethylsilyl chloride to be used may be from 1 to 10 equivalents relative to 1 equivalent of the compound (2), preferably from 1 to 3 equivalents.

The amount of potassium hexamethyldisilazide to be used may be from 1 to 10 equivalents relative to 1 equivalent of the compound (2), preferably from 1 to 3 equivalents.

The reaction temperature may be generally from −78 to 100° C., preferably from −20 to 30° C.

The reaction time may be generally from 1 to 48 hours, preferably from 1 to 12 hours.

Not specifically defined, the reaction solvent may be any one not interfering with the reaction, including, for example, THF, diethyl ether et al.

The compound (25) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 31)

This step is a method for producing a compound (26), starting from the compound (25). This step may be attained according to the (step 24).

The compound (26) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 32)

This step is a method for producing a compound (27) by reacting the compound (26) with methanesulfonyl chloride in the presence of a base.

The amount of methanesulfonyl chloride to be used may be from 1 to 10 equivalents relative to 1 equivalent of the compound (26), preferably from 1 to 5 equivalents.

The base includes triethylamine, N-ethyldiisopropylamine, sodium carbonate, potassium carbonate, cesium carbonate et al. Of those, preferred is triethylamine.

The reaction temperature may be generally from −78° C. to 50° C., preferably from −20° C. to 30° C.

The reaction time may be generally from 0.1 to 5 hours, preferably from 0.1 to 2 hours.

Not specifically defined, the reaction solvent may be any one not interfering with the reaction, including, for example, THF, diethyl ether, chloroform, dichloromethane, acetonitrile, ethyl acetate et al. Of those, preferred is dichloromethane.

The compound (27) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 33)

This step is a method for producing a compound (29) by reacting the compound (27) with a compound (28) in the presence of cesium fluoride.

The amount of cesium fluoride to be used may be from 1 to 10 equivalents relative to 1 equivalent of the compound (27), preferably from 1 to 3 equivalents.

Not specifically defined, the reaction solvent may be any one not interfering with the reaction, including, for example, THF, DMF, diethyl ether et al. Of those, preferred is DMF.

The compound (29) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 34)

This step is a method for producing a compound (39) by reducing the compound (29) with lithium borohydride.

The amount of lithium borohydride to be used may be from 1 to 5 equivalents relative to 1 equivalent of the compound (29), preferably from 1 to 2 equivalents.

The reaction temperature may be generally from −78° C. to 50° C., preferably from −20° C. to 20° C.

The reaction time may be generally from 1 to 24 hours, preferably from 1 to 12 hours.

Not specifically defined, the reaction solvent may be any one not interfering with the reaction, including, for example, THF, diethyl ether et al.

The compound (30) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 35)

This step is a method for producing a compound (24) by removing the protective group from the compound (30) by the use of trifluoroacetic acid, at the same time, by cyclization, in the presence of anisole.

The amount of trifluoroacetic acid to be used may be generally from 5 to 100 equivalents relative to 1 equivalent of the compound (30), preferably from 5 to 20 equivalents.

The amount of anisole to be used may be generally from 1 to 20 equivalents relative to 1 equivalent of the compound (30), preferably from 1 to 5 equivalents.

The reaction temperature may be generally from −20° C. to 50° C., preferably from −20° C. to 20° C.

The reaction time may be generally from 0.1 to 10 hours, preferably from 0.1 to 3 hours.

Not specifically defined, the reaction solvent may be any one not interfering with the reaction, including, for example, dichloromethane, chloroform, toluene, THF, 1,4-dioxane et al. Further, trifluoroacetic acid may also be used as the solvent.

The compound (24) thus obtained may be purified in any known manner for separation and purification, for example, through concentration, concentration under reduced pressure, crystallization, solvent extraction, reprecipitation, chromatography, especially through recrystallization to give a product having a high optical purity.

Optically-active compounds (24') having a configuration opposite to that of the compounds (24) of the invention may be produced from the compound (2) in the (step 31) in which AD-mix-α is used in place of AD-mix-β.

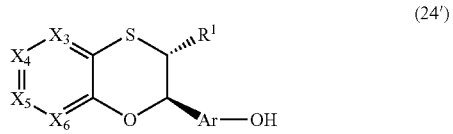

(24')

The compounds of the invention may be converted into pharmaceutically-acceptable salts or esters in an ordinary manner; and on the contrary, such salts or esters may be converted into the corresponding free compounds in an ordinary manner.

The compounds of the invention may exist as pharmaceutically-acceptable salts, and the salts may be produced in an ordinary manner, using the compounds of the invention. The acid addition salts include, for example, hydrohalides (e.g., hydrochlorides, hydrofluorides, hydrobromides, hydroiodides et al), inorganic acid salts (e.g., nitrates, perchlorates, sulfates, phosphates, carbonates et al), lower alkylsulfonates (e.g., methanesulfonates, trifluoromethanesulfonates, ethanesulfonates et al), arylsulfonates (e.g., benzenesulfonates, p-toluenesulfonates et al), organic acid salts (e.g., fumarates, succinates, citrates, tartrates, oxalates, maleates et al), and amino acid salts (e.g., glutamates, aspartates et al).

The base addition salts include, for example, alkali metal salts (e.g., sodium salts, potassium salts et al), alkaline earth metal salts (e.g., calcium salts, magnesium salts et al), ammonium salts, and organic base (e.g., guanidine, triethylamine, dicyclohexylamine et al) addition salts. Further, the compounds of the invention may be in any form of hydrates or solvates of their free compounds or salts.

The compounds of the invention may be administered orally or parenterally.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin et al.

A mixture of the compound of the invention and the above additives may be used as solid preparations (e.g., tablets, capsules, granules, powders, suppositories et al) and liquid preparations (e.g., syrups, elixirs, injections et al). These preparations can be produced in an ordinary method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto. The preparations may contain the compound of the invention in an amount of from 1.0 to 100% by weight, preferably from 1.0 to 60% by weight of the preparation.

The compounds of the invention may be formulated into preparations, for example, according to the following Formulation Examples.

Formulation Example 1

10 parts of the compound of Example 1 to be described hereinunder, 15 parts of heavy magnesium oxide and 75 parts of lactose are uniformly mixed to prepare a powdery or granular preparation having a particle size of at most 350 μm. The preparation was encapsulated to give capsules.

Formulation Example 2

45 parts of the compound of Example 1 to be described hereinunder, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 μm.

Formulation Example 3

A granular preparation is prepared in the same manner as in Formulation Example 2. 96 parts of the granular preparation is mixed with 3 parts of calcium stearate, and shaped under compression into tablets having a diameter of 10 mm.

Formulation Example 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug, as described below.

In their use, the compounds of the invention may be combined with any other drug effective for treatment (prevention or therapy) of metabolic disorders or dietary disorders. The individual ingredients to be combined may be administered at different times or at the same time, either as one preparation or as divided different preparations. The combination of the compound of the invention with any other drug effective for treatment of metabolic disorders or dietary disorders includes, in principle, combinations thereof with any and every drug effective for treatment of metabolic disorders or dietary disorders.

The compounds of the invention may also be combined with any other drug effective for hypertension, obesity-related hypertension, hypertension-related disorders, cardiomegaly, left ventricle hypertrophy, metabolic disorders, obesity, obesity-related disorders (these are hereinafter referred to as "co-drugs"). Combined with the compound of the invention, such co-drugs may be administered at the same time or at different times or successively in order in prevention or treatment of the above-mentioned disorders. When the compound of the invention is used simultaneously with one or more co-drugs, then it may be in a pharmaceutical composition for one-dose administration. However, in such combination therapy, the composition containing the compound of the invention and the co-drug may be administered to subjects simultaneously, or separately or successively. The composition and the co-drug may be packed separately. They may be administered at different times.

The dose of the co-drug may depend on the clinical use thereof, and may be suitably determined in accordance with the administration subject, the administration route, the diseases and the combination. The form of the co-drug for administration is not specifically defined, and it may be combined with the compound of the invention when they are administered. The administration mode includes, for example, the following: (1) A compound of the invention is combined with a co-drug to give a single preparation for single administration; (2) a compound of the invention and a co-drug are separately formulated into different two preparations, and the two preparations are simultaneously administered in one administration route; (3) a compound of the invention and a co-drug are separately formulated into different two preparations, and they are administered at different times in one and the same administration route; (4) a compound of the invention and a co-drug are separately formulated into different two preparations, and they are administered at the same time in two different administration routes; (5) a compound of the invention and a co-drug are separately formulated into different two preparations, and they are administered at different times in different administration routes (for example, a compound of the invention and a co-drug are administered in that order, or in an order contrary to this). The blend ratio of the compound of the invention and the co-drug may be suitably determined depending on the administration subject, the administration route, and the disease for the administration.

The co-drugs usable in the invention include drugs for diabetes, drugs for hyperlipemia, drugs for hypertension, and anti-obesity drugs. Two or more such co-drugs may be combined in an adequate ratio and used.

Drugs for diabetes include, for example,
1) PPAR-γ agonists such as glitazones (e.g., ciglitazone, darglitazone, englitazone, isaglitazone, (MCC-555) et al), pioglitazone, rosiglitazone, troglitazone, BRL49653, CLX-0921, 5-BTZD, GW-0207, LG-100641, LY-300512 et al;
2) biguanides such as metformin, buformin, phenformin et al;
3) protein tyrosine phosphatase 1B inhibitors;
4) sulfonylureas such as acetohexamide, chloropropamide, diabinese, glibenclamide, glipizide, glyburide, glimepiride, gliclazide, glipentide, gliquidone, glisolamide, trazamide, tolubutamide et al;
5) meglitinides such as repaglinide, nateglinide et al;
6) α-glucoside hydroxylase inhibitors such as acarbose, adiposine, camiglibose, emiglitate, miglitol, voglibose, pradimicin-Q, salbostatin, CKD-711, MDL-25, 673, MDL-73, 945, MOR14 et al;
7) α-amylase inhibitors such as tendamistat, trestatin, A13688 et al;
8) insulin secretion promoters such as linogliride, A-4166 et al;
9) fatty acid oxidation inhibitors such as clomoxir, etomoxir et al;
10) A2 antagonists such as midaglizole, isaglidole, deriglidole, idazoxan, earoxan, fluparoxan et al;
11) insulin or insulin mimetics such as biota, LP-100, novalapid, insulin determir, insulin lispro, insulin glargine, insulin zinc, Lys-Pro-insulin, GLP-1 (73-7), GLP1 amide (7-36) et al;
12) non-thiazolidinediones such as JT-501, farglitazar et al;
13) PPARα/γ dual-agonists such as CLX-0940, GW-1536, GW-1929, GW-2433, KRP-297, L-796449, LR-90 and SB219994 et al;
14) other insulin sensitizers, and
15) VPAC2 receptor agonists.

Drugs for hyperlipidemia include, for example,
1) bile acid absorption promoters such as cholesterylamine, colesevelem, colestipol, crosslinked dextran dialkylaminoalkyl derivatives, Colestid™, LoCholest™, Questran™ et al;
2) HMG-CoA reductase inhibitors such as atorvastatin, itavastatin, fluvastatin, lovastatin, pravastatin, rivastatin, rosuvastatin, simvastatin, ZD-4522 et al;
3) HMG-CoA synthase inhibitors;
4) cholesterol absorption inhibitors such as snatol ester, 13-sitosterol, sterol glucoside, ezetimibe et al;
5) ACAT (acyl-CoA-cholesterol acyl transferase) inhibitors such as avasimibe, eflucimibe, KY-505, SMP-709 et al;
6) CETP inhibitors such as JTT705, torcetrapib, CP532632, BAY-63-2149, SC-591, SC-795 et al;
7) squalane synthetase inhibitors;
8) antioxidants such as probucol;
9) PPAR-α agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid™, Lopid™, Tricor™) et al;
10) FXR receptor antagonists such as GW-4064, SR-103912 et al;
11) LXR receptor agonists such as GW3965, T9013137, XTCO-179628 et al;
12) lipoprotein synthesis inhibitors such as niacin;
13) renin-angiotensin system inhibitors;
14) PPAR-δ partial agonists,
15) bile acid resorption inhibitors such as BARA1453, SC435, PHA384640, S-435, AZD7706 et al;
16) PPAR-δ agonists such as GW501516, GW590735;

17) triglyceride synthetase inhibitors;
18) MTTP (microsomal triglyceride transportation) inhibitors such as inplitapide, LAB687, CP346086 et al;
19) transcriptional modification factors,
20) squalane epoxidase inhibitors;
21) LDL (low-density lipoprotein) receptor inducers,
22) thrombocyte agglutination inhibitors;
23) 5-LO (5-lipoxygenase/FLAP (5-lipoxigenase activated protein) inhibitors; and
24) Niacin receptor agonists.

Drugs for hypertension include, for example,
1) thiazide diuretics such as chlorothialidon, chlorothiazide, dichlorofenamide, hydrofluorothiazide, indapamide, hydrochlorothiazide et al; loop diuretics such as bumetanide, ethacrynic acid, flosemide, tolusemide et al; sodium diuretics such as amyloride, triamuteren et al; aldosterone antagonist such as spironolactone, epilenone et al;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tartatolol, tilisolol, timolol et al;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil et al;
4) angiotensin converting enzyme inhibitors such as benazepril, captopril, cilazapril, delapril, enalapril, fosinopril, imidapril, rosinopril, moexipril, quinapril, quinaprilat, ramipril, perindopril, perindropril, quanipril, spirapril, tenocapril, trandolapril, zofenopril et al;
5) neutral endopeptidase inhibitors such as omapatrilat, cadoxatril, ecadotril, fosidotril, sampatrilat, AVE7688, ER4030 et al;
6) endothelin antagonists such as tezosentan, A308165, YM62899 et al;
7) vasodilators such as hydraladine, clonidine, minoxidil, nicotinyl alcohol et al;
8) angiotensin II receptor antagonists such as candesartan, eporsartan, iribesartan, losartan, pratosartan, tasosartan, telmisartan, valsartan, EXP-3137, FI6828K, RNH6270 et al;
9) α/β adrenaline blockers such as nipradilol, arotinolol, amoslalol et al;
10) α1 blockers such as terazosin, urapidil, purazosin, bunazosin, trimazosin, doxazosin, naphthopidil, indolamin, WHIP164, XEN010 et al;
11) α2 agonists such as lofexidine, tiamenidine, moxonidine, rilmenidine, guanobenz et al;
12) aldosterone inhibitors.

Anti-obesity drugs include, for example,
1) 5HT (serotonin) transporter inhibitors such as paroxetine, fluoxetine, fenfluramine, fluvoxamine, sertraline, imipramine et al;
2) NE (norepinephrine) transporter inhibitors such as GW320659, desipramine, talsupram, nomifensin et al;
3) CB-1 (cannabinoid-1 receptor 1) antagonists/inverse-agonists such as limonabant (Sanofi Synthelabo), SR-147778 (Sanofi Synthelabo), BAY-65-2520 (Bayer), SLV-319 (Sorby), as well as compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, and EP-658546 et al;
4) ghrelin antagonists such as compounds disclosed in WO01/87355, WO02/08250 et al;
5) histamine (H3) antagonists/inverse-agonists such as thioperamide, 3-(1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol] carbamate, piperazine-containing H3-receptor antagonists (Lazewska, D. et al., Pharmazie, 56: 927-32 (2001)), benzophenone derivatives (Sasse, A. et al., Arch. Pharma (Weinheim) 334: 45-52 (2001)), substituted N-phenylcarbamates (Reidemeister, S. et al., Pharmazie, 55: 83-6 (2000)), proxyfen derivatives (Sasse; A. et al., J. Med. Chem., 43: 3335-43 (2000)) et al;
6) MCH-1R (melanin-concentrating hormone receptor 1) antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, and JP-A-2001-226269 et al;
7) MCH-2R (melanin-concentrating hormone receptor 2) agonists/antagonists;
8) NPY1 (neuropeptide Y Y1) antagonists such as BIBP3226, BIB03304, J-115814, LY-357897, CP-671906, GI-264879, and other compounds disclosed in U.S. Pat. No. 6,001,836, WO96/14307, WO01/23387, WO99/51600, WO01/85690, WO01/85098, WO01/85173, and WO01/89528 et al;
9) NPY5 (neuropeptide Y Y5) antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298, 6,337,332, 6,329,395, 340,683, 6,326,375, 6,329,395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/23388, WO01/23389, WO01/44201, WO01/62737, WO01/62738, WO02/20488, WO02/22592, WO02/48152, WO02/49648, WO02/094789, and compounds disclosed in Norman et al., J. Med. Chem., 43:4288-4312 (2000) et al;
10) leptins such as human recombinant leptin (PEG-OB, Hoffman La Roche), recombinant methionylleptin (Amgen);
11) leptin derivatives such as compounds disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519, and WO96/23520 et al;
12) opioid antagonists such as nalmefen (Revex™), 3-methoxynaltrexone, naloxone, naltrexone, compounds disclosed in WO00/21509 et al;
13) orexin antagonists such as SB-334867A, and other compounds disclosed in WO01/96302, WO01/68609, WO02/51232, WO02/51838, and WO03/023561 et al;

14) BRS3 (bonbesin receptor subtype-)3 agonists;
15) CCK-A (cholecystokinin A) agonists such as AR-R15849, GI-181771, JMV-180, A-71378, A-71623, SR-146131, and other compounds disclosed in U.S. Pat. No. 5,739,106 et al;
16) CNTF (ciliary neurotrophic factors) such as GI-181771 (Glaxo-Smith Kline), SR146131 (Sanofi Synthelabo), butabindide, PD170,292, PD149164 (Pfizer) et al;
17) CNTF derivatives such as axokine (Regeneron), and other compounds disclosed in WO94/09134, WO98/22128, WO99/43813 et al;
18) GHS (growth hormone secretion promoter receptor) agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888 et al;
19) 5HT2c (serotonin receptor 2c) agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457 et al;
20) Mc3r (melanocortin-3 receptor) agonists;
21) Mc4r (melanocortin-4 receptor) agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, and WO03/009847 et al;
22) monoamine resorption inhibitors such as cibtramin (Meridia™/Reductil™) and its salts, and other compounds disclosed in U.S. Pat. Nos. 4,746,680, 4,806,570, 5,436, 272, US Patent Application No. 2002/0006964, WO01/27068, and WO01/62341 et al;
23) serotonin re-uptake inhibitors such as dexfenfluramine, fluoxetine, and other compounds disclosed in U.S. Pat. No. 6,365,633, WO01/27060, and WO01/162341 et al;
24) GLP1 (glucagon-like peptide-1) agonists;
25) topiramate (Topimax™);
26) phytopharm compound 57 (e.g., CP644,673);
27) ACC2 (acetyl CoA carboxylase-2) inhibitors;
28) β3 (adrenalin receptor-3) agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. Nos. 5,705,515, 5,451,677, WO01/74782, and WO02/32897 et al;
29) DGAT1 (diacylglycerol acyltransferase-1) inhibitors;
30) DGAT2 (diacylglycerol acyltransferase-2) inhibitors,
31) FAS (fatty acid synthetase) inhibitors such as carulenin, C75 et al;
32) PDE (phosphodiesterase) inhibitors such as theophylline, pentoxiphylline, zaprinast, sildenafil, aminone, milrinone, cilostamide, rolipram, and cilomilast et al;
33) thyroid hormone-β agonists such as KB-2611 (KaroBio BMS), and other compounds disclosed in WO02/15845, JP-A-2000-256190 et al;
34) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TT-NPB), retinoic acid, and other compounds disclosed in WO99/00123 et al;
35) acylestrogens such as oleoylestrone (disclosed in del Mar-Grasa, M. et al., Obesity Research, 9:202-9 (2001)) et al;
36) glucocorticoid antagonists;
37) 11-β HSD1 (11-β-hydroxysteroid dehydrogenase-1) inhibitors such as BVT3498, BVT2733, and other compounds disclosed in WO01/90091, WO01/90090, WO01/90092 et al;
38) SCD1 (stearoyl-CoA desaturase-1) inhibitors;
39) DP-IV (dipeptidyl peptidase-IV) inhibitors such as isoleucine thiazolidine, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP 1258476, WO02/083128, WO02/062764, WO03/000250, WO03/002530, WO03/002531, WO03/002553, WO03/002593, WO03/000180, and WO03/000181 et al;
40) lipase inhibitors such as tetrahydroliptatin (Orlistat/Xenical™), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. Nos. 4,598,089, 4,452,813, 5,512,565, 5,391,571, 5,602,151, 4,405,644, 4,189,438, and 4,242,453 et al;
41) fatty acid transporter inhibitors;
42) dicarboxylate transporter inhibitors;
43) glucose transporter inhibitors;
44) phosphate transporter inhibitors;
45) melanocortin antagonists such as melanotan II, and other compounds disclosed in WO99/64002, WO00/746799 et al;
46) melanin-concentrating hormone antagonists;
47) galanin antagonists;
48) CCK agonists;
49) corticotrophin release hormones;
50) PDE3 (phosphodiesterase 3B) agonists.

The compounds of the invention may be combined with one or more of the above-mentioned co-drugs. The combination of the compound of the invention with one or more co-drugs selected from a group consisting of drugs for diabetes and drugs for hyperlipemia is useful for prevention or remedy of metabolic disorders. In particular, a combination of the compound of the invention with a drug for hypertension and an anti-obesity drug along with a drug for diabetes or a drug for hyperlipemia is useful for prevention or remedy of metabolic disorders owing to the synergistic effect thereof.

When the compounds of the invention are used in clinical sites, then the dose and the administration frequency thereof may vary depending on the sex, the age, the body weight and the condition of the patient and on the type and the scope of the intended treatment. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions. Ordinary physicians, veterinarians and clinicians may readily determine the effective dose necessary for retarding, inhibiting or stopping the development of diseases.

EXAMPLES

The invention is described more concretely with reference to the following Examples, which, however, do not whatsoever restrict the invention.

For the thin-layer chromatography in the Examples, used was a plate of TLC Plate Silicagel 60F$_{245}$ (Merck) or TLC Plate NH (Fuji Silicia Chemical); and for detection, used was a UV detector. For silica gel column chromatography, used were columns of Wakogel™ C-300 (Wako Pure Chemicals) or Chromatorex™ NH 100-200 mesh (Fuji Silicia Chemical), or filled silica gel columns (FLASH+™ cartridge, KP-Sil FLASH12+M, FLASH25+M or FLASH40+M (Biotage Japan)). As a reversed-phase column, used was CombiPrep™ Pro C18 (YMC). For mass spectrometry, used was QuattroII (Micromass) according to an electrospray ionization (ESI) process or an atmospheric chemical ionization (APCI) process.

In NMR spectrometry, dimethyl sulfoxide was used for the internal standard in measurement in a heavy dimethyl sulfoxide solution. Using a spectrometer of Mercury 400 (400 MHz; Varian), Inova 400 (400 MHz; Varian) or AL-400 (400 MHz; JEOL), the sample was analyzed for the total δ value in ppm.

The meanings of the abbreviations in the following Examples are mentioned below.
CDCl$_3$: deuterated chloroform
CD$_3$OD: deuterated methanol
DMSO-d6: deuterated dimethylsulfoxide
The meanings of the abbreviations in nuclear magnetic resonance spectra are mentioned below.
s: singlet
d: doublet
dd: double-doublet
t: triplet
m: multiplet
br: broad
brs: broad singlet
q: quartet
J: coupling constant
Hz: hertz

Example 1

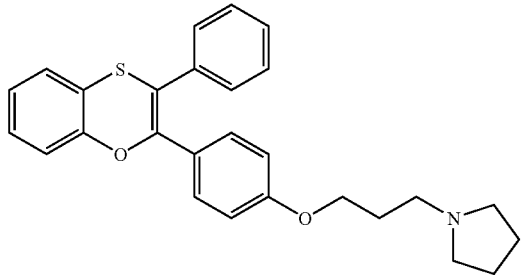

Synthesis of 3-phenyl-2-[4-[3-(1-pyrrolidinyl)propoxy]phenyl]-1,4-benzoxathiin

Potassium carbonate (83 mg) and 1-(3-bromopropyl)piperidine hydrobromide (54.6 mg) were added to a DMF (3 mL) solution of 4-(3-phenyl-1,4-benzoxathiin-2-yl)phenol (63.7 mg, 0.2 mmol) obtained in Reference Example 1-1, and stirred at 80° C. for 8 hours. The reaction liquid was restored to room temperature, diluted with ethyl acetate, and extracted with distilled water. The organic layer was dried with magnesium sulfate, and concentrated under reduced pressure. The obtained residue was purified by preparative thin-layer silica gel column chromatography (chloroform:methanol=9:1) to obtain the entitled compound (43.7 mg, 51%) as a yellow oil.

$^1$HNMR (400 MHz, CDCl$_3$, δ): 1.79-2.01 (4H, m), 2.56-2.65 (6H, m), 3.98 (2H, t, J=6.3 Hz), 6.69-6.71 (2H, m), 7.00-7.06 (2H, m), 7.11-7.25 (9H, m)
ESI-MS (m/e): 430.2 [M+H]$^+$

Example 2

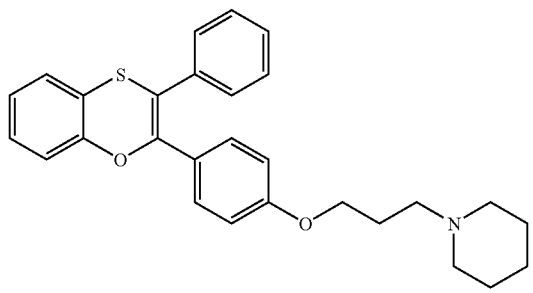

Synthesis of 3-phenyl-2-[4-[3-(1-piperidinyl)propoxy]phenyl]-1,4-benzoxathiin

The entitled compound was obtained according to the method of Example 1 but using 4-(3-phenyl-1,4-benzoxathiin-2-yl)phenol obtained in Reference Example 1-1 and 1-(3-bromopropyl)piperidine as the starting material.

$^1$HNMR (400 MHz, CDCl$_3$, δ): 1.44-1.45 (2H, m), 1.57-1.63 (4H, m), 1.92-1.99 (2H, m), 2.41-2.48 (6H, m), 3.95 (2H, t, J=6.3 Hz), 6.68-6.71 (2H, m), 7.00-7.25 (11H, m)
ESI-MS (m/e): 444.2 [M+H]$^+$

Example 3

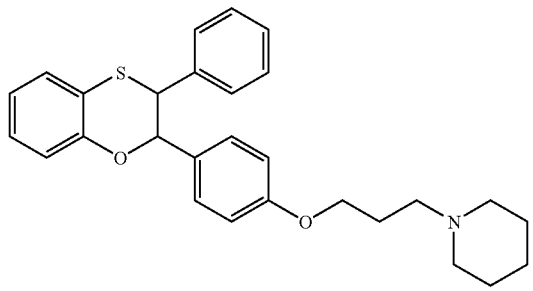

Synthesis of (2,3-cis)-2,3-dihydro-3-phenyl-2-[4-[3-(1-piperidinyl)propoxy]phenyl]-1,4-benzoxathiin 1-(3-Hydroxypropyl)piperidine (33.5 mg), tri-n-butyl phosphine (58 μL) and 1,1'-(azodicarbonyl)dipiperidine (57 mg) were added in that order to a THF (3 mL) solution of 4-[(2,3-cis)-3-phenyl-2,3-dihydro-1,4-benzoxathiin-2-yl] phenol (25 mg, 0.078 mmol) synthesized in Reference Example 2-1, and stirred at room temperature for 14 hours. The reaction liquid was cooled with ice, and the precipitated powder was collected by filtration, and washed with cold THF. The mother liquid was concentrated under reduced pressure, and the obtained residue was purified by thin-layer silica gel column chromatography (chloroform:methanol=9:1) and further by thin-layer NH silica gel column chromatography (hexane:ethyl acetate=3:1) to obtain the entitled compound (19.5 mg, 56%).

$^1$HNMR (400 MHz, CDCl$_3$, δ): 1.44-1.56 (2H, m), 1.57-1.61 (4H, m), 1.91-1.96 (2H, m), 2.39-2.47 (6H, m), 3.95 (2H, t, J=6.4 Hz), 4.39 (1H, d, J=2.3 Hz), 5.53 (1H, d, J=2.3 Hz), 6.71-6.74 (2H, m), 6.89-7.00 (6H, m), 7.05-7.20 (5H, m)

ESI-MS (m/e): 446.3 [M+H]$^+$

Example 4

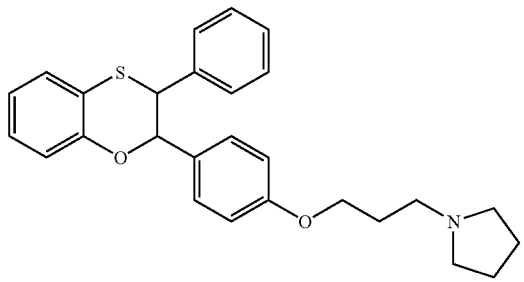

Synthesis of (2,3-cis)-2,3-dihydro-3-phenyl-2-[4-[3-(1-pyrrolidinyl)propoxy]phenyl]-1,4-benzoxathiin The entitled compound was obtained according to the method of Example 3 but using 4-[(2,3-cis)-3-phenyl-2,3-dihydro-1,4-benzoxathiin-2-yl]phenol synthesized in Reference Example 2-1 and 1-(3-hydroxypropyl)pyrrolidine as the starting material.

$^1$HNMR (400 MHz, CDCl$_3$, δ): 1.77-1.80 (4H, m), 1.90-2.01 (2H, m), 2.50-2.54 (4H, m), 2.58-2.62 (2H, m), 3.97 (2H, t, J=6.5 Hz), 4.39 (1H, d, J=2.3 Hz), 5.53 (1H, d, J=2.3 Hz), 6.72-6.74 (2H, m), 6.88-7.00 (6H, m), 7.05-7.20 (5H, m)

ESI-MS (m/e): 432.3 [M+H]$^+$

Example 5

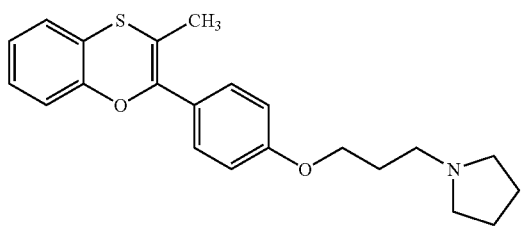

Synthesis of 3-methyl-2-[4-[3-(1-pyrrolidinyl)propoxy]phenyl]-1,4-benzoxathiin

The entitled compound was obtained according to the method of Example 3 but using 4-(3-methyl-1,4-benzoxathiin-2-yl)phenol synthesized in Reference Example 1-2 and 1-(3-hydroxypropyl)pyrrolidine as the starting material.

$^1$HNMR (400 MHz, CDCl$_3$, δ): 1.78-1.81 (4H, m), 1.98-2.04 (5H, m), 2.51-2.55 (4H, m), 2.61-2.65 (2H, m), 4.05 (2H, t, J=6.5 Hz), 6.90-7.10 (6H, m), 7.35-7.38 (2H, m)

ESI-MS (m/e): 368.2 [M+H]$^+$

Example 6

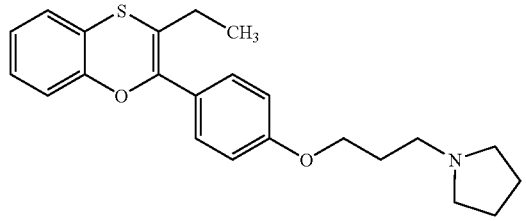

Synthesis of 3-ethyl-2-[4-[3-(1-pyrrolidinyl)propoxy]phenyl]-1,4-benzoxathiin

The entitled compound was obtained according to the method of Example 3 but using 4-(3-ethyl-1,4-benzoxathiin-2-yl)phenol synthesized in Reference Example 1-3 and 1-(3-hydroxypropyl)pyrrolidine as the starting material.

$^1$HNMR (400 MHz, CDCl$_3$, δ): 1.14 (3H, t, J=7.4 Hz), 1.78-1.81 (4H, m), 2.00-2.04 (2H, m), 2.32-2.33 (2H, m), 2.51-2.55 (4H, m), 2.61-2.65 (2H, m), 4.04-4.07 (2H, m), 6.90-7.02 (4H, m), 7.08-7.11 (2H, m), 7.33-7.35 (2H, m)

ESI-MS (m/e): 382.2 [M+H]$^+$

Example 7

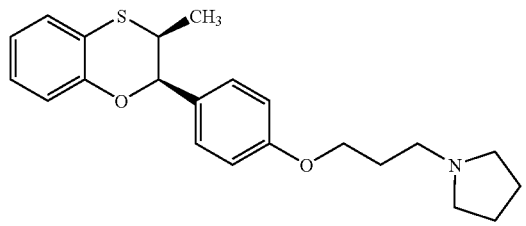

Synthesis of (2,3-cis)-2,3-dihydro-3-methyl-2-[4-[3-(1-pyrrolidinyl)propoxy]phenyl]-1,4-benzoxathiin The entitled compound was obtained according to the method of Example 3 but using 4-[(2,3-cis)-3-methyl-2,3-dihydro-1,4-benzoxathiin-2-yl]phenol synthesized in Reference Example 2-2 and 1-(3-hydroxypropyl)pyrrolidine as the starting material.

$^1$HNMR (400 MHz, CDCl$_3$, δ): 1.23 (3H, d, J=7.0 Hz), 1.77-1.84 (4H, m), 2.00-2.06 (2H, m), 2.54-2.57 (4H, m), 2.63-2.67 (2H, m), 3.23-3.38 (1H, m), 4.05 (2H, t, J=6.5 Hz), 5.42 (1H, d, J=1.6 Hz), 6.87-7.11 (6H, m), 7.32-7.35 (2H, m)

ESI-MS (m/e): 370.2 [M+H]$^+$

Example 8

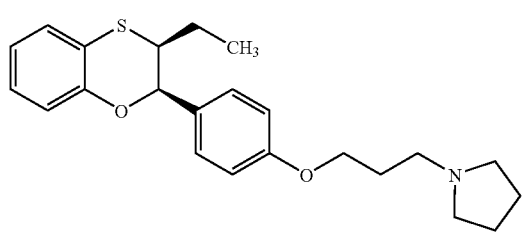

Synthesis of (2,3-cis)-2,3-dihydro-3-ethyl-2-[4-[3-(1-pyrrolidinyl)propoxy]phenyl]-1,4-benzoxathiin The entitled compound was obtained according to the method of Example 3 but using 4-[(2,3-cis)-3-ethyl-2,3-dihydro-1,4-benzoxathiin-2-yl]phenol synthesized in Reference Example 2-3 and 1-(3-hydroxypropyl)pyrrolidine as the starting material.

¹HNMR (400 MHz, CDCl₃, δ): 0.96 (3H, t, J=7.2 Hz), 1.42-1.60 (2H, m), 1.79-1.82 (4H, m), 1.99-2.06 (2H, m), 2.54-2.57 (4H, m), 2.63-2.67 (2H, m), 3.08-3.12 (1H, m), 4.03-4.06 (2H, m), 5.49 (1H, d, J=1.8 Hz), 6.86-7.11 (6H, m), 7.33-7.35 (2H, m)

ESI-MS (m/e): 384.2 [M+H]⁺

Example 9

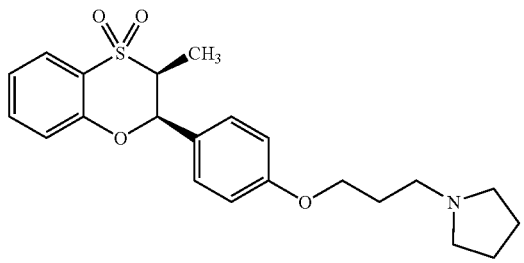

Synthesis of (2,3-cis)-2,3-dihydro-3-methyl-2-[4-[3-(1-pyrrolidinyl)propoxy]phenyl]-1,4-benzoxathiin-4,4-dioxide M-Chloroperbenzoic acid (content 65% or more, 58.9 mg) was added to a dichloromethane (1.5 mL) solution of the compound (16.4 mg, 0.044 mmol) synthesized in Example 7, and stirred at room temperature for 15 hours. Aqueous saturated sodium hydrogensulfite solution (1.5 ml), aqueous saturated sodium hydrogencarbonate solution (1.5 mL) were added to the reaction liquid, and stirred at room temperature for 4 hours. The organic layer was collected, and washed with aqueous saturated sodium chloride solution. After dried with magnesium sulfate, this was concentrated under reduced pressure. The obtained residue was purified by preparative thin-layer silica gel column chromatography (chloroform/methanol=9/1) and further by thin-layer NH silica gel column chromatography (hexane:ethyl acetate=2:8) to obtain the entitled compound (3.23 mg, 18%).

¹HNMR (400 MHz, CDCl₃, δ): 1.26 (3H, d, J=7.2 Hz), 1.79-1.82 (4H, m), 2.02-2.05 (2H, m), 2.53-2.55 (4H, m), 2.63-2.66 (2H, m), 3.29-3.31 (1H, m), 4.07 (2H, t, J=6.4 Hz), 6.08 (1H, d, J=0.8 Hz), 6.97-6.99 (2H, m), 7.10-7.21 (2H, m), 7.37-7.40 (2H, m), 7.49-7.53 (1H, m), 7.85-7.88 (1H, m)

ESI-MS (m/e): 402.2 [M+H]⁺

Example 10

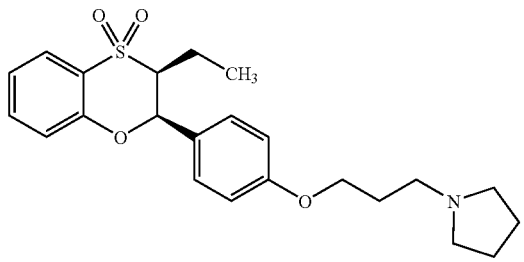

Synthesis of (2,3-cis)-2,3-dihydro-3-ethyl-2-[4-[3-(1-pyrrolidinyl)propoxy]phenyl]-1,4-benzoxathiin-4,4-dioxide The entitled compound was obtained according to the method of Example 9 but using the compound synthesized in Example 8 as the starting material.

¹HNMR (400 MHz, CDCl₃, δ): 0.94 (3H, t, J=7.4 Hz), 1.66-1.82 (6H, m), 2.02-2.07 (2H, m), 2.53-2.57 (4H, m), 2.63-2.67 (2H, m), 3.07-3.11 (1H, m), 4.07 (2H, t, J=6.4 Hz), 6.10 (1H, m), 6.98-7.00 (1H, m), 7.10-7.20 (2H, m), 7.39-7.42 (2H, m), 7.48-7.53 (1H, m), 7.87-7.89 (1H, m)

ESI-MS (m/e): 416.3 [M+H]⁺

Example 11

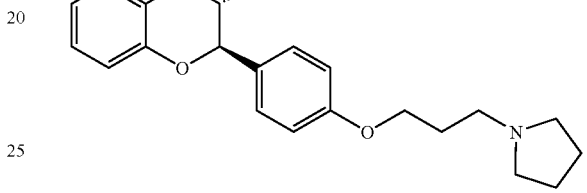

Synthesis of (2,3-trans)-2,3-dihydro-3-methyl-2-[4-[3-(1-pyrrolidinyl)propoxy]phenyl]-1,4-benzoxathiin The entitled compound was obtained according to the method of Example 3 but using 4-[(2,3-trans)-3-methyl-2,3-dihydro-1,4-benzoxathiin-2-yl]phenol synthesized in Reference Example 3-1 and 1-(3-hydroxypropyl)pyrrolidine as the starting material.

¹HNMR (400 MHz, CDCl₃, δ): 1.07 (3H, d, J=6.6 Hz), 1.79-1.83 (4H, m), 1.99-2.06 (2H, m), 2.54-2.58 (4H, m), 2.63-2.67 (2H, m), 3.43-3.47 (1H, m), 4.05 (2H, t, J=6.4 Hz), 4.67 (1H, d, J=8.6 Hz), 6.85-7.01 (5H, m), 7.07-7.10 (1H, m), 7.24-7.27 (2H, m)

ESI-MS (m/e): 370.2 [M+H]⁺

Example 12

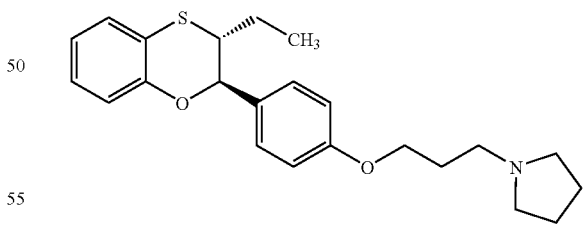

Synthesis of (2,3-trans)-2,3-dihydro-3-ethyl-2-[4-[3-(1-pyrrolidinyl)propoxy]phenyl]-1,4-benzoxathiin The entitled compound was obtained according to the method of Example 3 but using compound synthesized in Reference Example 3-2 and 1-(3-hydroxypropyl)pyrrolidine as the starting material.

¹HNMR (400 MHz, CDCl₃, δ): 0.94 (3H, t, J=7.4 Hz), 1.35-1.50 (2H, m), 1.79-1.82 (4H, m), 1.99-2.06 (2H, m), 2.54-2.57 (4H, m), 2.63-2.67 (2H, m), 3.33-3.38 (1H, m), 4.04 (2H, t, J=6.4 Hz), 4.78 (1H, d, J=8.2 Hz), 6.85-7.01 (5H, m), 7.09-7.12 (1H, m), 7.23-7.26 (2H, m)
ESI-MS (m/e): 384.2 [M+H]⁺

Example 13

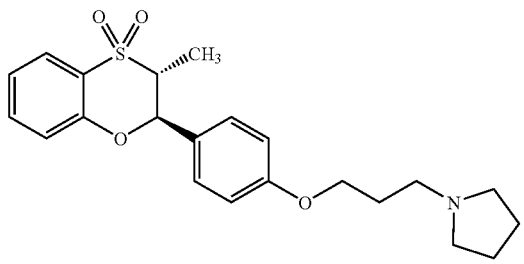

Synthesis of (2,3-trans)-2,3-dihydro-4,4-dioxido-3-methyl-2-[4-[3-(1-pyrrolidinyl)propoxy]phenyl]-1,4-benzoxathiin The entitled compound was obtained according to the method of Example 9 but using the compound synthesized in Example 11 as the starting material.
¹HNMR (400 MHz, CDCl₃, δ): 1.17 (3H, d, J=7.0 Hz), 1.79-1.84 (4H, m), 2.00-2.07 (2H, m), 2.53-2.56 (4H, m), 2.63-2.66 (2H, m), 3.66-3.70 (1H, m), 4.07 (2H, t, J=6.5 Hz), 5.40 (1H, d, J=11.0 Hz), 6.96-7.00 (3H, m), 7.13-7.17 (1H, m), 7.30-7.33 (2H, m), 7.45-7.49 (1H, m), 7.85-7.87 (1H, m)
ESI-MS (m/e): 402.2 [M+H]⁺

Example 14

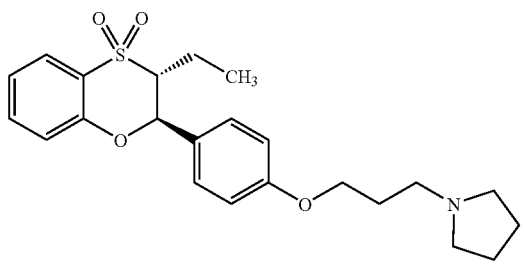

Synthesis of (2,3-trans)-2,3-dihydro-3-ethyl-2-[4-[3-(1-pyrrolidinyl)propoxy]phenyl]-1,4-benzoxathiin-4,4-dioxide The entitled compound was obtained according to the method of Example 9 but using the compound synthesized in Example 12 as the starting material.
¹HNMR (400 MHz, CDCl₃, δ): 0.97 (3H, t, J=7.5 Hz), 1.32-1.39 (1H, m), 1.79-1.82 (4H, m), 1.98-2.07 (3H, m), 2.53-2.56 (4H, m), 2.63-2.66 (2H, m), 3.50-3.56 (1H, m), 4.07 (2H, t, J=6.4 Hz), 5.40 (1H, d, J=11.0 Hz), 6.96-6.99 (3H, m), 7.13-7.17 (1H, m), 7.31-7.34 (2H, m), 7.43-7.47 (1H, m), 7.83-7.86 (1H, m)
ESI-MS (m/e): 416.2 [M+H]⁺

Example 15

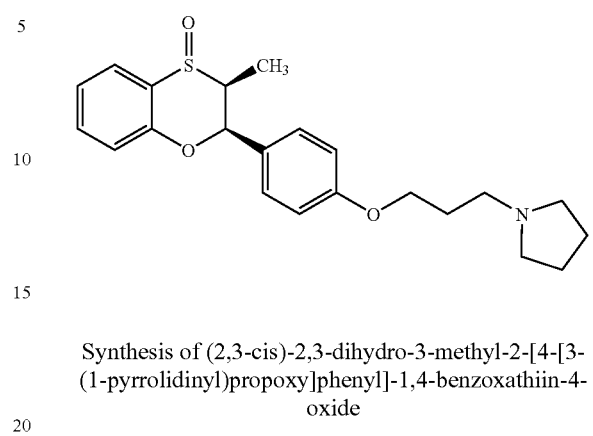

Synthesis of (2,3-cis)-2,3-dihydro-3-methyl-2-[4-[3-(1-pyrrolidinyl)propoxy]phenyl]-1,4-benzoxathiin-4-oxide With cooling with ice, m-chloroperbenzoic acid (content, 65% or more, 72 mg) was added to a dichloromethane (3 mL) solution of the compound (53.0 mg, 0.143 mmol) synthesized in Example 11, and stirred for 3 hours with cooling with ice. Aqueous saturated sodium hydrogensulfite solution (1.5 mL) and aqueous saturated sodium hydrogencarbonate solution (2 mL) were added to the reaction solution, and stirred at room temperature for 2 hours. The organic layer was washed with aqueous saturated sodium hydrogencarbonate solution and aqueous saturated sodium chloride solution in that order. This was dried with magnesium sulfate, and concentrated under reduced pressure. The obtained residue was purified by preparative thin-layer silica gel column chromatography (chloroform:methanol=10:1) and further by thin-layer NH silica gel column chromatography (hexane:ethyl acetate=2:8) to obtain the entitled compound (5.29 mg, 10%).
¹HNMR (400 MHz, CDCl₃, δ): 0.94 (3H, d, J=7.4 Hz), 1.79-1.82 (4H, m), 2.02-2.05 (2H, m), 2.54-2.55 (2H, m), 2.63-2.67 (2H, m), 3.14-3.16 (1H, m), 4.07 (2H, t, J=6.5 Hz), 5.81 (1H, m), 6.97-6.99 (2H, m), 7.10-7.16 (2H, m), 7.42-7.44 (2H, m), 7.48-7.52 (1H, m), 7.69-7.71 (1H, m)
ESI-MS (m/e): 386.3 [M+H]⁺

Example 16

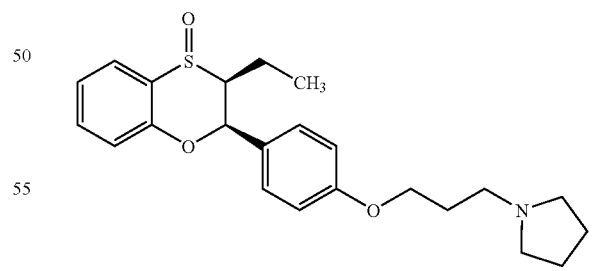

Synthesis of (2,3-cis)-2,3-dihydro-3-ethyl-2-[4-[3-(1-pyrrolidinyl)propoxy]phenyl]-1,4-benzoxathiin-4-oxide The entitled compound was obtained according to the method of Example 15 but using the compound synthesized in Example 8 as the starting material.

¹HNMR (400 MHz, CDCl₃, δ): 0.90 (3H, t, J=7.4 Hz), 1.00-1.08 (1H, m), 1.63-1.82 (5H, m), 2.00-2.07 (2H, m), 2.53-2.56 (4H, m), 2.63-2.67 (2H, m), 2.95-2.99 (1H, m), 4.07 (2H, t, J=6.5 Hz), 5.83 (1H, m), 6.96-7.00 (2H, m), 7.10-7.16 (2H, m), 7.42-7.52 (3H, m), 7.70-7.72 (1H, m)

ESI-MS (m/e): 400.2 [M+H]⁺

Example 17

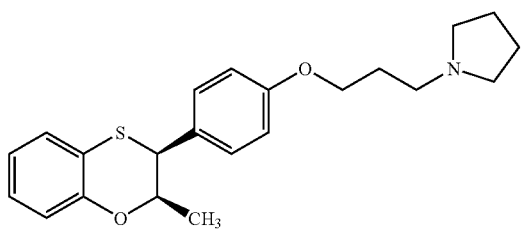

Synthesis of (2,3-cis)-2,3-dihydro-2-methyl-3-[4-[3-(1-pyrrolidinyl)propoxy]phenyl]-1,4-benzoxathiin The entitled compound was obtained according to the method of Example 3 but using 4-[(2,3-cis)-2-methyl-2,3-dihydro-1,4-benzoxathiin-3-yl]phenol synthesized in Reference Example 4-1 and 1-(3-hydroxypropyl)pyrrolidine as the starting material.

¹HNMR (400 MHz, CDCl₃, δ): 1.22 (3H, d, J=6.4 Hz), 1.77-1.80 (4H, m), 1.97-2.01 (2H, m), 2.51-2.54 (4H, m), 2.59-2.63 (2H, m), 3.98-4.02 (2H, m), 4.28 (1H, d, J=2.3 Hz), 4.57 (1H, dd, J=2.3 Hz, 6.4 Hz), 6.82-6.92 (4H, m), 7.00-7.11 (2H, m), 7.18-7.20 (2H, m)

ESI-MS (m/e): 370.2 [M+H]⁺

Example 18

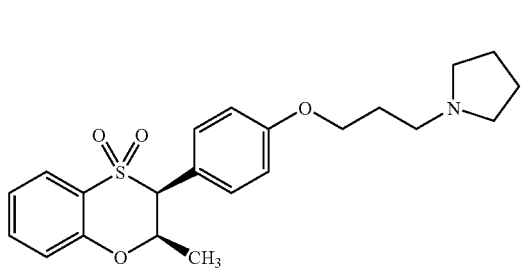

Synthesis of (2,3-cis)-2,3-dihydro-2-methyl-3-[4-[3-(1-pyrrolidinyl)propoxy]phenyl]-1,4-benzoxathiin-4,4-dioxide The entitled compound was obtained according to the method of Example 9 but using the compound synthesized in Example 17 as the starting material.

¹HNMR (400 MHz, CDCl₃, δ): 1.46 (3H, d, J=6.5 Hz), 1.71-1.79 (4H, m), 1.95-1.99 (2H, m), 2.49-2.60 (6H, m), 3.96-3.99 (2H, m), 4.14 (1H, d, J=2.3 Hz), 5.43 (1H, dd, J=2.2 Hz, 6.5 Hz), 7.06-7.17 (4H, m), 7.49-7.53 (1H, m), 7.79-7.81 (1H, m)

ESI-MS (m/e): 402.2 [M+H]⁺

Example 19

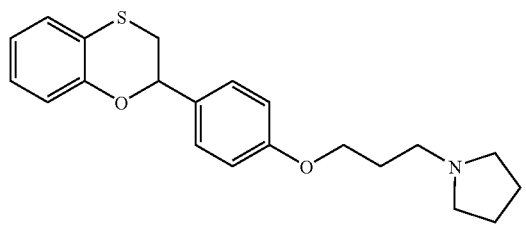

Synthesis of 2,3-dihydro-2-[4-[3-(1-pyrrolidinyl)propoxy]phenyl]-1,4-benzoxathiin The entitled compound was obtained according to the method of Example 3 but using 4-(2,3-dihydro-1,4-benzoxathiin-2-yl)phenol synthesized in Reference Example 2-4 and 1-(3-hydroxypropyl)pyrrolidine as the starting material.

¹HNMR (400 MHz, CDCl₃, δ): 1.78-1.82 (4H, m), 2.00-2.04 (2H, m), 2.53-2.56 (4H, m), 2.61-2.66 (2H, m), 3.04 (1H, dd, J=2.0 Hz, 13.1 Hz), 3.25-3.31 (1H, m), 4.03-4.06 (2H, m), 5.13 (1H, dd, J=1.8 Hz, 9.6 Hz), 6.86-7.02 (5H, m), 7.09-7.12 (1H, m), 7.31-7.33 (2H, m)

ESI-MS (m/e): 356.2 [M+H]⁺

Example 20

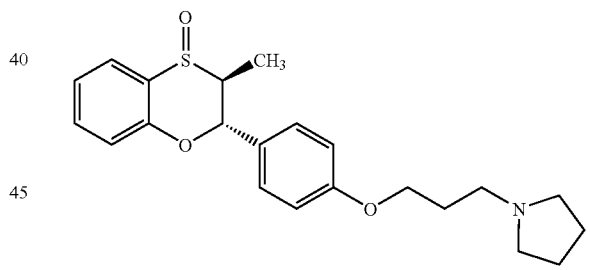

Synthesis of (2,3-trans)-2,3-dihydro-3-methyl-2-[4-[3-(1-pyrrolidinyl)propoxy]phenyl]-1,4-benzoxathiin-4-oxide The entitled compound was obtained according to the method of Example 15 but using the compound synthesized in Example 11 as the starting material.

¹HNMR (400 MHz, CDCl₃, δ): 1.19 (3H, d, J=7.0 Hz), 1.80-1.84 (4H, m), 2.03-2.07 (2H, m), 2.58-2.62 (4H, m), 2.65-2.69 (2H, m), 3.06-3.11 (1H, m), 4.07 (2H, t, J=6.4 Hz), 5.36 (2H, d, J=10.6 Hz), 6.96-6.98 (2H, m), 7.02-7.11 (2H, m), 7.35-7.37 (2H, m), 7.44-7.48 (1H, m), 7.68-7.70 (1H, m)

ESI-MS (m/e): 386.3 [M+H]⁺

Example 21

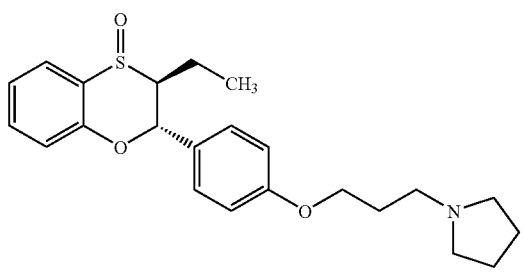

Synthesis of (2,3-trans)-2,3-dihydro-3-ethyl-2-[4-[3-(1-pyrrolidinyl)propoxy]phenyl]-1,4-benzoxathiin-4-oxide The entitled compound was obtained according to the method of Example 15 but using the compound synthesized in Example 12 as the starting material.

$^1$HNMR (400 MHz, CDCl$_3$, δ): 1.08 (3H, t, J=7.4 Hz), 1.25-1.27 (1H, m), 1.68-1.82 (5H, m), 2.01-2.05 (2H, m), 2.53-2.56 (4H, m), 2.62-2.66 (2H, m), 2.81-2.87 (1H, m), 4.07 (2H, t, J=6.5 Hz), 5.39 (1H, d, J=10.6 Hz), 6.95-7.11 (4H, m), 7.30-7.48 (3H, m), 7.70-7.72 (1H, m)

ESI-MS (m/e): 400.2 [M+H]$^+$

Example 22

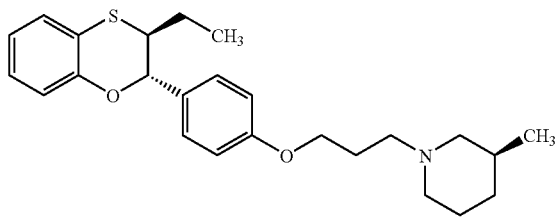

Synthesis of (2,3-trans)-2,3-dihydro-3-ethyl-2-[4-[3-((3S)-3-methyl-1-piperidinyl)propoxy]phenyl]-1,4-benzoxathiin The entitled compound was obtained according to the method of Example 3 but using the compound synthesized in Reference Example 3-2 and the compound synthesized in Reference Example 7 as the starting material.

$^1$HNMR (400 MHz, CDCl$_3$, δ): 0.87 (3H, d, J=6.5 Hz), 0.91-0.96 (3H, m), 1.33-1.41 (1H, m), 1.48-1.87 (8H, m), 1.95-2.02 (2H, m), 2.45-2.49 (2H, m), 2.81-2.88 (2H, m), 3.33-3.38 (1H, m), 4.02 (2H, t, J=6.4 Hz), 4.78 (1H, d, J=8.2 Hz), 6.85-7.01 (5H, m), 7.10-7.12 (1H, m), 7.23-7.26 (2H, m)

ESI-MS (m/e): 412.3 [M+H]$^+$

Example 23

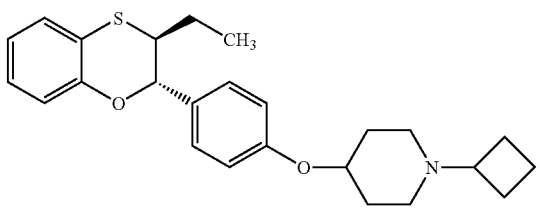

Synthesis of (2,3-trans)-2,3-dihydro-3-ethyl-2-[4-[(1-cyclobutylpiperidin-4-yl)oxy]phenyl]-1,4-benzoxathiin (1) Synthesis of t-butyl 4-{4-[(2,3-trans)-3-ethyl-2,3-dihydro-1,4-benzoxathiin-2-yl]phenoxy}piperidine-1-carboxylate The compound (445 mg, 1.63 mmol) synthesized in Reference Example 3-2, N-(t-butoxycarbonyl)-4-piperidinol (673 mg), triphenyl phosphine (855 mg) were dissolved in THF (10 mL), and with cooling with ice, diisopropyl azodicarboxylate (664 μL) was added and stirred at room temperature for 13 hours. The reaction liquid was concentrated under reduced pressure, and the obtained residue was purified by silica gel column chromatography (hexane:ethyl acetate=85:15) to obtain the intended compound (595 mg, 71%).

$^1$HNMR (400 MHz, CDCl$_3$, δ): 0.95 (3H, t, J=7.4 Hz), 1.26-1.42 (2H, m), 1.47 (9H, s), 1.74-1.78 (2H, m), 1.90-1.94 (2H, m), 3.32-3.38 (3H, m), 3.67-3.73 (2H, m), 4.47-4.49 (1H, m), 4.78 (1H, d, J=8.4 Hz), 6.85-7.01 (5H, m), 7.10-7.12 (1H, m), 7.24-7.27 (2H, m)

ESI-MS (m/e): 456.2 [M+H]$^+$ (2) Synthesis of 4-{4-[(2,3-trans)-3-ethyl-2,3-dihydro-1,4-benzoxathiin-2-yl]phenoxy}piperidine Anisole (345 μL) and trifluoroacetic acid (15 mL) were added to a dichloromethane (10 mL) solution of the compound (578 mg, 1.27 mmol) obtained in the above (1), and stirred at room temperature for 3 hours. The reaction liquid was concentrated under reduced pressure, and the residue was dissolved in chloroform, and extracted with saturated sodium hydrogencarbonate. The aqueous layer was back-extracted three times with chloroform, then the organic layer was collected and dried with magnesium sulfate, and concentrated under reduced pressure to obtain a crude product (398 mg) of the intended compound as a yellow oil.

(3) Synthesis of the Entitled Compound

A methanol solution (3 mL) of 0.3 N sodium cyanoborohydride/0.15 N zinc(II) chloride was added to a methanol (7 mL) solution of the compound (215 mg) synthesized in the above (2) and cyclobutanone (63.6 mg), and stirred at room temperature for 12 hours. The solvent was concentrated under reduced pressure, then extracted with distilled water and chloroform added thereto. The organic layer was dried with magnesium sulfate and then concentrated under reduced pressure. The obtained residue was purified by silica gel column chromatography (chloroform:methanol=100:6), and the obtained crude product of the intended compound was purified by reversed-phase HPLC (0.1% TFA acetonitrile:H$_2$O=10% to 95%, gradient) to obtain the entitled compound (70 mg, 29% in 2 steps).

$^1$HNMR (400 MHz, CDCl$_3$, δ): 0.95 (3H, t, J=7.4 Hz), 1.33-1.58 (2H, m), 1.68-2.17 (12H, m), 2.62-2.75 (3H, m), 3.35-3.36 (1H, m), 4.15-4.20 (1H, m), 4.77 (1H, d, J=8.2 Hz), 6.80-6.82 (1H, m), 6.86-6.99 (4H, m), 7.09-7.12 (1H, m), 7.23-7.25 (2H, m)

ESI-MS (m/e): 410.3 [M+H]$^+$

Example 24

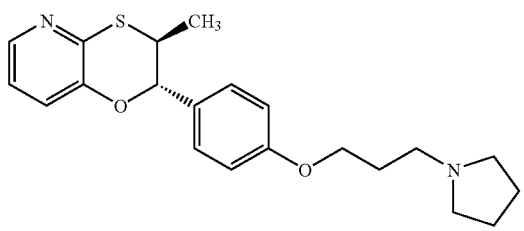

Synthesis of (2,3-trans)-2,3-dihydro-3-methyl-2-[4-[3-(1-pyrrolidinyl)propoxy]phenyl]-[1,4]oxathiino[3,2-b]pyridine The entitled compound was obtained according to the method of Example 3 but using 4-[(2,3-trans)-3-methyl-2,3-dihydro[1,4]oxathiino[3,2-b]pyridin-2-yl]phenol synthesized in Reference Example 5 and 1-(3-hydroxypropyl)pyrrolidine as the starting material.

$^1$HNMR (400 MHz, CDCl$_3$, δ): 1.10 (3H, d, J=6.8 Hz), 1.83-1.95 (4H, m), 2.12-2.16 (2H, m), 2.76-2.84 (6H, m), 3.59-3.63 (1H, m), 4.07 (2H, t, J=6.3 Hz), 4.67 (1H, d, J=8.8 Hz), 6.92-6.95 (3H, m), 7.10-7.12 (1H, m), 7.25-7.27 (2H, m), 8.09-8.11 (1H, m)

ESI-MS (m/e): 371.2 [M+H]$^+$

Example 25

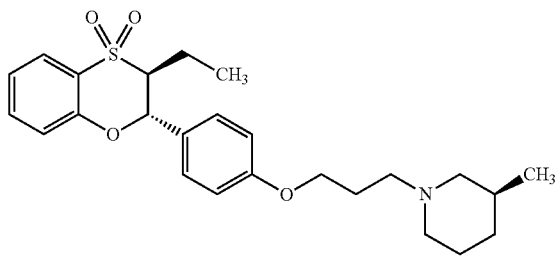

Synthesis of (2,3-trans)-2,3-dihydro-3-ethyl-2-[4-[3-((3S)-3-methyl-1-piperidinyl)propoxy]phenyl]-1,4-benzoxathiin-4,4-dioxide The entitled compound was obtained according to the method of Example 9 but using the compound synthesized in Example 22 as the starting material.

$^1$HNMR (400 MHz, CDCl$_3$, δ): 0.87 (3H, d, J=6.5 Hz), 0.97 (3H, t, J=7.5 Hz), 1.32-1.37 (1H, m), 1.53-1.72 (5H, m), 1.82-1.88 (2H, m), 1.97-2.06 (3H, m), 2.47-2.50 (2H, m), 2.82-2.89 (2H, m), 3.50-3.56 (1H, m), 4.05 (2H, t, J=6.4 Hz), 5.40 (1H, d, J=11.0 Hz), 6.96-6.98 (3H, m), 7.13-7.17 (1H, m), 7.32-7.34 (2H, m), 7.43-7.47 (1H, m), 7.83-7.86 (1H, m)

ESI-MS (m/e): 444.2 [M+H]$^+$

Example 26

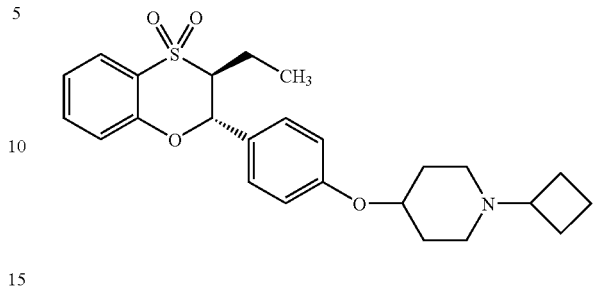

Synthesis of (2,3-trans)-2,3-dihydro-3-ethyl-2-[4-[(1-cyclobutylpiperidin-4-yl)oxy]phenyl]-1,4-benzoxathiin-4,4-dioxide The entitled compound was obtained according to the method of Example 9 but using (2,3-trans)-2,3-dihydro-3-ethyl-2-[4-[(1-cyclobutylpiperidin-4-yl)oxy]phenyl]-1,4-benzoxathiin synthesized in Example 23 as the starting material.

$^1$HNMR (400 MHz, CDCl$_3$, δ): 0.97 (3H, t, J=7.5 Hz), 1.32-1.39 (1H, m), 1.66-1.73 (2H, m), 1.83-2.08 (9H, m), 2.12-2.25 (2H, m), 2.64-2.77 (3H, m), 3.50-3.56 (1H, m), 4.32-4.44 (1H, m), 5.40 (1H, d, J=11.0 Hz), 6.96-6.98 (3H, m), 7.13-7.17 (1H, m), 7.31-7.33 (2H, m), 7.43-7.47 (1H, m), 7.83-7.86 (1H, m)

ESI-MS (m/e): 442.2 [M+H]$^+$

Example 27

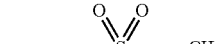

Optical resolution of (2,3-trans)-2,3-dihydro-3-methyl-2-[4-[3-(1-pyrrolidinyl)propoxy]phenyl]-1,4-benzoxathiin-4,4-dioxide The compound synthesized in Example 13 was optically resolved in normal-phase chiral HPLC (CHIRALPAK OJ 2 cmφ×25 cmL (by Daicel Chemical Industry), mobile phase: hexane/ethanol/diethylamine=70/30/0.1, flow rate: 10 ml/min, isogradient) to obtain (2S*,3S*)-2,3-dihydro-3-methyl-2-[4-[3-(1-pyrrolidinyl)propoxy]phenyl]-1,4-benzoxathiin-4,4-dioxide (retention time, 22.4 min) and (2R*,3R*)-2,3-dihydro-3-methyl-2-[4-[3-(1-pyrrolidinyl)propoxy]phenyl]-1,4-benzoxathiin-4,4-dioxide (retention time, 30.0 min).

Example 28

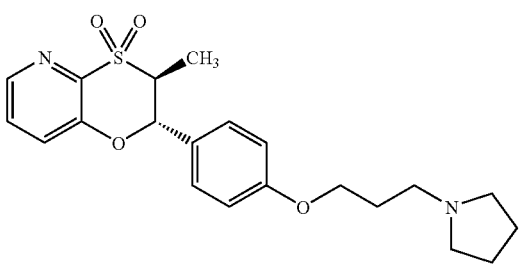

Synthesis of (2,3-trans)-2,3-dihydro-3-methyl-2-[4-[3-(1-pyrrolidinyl)propoxy]phenyl]-[1,4]oxathiino[3,2-b]pyridine-4,4-dioxide The entitled compound was obtained according to the method of Example 9 but using (2,3-trans)-2,3-dihydro-3-methyl-2-[4-[3-(1-pyrrolidinyl)propoxy]phenyl]-[1,4]oxathiino[3,2-b]pyridine synthesized in Example 24 as the starting material.

$^1$HNMR (400 MHz, CDCl$_3$, δ): 1.22 (3H, d, J=6.8 Hz), 1.77-1.84 (4H, m), 2.00-2.07 (2H, m), 2.50-2.59 (4H, m), 2.62-2.66 (2H, m), 3.78-3.86 (1H, m), 4.08 (2H, t, J=6.5 Hz), 5.44 (1H, d, J=10.8 Hz), 6.98-7.00 (2H, m), 7.30-7.33 (2H, m), 7.38-7.40 (1H, m), 7.45-7.48 (1H, m), 8.45-8.46 (1H, m)

ESI-MS (m/e): 403.1 [M+H]$^+$

Example 29

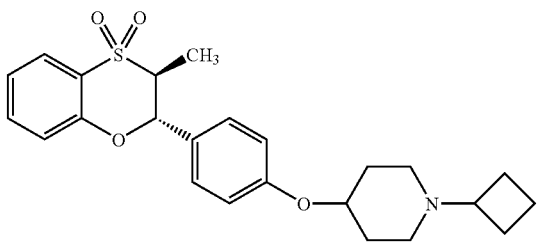

Synthesis of (2,3-trans)-2,3-dihydro-3-methyl-2-[4-[(1-cyclobutylpiperidin-4-yl)oxy]phenyl]-1,4-benzoxathiin-4,4-dioxide (1) Synthesis of (2,3-trans)-2,3-dihydro-3-methyl-2-[4-[(1-cyclobutylpiperidin-4-yl)oxy]phenyl]-1,4-benzoxathiin 4-[(2,3-Trans)-3-methyl-2,3-dihydro-1,4-benzoxathiin-2-yl]phenol (552 mg, 2.14 mmol) synthesized in Reference Example 3-1, 1-cyclobutylpiperidin-4-ol (979 mg) synthesized in Reference Example 6, and triphenyl phosphine (1.65 g) were dissolved in THF (11 mL), and with cooling with ice, diisopropyl azodicarboxylate (2.1 mL) was added, and stirred at room temperature for 19 hours. The reaction liquid was concentrated under reduced pressure, and the obtained residue was purified by NH silica gel column chromatography (hexane:ethyl acetate=85:15) and further by silica gel column chromatography (chloroform:methanol=20:1) to obtain a crude product of the intended compound (885 mg).

(2) Synthesis of the Entitled Compound

The entitled compound was obtained according to the method of Example 9 but using the crude product of the compound synthesized in the above (1) as the starting material.

$^1$HNMR (400 MHz, CDCl$_3$, δ): 1.18 (3H, d, J=6.8 Hz), 1.66-1.91 (6H, m), 1.93-2.05 (4H, m), 2.21-2.27 (2H, m), 2.55-2.70 (2H, m), 2.72-2.82 (1H, m), 3.66-3.70 (1H, m), 4.33-4.43 (1H, m), 5.40 (1H, d, J=11.0 Hz), 6.96-7.00 (3H, m), 7.14-7.18 (1H, m), 7.30-7.32 (2H, m), 7.45-7.49 (1H, m), 7.85-7.87 (1H, m)

ESI-MS (m/e): 428.2 [M+H]$^+$

Example 30

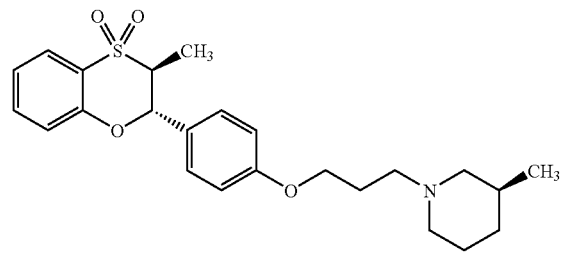

Synthesis of (2,3-trans)-2,3-dihydro-3-methyl-2-[4-[3-((3S)-3-methyl-1-piperidinyl)propoxy]phenyl]-1,4-benzoxathiin-4,4-dioxide The entitled compound was obtained according to the method of Example 3 and Example 9 but using 4-[(2,3-trans)-3-methyl-2,3-dihydro-1,4-benzoxathiin-2-yl]phenol synthesized in Reference Example 3-1 and the compound synthesized in Reference Example 7 as the starting material.

$^1$HNMR (400 MHz, CDCl$_3$, δ): 0.87 (3H, d, J=6.5 Hz), 1.17 (3H, d, J=6.8 Hz), 1.54-1.88 (7H, m), 1.97-2.04 (2H, m), 2.48-2.51 (2H, m), 2.83-2.90 (2H, m), 3.66-3.71 (1H, m), 4.05 (2H, t, J=6.4 Hz), 5.40 (1H, d, J=11.0 Hz), 6.96-7.00 (3H, m), 7.14-7.17 (1H, m), 7.31-7.33 (2H, m), 7.45-7.49 (1H, m), 7.85-7.87 (1H, m)

ESI-MS (m/e): 430.2 [M+H]$^+$

Example 31

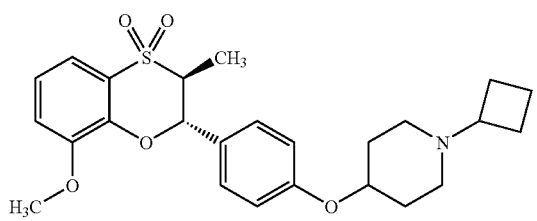

Synthesis of (2,3-trans)-2,3-dihydro-8-methoxy-3-methyl-2-[4-[(1-cyclobutylpiperidin-4-yl)oxy]phenyl]-1,4-benzoxathiin-4,4-dioxide The entitled compound was obtained according to the method of Example 29 but using 4-[(2,3-trans)-8-methoxy-3-methyl-2,3-dihydro-1,4-benzoxathiin-2-yl]phenol synthesized in Reference Example 8 and 1-cyclobutylpiperidin-4-ol synthesized in Reference Example 6 as the stating material.

$^1$HNMR (400 MHz, CDCl$_3$, δ): 1.17 (3H, d, J=7.3 Hz), 1.64-2.18 (12H, m), 2.59-2.67 (2H, m), 2.71-2.79 (1H, m), 3.62-3.70 (1H, m), 3.83 (3H, s), 4.34-4.39 (1H, m), 5.41 (1H, d, J=10.7 Hz), 6.94-6.97 (2H, m), 7.03 (1H, dd, J=8.3, 1.5 Hz), 7.11 (1H, t, J=8.0 Hz), 7.31-7.34 (2H, m), 7.44 (1H, dd, J=8.3, 1.5 Hz)

ESI-MS (m/e): 458.2 [M+H]$^+$

Example 32

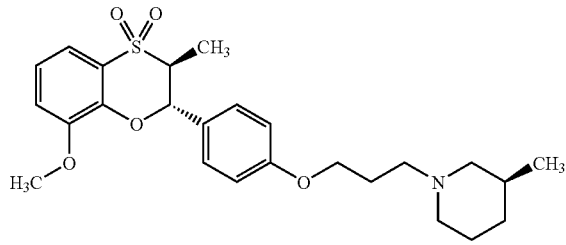

Synthesis of 1-[3-[4-[(2,3-trans)-2,3-dihydro-4,4-dioxido-8-methoxy-3-methyl-1,4-benzoxathiin-2-yl]phenoxy]propyl]-(3S)-3-methylpiperidine The entitled compound was obtained according to the method of Example 3 and Example 9 but using 4-[(2,3-trans)-8-methoxy-3-methyl-2,3-dihydro-1,4-benzoxathiin-2-yl]phenol synthesized in Reference Example 8 and 3-[(3S)-3-methylpiperidin-1-yl]propan-1-ol synthesized in Reference Example 7 as the stating material.

$^1$HNMR (400 MHz, CDCl$_3$, δ): 0.87-0.88 (4H, m), 1.17 (3H, d, J=7.3 Hz), 1.54-1.89 (6H, m), 1.97-2.05 (2H, m), 2.49 (2H, t, J=7.6 Hz), 2.87 (2H, d, J=28.3 Hz), 3.63-3.71 (1H, m), 3.82 (3H, s), 4.04 (2H, t, J=6.3 Hz), 5.41 (1H, d, J=10.7 Hz), 6.94-6.98 (2H, m), 7.03 (1H, dd, J=8.3, 1.5 Hz), 7.10 (1H, t, J=8.0 Hz), 7.31-7.35 (2H, m), 7.44 (1H, dd, J=8.0, 1.7 Hz)

ESI-MS (m/e): 460.2 [M+H]$^+$

Example 33

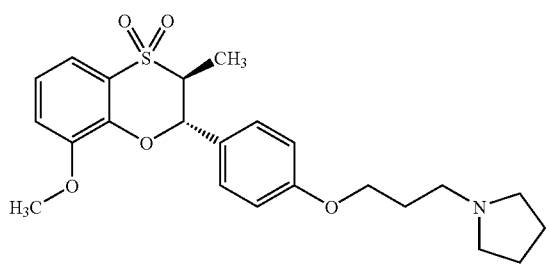

Synthesis of 1-[3-[4-[(2,3-trans)-2,3-dihydro-4,4-dioxido-8-methoxy-3-methyl-1,4-benzoxathiin-2-yl]phenoxy]propyl]-pyrrolidine The entitled compound was obtained according to the method of Example 3 and Example 9 but using 4-[(2,3-trans)-8-methoxy-3-methyl-2,3-dihydro-1,4-benzoxathiin-2-yl]phenol synthesized in Reference Example 8 and 1-(3-hydroxypropyl)pyrrolidine as the stating material.

$^1$HNMR (400 MHz, CDCl$_3$, δ): 1.17 (3H, d, J=6.8 Hz), 1.79-1.83 (4H, m), 2.00-2.07 (2H, m), 2.54-2.57 (4H, m), 2.65 (3H, t, J=7.3 Hz), 3.63-3.71 (1H, m), 3.82 (3H, s), 4.06 (2H, t, J=6.3 Hz), 5.41 (1H, d, J=11.2 Hz), 6.95-6.97 (2H, m), 7.03 (1H, dd, J=7.8, 1.5 Hz), 7.10 (1H, t, J=8.0 Hz), 7.33 (2H, d, J=8.8 Hz), 7.44 (1H, dd, J=7.8, 1.5 Hz)

ESI-MS (m/e): 432.2 [M+H]$^+$

Example 34

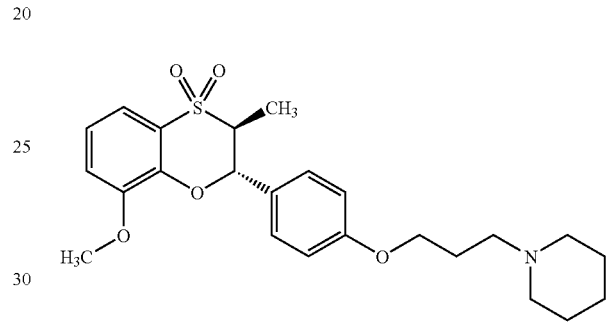

Synthesis of 1-[3-[4-[(2,3-trans)-2,3-dihydro-4,4-dioxido-8-methoxy-3-methyl-1,4-benzoxathiin-2-yl]phenoxy]propyl]-piperidine The entitled compound was obtained according to the method of Example 3 and Example 9 but using 4-[(2,3-trans)-8-methoxy-3-methyl-2,3-dihydro-1,4-benzoxathiin-2-yl]phenol synthesized in Reference Example 8 and 1-(3-hydroxypropyl)piperidine as the stating material.

$^1$HNMR (400 MHz, CDCl$_3$, δ): 1.17 (3H, d, J=6.8 Hz), 1.41-1.49 (2H, m), 1.54-1.65 (4H, m), 1.94-2.05 (2H, m), 2.34-2.54 (6H, m), 3.63-3.71 (1H, m), 3.82 (3H, s), 4.04 (2H, t, J=6.3 Hz), 5.41 (1H, d, J=11.2 Hz), 6.94-6.97 (2H, m), 7.03 (1H, dd, J=7.8, 1.5 Hz), 7.07-7.13 (1H, m), 7.30-7.36 (2H, m), 7.44 (1H, dd, J=7.8, 1.5 Hz)

ESI-MS (m/e): 446.1 [M+H]$^+$

Example 35

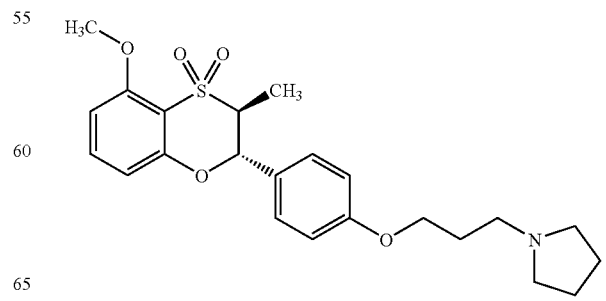

Synthesis of 1-[3-[4-[(2,3-trans)-2,3-dihydro-4,4-dioxido-5-methoxy-3-methyl-1,4-benzoxathiin-2-yl]phenoxy]propyl]-pyrrolidine The entitled compound was obtained according to the method of Example 3 and Example 9 but using 4-[(2,3-trans)-5-methoxy-3-methyl-2,3-dihydro-1,4-benzoxathiin-2-yl]phenol synthesized in Reference Example 9 and 1-(3-hydroxypropyl)pyrrolidine as the stating material.

¹HNMR (400 MHz, CDCl₃, δ): 1.15 (3H, d, J=6.8 Hz), 1.77-1.86 (4H, m), 2.01-2.08 (2H, m), 2.53-2.60 (4H, m), 2.67 (2H, t, J=7.6 Hz), 3.66-3.74 (1H, m), 3.99 (3H, s), 4.07 (2H, t, J=6.3 Hz), 5.27 (1H, d, J=11.2 Hz), 6.56-6.62 (2H, m), 6.95-6.98 (2H, m), 7.28-7.36 (3H, m)

ESI-MS (m/e): 432.1 [M+H]⁺

Example 36

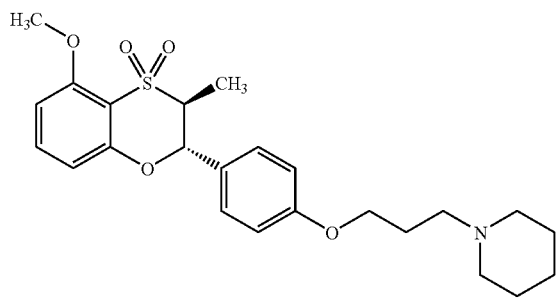

Synthesis of 1-[3-[4-[(2,3-trans)-2,3-dihydro-4,4-dioxido-5-methoxy-3-methyl-1,4-benzoxathiin-2-yl]phenoxy]propyl]-piperidine The entitled compound was obtained according to the method of Example 3 and Example 9 but using 4-[(2,3-trans)-5-methoxy-3-methyl-2,3-dihydro-1,4-benzoxathiin-2-yl]phenol synthesized in Reference Example 9 and 1-(3-hydroxypropyl)piperidine as the stating material.

¹HNMR (400 MHz, CDCl₃, δ): 1.15 (3H, d, J=6.8 Hz), 1.40-1.49 (2H, m), 1.55-1.64 (4H, m), 1.97-2.04 (2H, m), 2.34-2.53 (6H, m), 3.65-3.75 (1H, m), 3.99 (3H, s), 4.04 (2H, t, J=6.3 Hz), 5.26 (1H, d, J=10.7 Hz), 6.55-6.63 (2H, m), 6.94-6.99 (2H, m), 7.28-7.36 (3H, m)

ESI-MS (m/e): 446.2 [M+H]⁺

Example 37

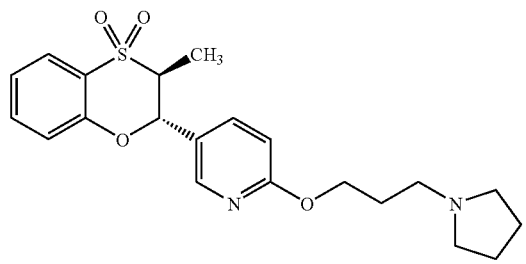

Synthesis of 1-[3-[5-[(2,3-trans)-2,3-dihydro-4,4-dioxido-3-methyl-1,4-benzoxathiin-2-yl]pyridin-2-yloxy]propyl]-pyrrolidine The entitled compound was obtained according to the method of Example 3 and Example 9 but using 5-[(2,3-trans)-3-methyl-2,3-dihydro-1,4-benzoxathiin-2-yl]pyridin-2-ol synthesized in Reference Example 12 and 1-(3-hydroxypropyl)pyrrolidine as the stating material.

¹HNMR (400 MHz, CDCl₃, δ): 1.21 (3H, d, J=7.3 Hz), 1.77-1.84 (4H, m), 2.00-2.08 (2H, m), 2.51-2.60 (4H, m), 2.64 (2H, t, J=7.6 Hz), 3.64-3.73 (1H, m), 4.40 (2H, t, J=6.6 Hz), 5.44 (1H, d, J=11.2 Hz), 6.84 (1H, d, J=8.8 Hz), 6.99 (1H, dd, J=8.3, 1.0 Hz), 7.15-7.20 (1H, m), 7.46-7.51 (1H, m), 7.63 (1H, dd, J=8.5, 2.7 Hz), 7.87 (1H, dd, J=8.0, 1.7 Hz), 8.17 (1H, d, J=2.4 Hz)

ESI-MS (m/e): 403.1 [M+H]⁺

Example 38

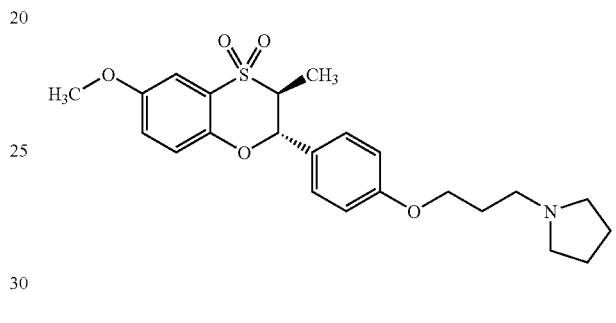

Synthesis of 1-[3-[4-[(2,3-trans)-2,3-dihydro-4,4-dioxido-6-methoxy-3-methyl-1,4-benzoxathiin-2-yl]phenoxy]propyl]-pyrrolidine The entitled compound was obtained according to the method of Example 3 and Example 9 but using the compound synthesized in Reference Example 10 and 1-(3-hydroxypropyl)pyrrolidine as the stating material.

¹HNMR (400 MHz, CDCl₃, δ): 1.17 (3H, d, J=6.8 Hz), 1.77-1.85 (4H, m), 1.99-2.08 (2H, m), 2.51-2.58 (4H, m), 2.61-2.68 (2H, m), 3.62-3.72 (1H, m), 3.84 (3H, s), 4.07 (2H, t, J=6.3 Hz), 5.33 (1H, d, J=10.7 Hz), 6.90-7.00 (3H, m), 7.05 (1H, dd, J=9.3, 2.9 Hz), 7.25-7.27 (1H, m), 7.29-7.33 (2H, m)

APCI-MS (m/e): 432.0 [M+H]⁺

Example 39

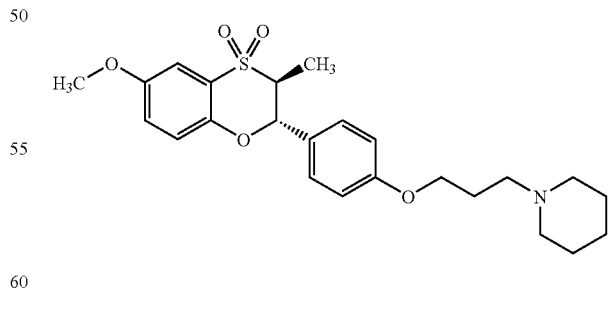

Synthesis of 1-[3-[4-[(2,3-trans)-2,3-dihydro-4,4-dioxido-6-methoxy-3-methyl-1,4-benzoxathiin-2-yl]phenoxy]propyl]-piperidine The entitled compound was obtained according to the method of Example 3 and Example 9 but using the compound synthesized in Reference Example 10 and 1-(3-hydroxypropyl)piperidine as the stating material.

¹HNMR (400 MHz, CDCl₃, δ): 1.17 (3H, d, J=7.3 Hz), 1.55-1.76 (6H, m), 1.96-2.05 (2H, m), 2.34-2.53 (6H, m), 3.62-3.71 (1H, m), 3.84 (3H, s), 4.04 (2H, t, J=6.3 Hz), 5.33 (1H, d, J=11.2 Hz), 6.90-6.99 (3H, m), 7.05 (1H, dd, J=9.0, 3.2 Hz), 7.26 (1H, d, J=2.0 Hz), 7.29-7.33 (2H, m)

APCI-MS (m/e): 446.1 [M+H]⁺

Example 40

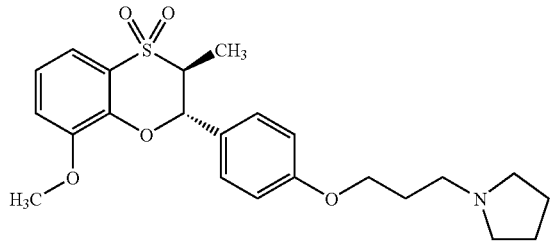

Optical resolution of 1-[3-[4-[(2,3-trans)-2,3-dihydro-4,4-dioxido-8-methoxy-3-Methyl-1,4-benzoxathiin-2-yl]phenoxy]propyl]-pyrrolidine The compound synthesized in Example 33 was optically resolved in normal-phase chiral HPLC (CHIRALPAK AD-H 2 cmφ×25 cmL (Daicel Chemical Industry), mobile phase: hexane/isopropyl alcohol/diethylamine=55/45/0.1, flow rate: 7 ml/min, isogradient) to obtain 1-[3-[4-[(2S*,3S*)-2,3-dihydro-4,4-dioxido-8-methoxy-3-methyl-1,4-benzoxathiin-2-yl]phenoxy]propyl]-pyrrolidine (retention time: 24.9 min) and 1-[3-[4-[(2R*,3R*)-2,3-dihydro-4,4-dioxido-8-methoxy-3-methyl-1,4-benzoxathiin-2-yl]phenoxy]propyl]-pyrrolidine (retention time: 35.1 min).

Example 41

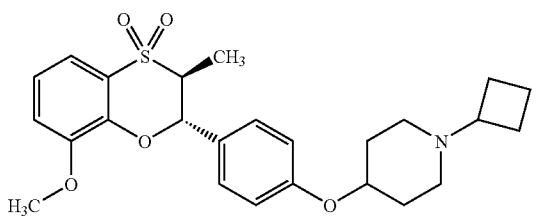

Optical resolution of (2,3-trans)-2,3-dihydro-8-methoxy-3-methyl-2-[4-[(1-cyclobutylpiperidin-4-yl)oxy]phenyl]-1,4-benzoxathiin-4,4-dioxide The compound synthesized in Example 31 was optically resolved in normal-phase chiral HPLC (CHIRALPAK AD-H 2 cmφ×25 cmL (Daicel Chemical Industry), mobile phase: hexane/isopropyl alcohol/diethylamine=50/50/0.1, flow rate: 7 ml/min, isogradient) to obtain (2R*,3R*)-2,3-dihydro-8-methoxy-3-methyl-2-[4-[(1-cyclobutylpiperidin-4-yl)oxy]phenyl]-1,4-benzoxathiin-4,4-dioxide (retention time: 24.5 min) and (2S*,3S*)-2,3-dihydro-8-methoxy-3-methyl-2-[4-[(1-cyclobutylpiperidin-4-yl)oxy]phenyl]-1,4-benzoxathiin-4,4-dioxide (retention time: 38.8 min).

Example 42

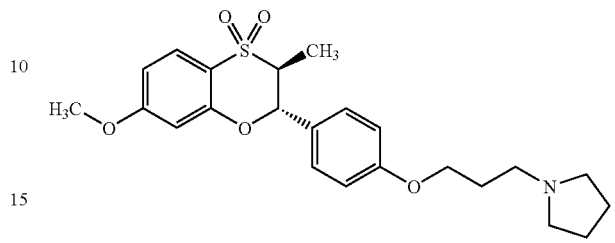

Synthesis of 1-[3-[4-[(2,3-trans)-2,3-dihydro-4,4-dioxido-7-methoxy-3-methyl-1,4-benzoxathiin-2-yl]phenoxy]propyl]-pyrrolidine The entitled compound was obtained according to the method of Example 3 and Example 9 but using the compound synthesized in Reference Example 11 and 1-(3-hydroxypropyl)pyrrolidine as the starting material.

¹HNMR (400 MHz, CDCl₃, δ): 1.15 (3H, d, J=6.8 Hz), 1.76-1.85 (4H, m), 1.99-2.08 (2H, m), 2.49-2.59 (4H, m), 2.65 (2H, t, J=7.3 Hz), 3.59-3.69 (1H, m), 3.79 (3H, s), 4.07 (2H, t, J=6.3 Hz), 5.40 (1H, d, J=10.7 Hz), 6.45 (1H, d, J=2.0 Hz), 6.71 (1H, dd, J=8.8, 2.4 Hz), 6.95-7.00 (2H, m), 7.29-7.34 (2H, m), 7.75 (1H, d, J=9.3 Hz)

APCI-MS (m/e): 432.0 [M+H]⁺

Example 43

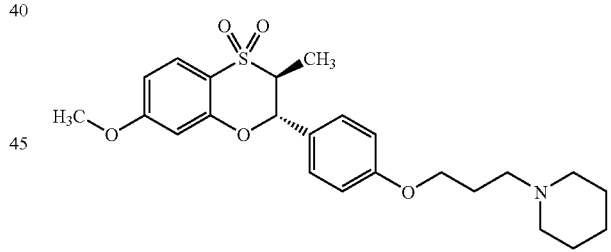

Synthesis of 1-[3-[4-[(2,3-trans)-2,3-dihydro-4,4-dioxido-7-methoxy-3-methyl-1,4-benzoxathiin-2-yl]phenoxy]propyl]-piperidine The entitled compound was obtained according to the method of Example 3 and Example 9 but using the compound synthesized in Reference Example 11 and 1-(3-hydroxypropyl)piperidine as the starting material.

¹HNMR (400 MHz, CDCl₃, δ): 1.16 (3H, d, J=6.8 Hz), 1.54-1.70 (8H, m), 1.96-2.04 (2H, m), 2.35-2.53 (6H, m), 3.60-3.70 (1H, m), 3.79 (3H, s), 4.04 (2H, t, J=6.3 Hz), 5.40 (1H, d, J=10.7 Hz), 6.45 (1H, d, J=2.4 Hz), 6.71 (1H, dd, J=8.8, 2.4 Hz), 6.94-6.99 (2H, m), 7.28-7.33 (2H, m), 7.75 (1H, d, J=8.8 Hz)

APCI-MS (m/e): 446.1 [M+H]⁺

Example 44

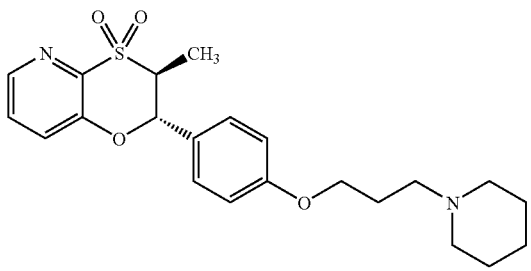

Synthesis of 1-[3-[4-[(2,3-trans)-2,3-dihydro-4,4-dioxido-3-methyl-[1,4]oxathiino[3,2-b]pyridin-2-yl]phenoxy]propyl]-piperidine The entitled compound was obtained according to the method of Example 3 and Example 9 but using 4-[(2,3-trans)-3-methyl-2,3-dihydro[1,4]oxathiino[3,2-b]pyridin-2-yl]phenol synthesized in Reference Example 5 and 1-(3-hydroxypropyl)piperidine as the starting material.

$^{1}$HNMR (400 MHz, CDCl$_{3}$, δ): 1.22 (3H, d, J=6.8 Hz), 1.56-1.71 (6H, m), 1.96-2.06 (2H, m), 2.33-2.55 (6H, m), 3.76-3.86 (1H, m), 4.05 (2H, t, J=6.3 Hz), 5.44 (1H, d, J=10.7 Hz), 6.96-7.01 (2H, m), 7.29-7.33 (2H, m), 7.37-7.41 (1H, m), 7.44-7.48 (1H, m), 8.44-8.47 (1H, m).

APCI-MS (m/e): 417.0 [M+H]$^{+}$

Example 45

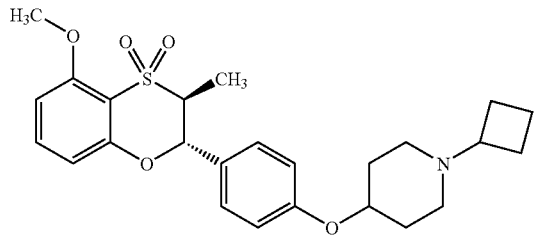

Synthesis of (2,3-trans)-2,3-dihydro-5-methoxy-3-methyl-2-[4-[(1-cyclobutylpiperidin-4-yl)oxy]phenyl]-1,4-benzoxathiin-4,4-dioxide The entitled compound was obtained according to the method of Example 29 but using 4-[(2,3-trans)-5-methoxy-3-methyl-2,3-dihydro-1,4-benzoxathiin-2-yl]phenol synthesized in Reference Example 9 and 1-cyclobutylpiperidin-4-ol synthesized in Reference Example 6 as the starting material.

$^{1}$HNMR (400 MHz, CDCl$_{3}$, δ): 1.15 (3H, d, J=6.8 Hz), 1.57-2.25 (12H, m), 2.57-2.68 (2H, m), 2.70-2.80 (1H, m), 3.65-3.74 (1H, m), 3.99 (3H, s), 4.32-4.41 (1H, m), 5.26 (1H, d, J=11.2 Hz), 6.56-6.63 (2H, m), 6.94-6.98 (2H, m), 7.28-7.37 (3H, m)

ESI-MS (m/e): 458.2 [M+H]$^{+}$

Example 46

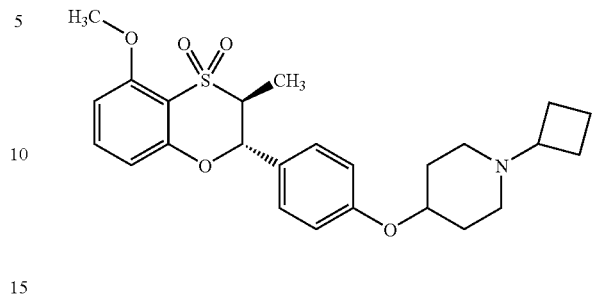

Optical resolution of (2,3-trans)-2,3-dihydro-5-methoxy-3-methyl-2-[4-[(1-cyclobutylpiperidin-4-yl)oxy]phenyl]-1,4-benzoxathiin-4,4-dioxide The compound synthesized in Example 45 was optically resolved in normal-phase chiral HPLC (CHIRALPAK AD-H 2 cmφ×25 cmL (by Daicel Chemical Industry), mobile phase: hexane/ethanol/diethylamine=60/40/0.1, flow rate: 10 ml/min, isogradient) to obtain (2R*,3R*)-2,3-dihydro-5-methoxy-3-methyl-2-[4-[(1-cyclobutylpiperidin-4-yl)oxy]phenyl]-1,4-benzoxathiin-4,4-dioxide (retention time: 20.5 min) and (2S*,3S*)-2,3-dihydro-5-methoxy-3-methyl-2-[4-[(1-cyclobutylpiperidin-4-yl)oxy]phenyl]-1,4-benzoxathiin-4,4-dioxide (retention time: 27.3 min).

Example 47

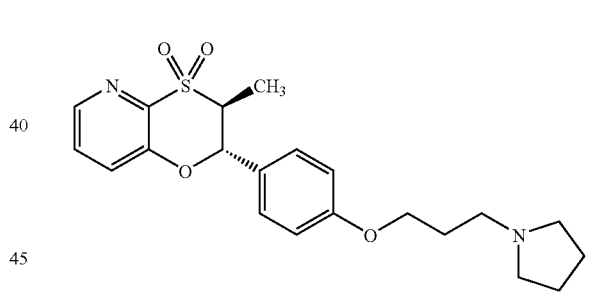

Synthesis of (2S*,3S*)-2,3-dihydro-3-methyl-2-[4-[3-(1-pyrrolidinyl)propoxy]phenyl]-[1,4]oxathiino[3,2-b]pyridin-4,4-dioxide and (2R*,3R*)-2,3-dihydro-3-methyl-2-[4-[3-(1-pyrrolidinyl)propoxy]phenyl]-[1,4]oxathiino[3,2-b]pyridin-4,4-dioxide (1) Optical resolution of (2,3-trans)-2,3-dihydro-3-methyl-2-[4-[3-(1-pyrrolidinyl)propoxy]phenyl]-[1,4]oxathiino[3,2-b]pyridine The compound synthesized in Example 24 was optically resolved in normal-phase chiral HPLC (CHIRALPAK OJ 2 cmφ×25 cmL (by Daicel Chemical Industry), mobile phase: hexane/ethanol/diethylamine=75/25/0.1, flow rate: 10 ml/min, isogradient) to obtain (2S*,3S*)-2,3-dihydro-3-methyl-2-[4-[3-(1-pyrrolidinyl)propoxy]phenyl]-[1,4]oxathiino[3,2-b]pyridine (retention time: 19.7 min) and (2R*, 3R*)-2,3-dihydro-3-methyl-2-[4-[3-(1-pyrrolidinyl)propoxy]phenyl]-[1,4]oxathiino[3,2-b]pyridine (retention time: 23.7 min).

(2) Synthesis of the Entitled Compound

The entitled compound was obtained according to the method of Example 9 but using (2S*,3S*)-2,3-dihydro-3-methyl-2-[4-[3-(1-pyrrolidinyl)propoxy]phenyl]-[1,4]oxathiino[3,2-b]pyridine or (2R*,3R*)-2,3-dihydro-3-methyl-2-[4-[3-(1-pyrrolidinyl)propoxy]phenyl]-[1,4]oxathiino[3,2-b]pyridine synthesized in the above (1) as the starting material.

Example 48

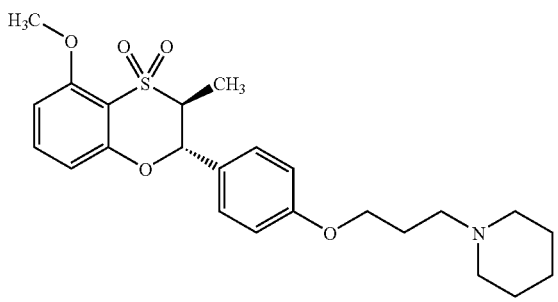

Optical resolution of 1-[3-[4-[(2,3-trans)-2,3-dihydro-4,4-dioxido-5-methoxy-3-methyl-1,4-benzoxathiin-2-yl]phenoxy]propyl]-piperidine The compound synthesized in Example 36 was optically resolved in normal-phase chiral HPLC (CHIRALPAK OJ, 2 cmφ×25 cmL (by Daicel Chemical Industry), mobile phase: hexane/ethanol/diethylamine=60/40/0.1, flow rate: 10 ml/min, isogradient) to obtain 1-[3-[4-[(2S*,3S*)-2,3-dihydro-4,4-dioxido-5-methoxy-3-methyl-1,4-benzoxathiin-2-yl]phenoxy]propyl]-piperidine (retention time: 19.9 min) and 1-[3-[4-[(2R*,3R*)-2,3-dihydro-4,4-dioxido-5-methoxy-3-methyl-1,4-benzoxathiin-2-yl]phenoxy]propyl]-piperidine (retention time: 30.3 min).

Example 49

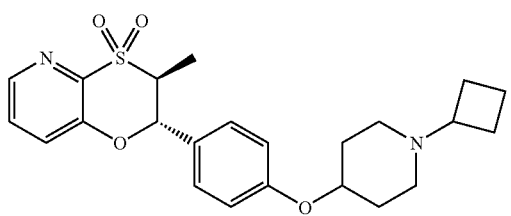

Synthesis of (2R*,3R*)-2-{4-[(1-cyclobutylpiperidin-4-yl)oxy]phenyl}-3-methyl-2,3-dihydro[1,4]oxathiino[3,2-b]pyridine 4,4-dioxide and (2S*,3S*)-2-{4-[(1-cyclobutylpiperidin-4-yl)oxy]phenyl}-3-methyl-2,3-dihydro[1,4]oxathiino[3,2-b]pyridine 4,4-dioxide (1) Synthesis of (2,3-trans)-2-{4-[(1-cyclobutylpiperidin-4-yl)oxy]phenyl}-3-methyl-2,3-dihydro[1,4]oxathiino[3,2-b]pyridine A crude product of the intended compound was obtained according to the method of Example 29 but using 4-[(2,3-trans)-3-methyl-2,3-dihydro[1,4]oxathiino[3,2-b]pyridin-2-yl]phenol synthesized in Reference Example 5 and 1-cyclobutylpiperidin-4-ol synthesized in Reference Example 6 as the starting material.

(2) Optical resolution of (2,3-trans)-2-{4-[(1-cyclobutylpiperidin-4-yl)oxy]phenyl}-3-methyl-2,3-dihydro[1,4]oxathiino[3,2-b]pyridine The compound synthesized in the above (1) was optically resolved in normal-phase chiral HPLC (CHIRALPAK AD-H, 2 cmφ×25 cmL (by Daicel Chemical Industry), mobile phase: hexane/ethanol/diethylamine=60/40/0.1, flow rate: 10 ml/min, isogradient) to obtain (2R*,3R*)-2-{4-[(1-cyclobutylpiperidin-4-yl)oxy]phenyl}-3-methyl-2,3-dihydro[1,4]oxathiino[3,2-b]pyridine (retention time: 15.2 min) and (2S*,3S*)-2-{4-[(1-cyclobutylpiperidin-4-yl)oxy]phenyl}-3-methyl-2,3-dihydro[1,4]oxathiino[3,2-b]pyridine (retention time: 19.0 min).

$^1$HNMR (400 MHz, CDCl$_3$, δ): 1.10 (3H, d, J=6.8 Hz), 1.59-2.10 (10H, m), 2.12-2.33 (2H, m), 2.55-2.70 (2H, m), 2.72-2.83 (1H, m), 3.55-3.65 (1H, m), 4.30-4.43 (1H, m), 4.67 (1H, d, J=8.8 Hz), 6.91-6.98 (3H, m), 7.08-7.13 (1H, m), 7.22-7.30 (2H, m), 8.07-8.12 (1H, m)

APCI-MS (m/e): 397.1 [M+H]$^+$ (3) Synthesis of the Entitled Compound

The entitled compound was obtained according to the method of Example 9 but using (2R*,3R*)-2-{4-[(1-cyclobutylpiperidin-4-yl)oxy]phenyl}-3-methyl-2,3-dihydro[1,4]oxathiino[3,2-b]pyridine or (2S*,3S*)-2-{4-[(1-cyclobutylpiperidin-4-yl)oxy]phenyl}-3-methyl-2,3-dihydro[1,4]oxathiino[3,2-b]pyridine obtained in the above (2) as the starting material.

$^1$HNMR (400 MHz, CDCl$_3$, δ): 1.22 (3H, d, J=6.8 Hz), 1.46-2.50 (12H, m), 2.62-2.76 (2H, m), 2.78-2.94 (1H, m), 3.76-3.86 (1H, m), 4.37-4.51 (1H, m), 5.44 (1H, d, J=11.2 Hz), 6.95-7.01 (2H, m), 7.29-7.34 (2H, m), 7.36-7.40 (1H, m), 7.43-7.49 (1H, m), 8.43-8.49 (1H, m)

ESI-MS (m/e): 429.2 [M+H]$^+$

Example 50

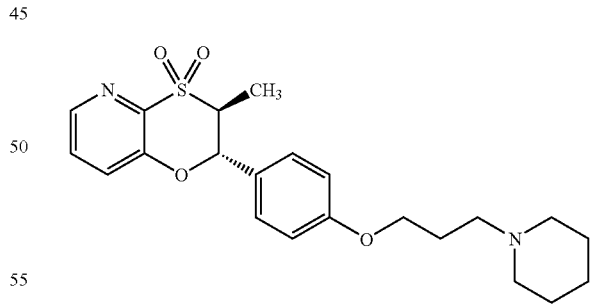

Optical resolution of 1-[3-[4-[(2,3-trans)-2,3-dihydro-4,4-dioxido-3-methyl-[1,4]oxathiino[3,2-b]pyridin-2-yl]phenoxy]propyl]-piperidine The compound synthesized in Example 44 was optically resolved in normal-phase chiral HPLC (CHIRALPAK OJ, 2 cmφ×25 cmL (by Daicel Chemical Industry), mobile phase: hexane/ethanol/diethylamine=55/45/0.1, flow rate: 10 ml/min, isogradient) to obtain 1-[3-[4-[(2S*,3S*)-2,3-dihydro-4,4-dioxido-3-methyl-[1,4]oxathiino[3,2-b]pyridin-2-yl]phenoxy]propyl]-piperidine (retention time: 22.2 min) and 1-[3-[4-[(2R*,3R*)-2,3-dihydro-4,4-dioxido-3-methyl-[1,4]oxathiino[3,2-b]pyridin-2-yl]phenoxy]propyl]-piperidine (retention time: 32.0 min).

Example 51

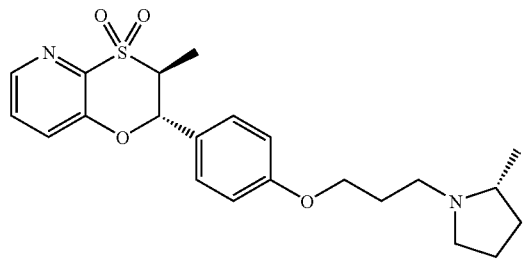

Synthesis of (2S*,3S*)-3-methyl-2-(4-{3-[(2R)-2-methylpyrrolidin-1-yl]propoxy}phenyl)-2,3-dihydro[1,4]oxathiino[3,2-b]pyridine 4,4-dioxide and (2R*,3R*)-3-methyl-2-(4-{3-[(2R)-2-methylpyrrolidin-1-yl]propoxy}phenyl)-2,3-dihydro[1,4]oxathiino[3,2-b]pyridine 4,4-dioxide (1) Synthesis of (2,3-trans)-3-methyl-2-(4-{3-[(2R)-2-methylpyrrolidin-1-yl]propoxy}phenyl)-2,3-dihydro[1,4]oxathiino[3,2-b]pyridine The intended compound was obtained according to the method of Example 3 but using 4-[(2,3-trans)-3-methyl-2,3-dihydro[1,4]oxathiino[3,2-b]pyridin-2-yl]phenol synthesized in Reference Example 5 and 3-[(2R)-2-methylpyrrolidin-1-yl]propan-1-ol synthesized in Reference Example 13 as the starting material.

$^1$H-NMR (400 MHz, CDCl$_3$, δ) δ: 1.06-1.14 (6H, m), 1.37-1.50 (1H, m), 1.60-2.27 (7H, m), 2.28-2.37 (1H, m), 2.95-3.04 (1H, m), 3.15-3.23 (1H, m), 3.57-3.65 (1H, m), 4.01-4.10 (2H, m), 4.67 (1H, d, J=8.8 Hz), 6.89-6.98 (3H, m), 7.08-7.13 (1H, m), 7.23-7.29 (2H, m), 8.07-8.13 (1H, m).
ESI-MS (m/e): 385.2 [M+H]$^+$ (2) Synthesis of (2,3-trans)-3-methyl-2-(4-{3-[(2R)-2-methylpyrrolidin-1-yl]propoxy}phenyl)-2,3-dihydro[1,4]oxathiino[3,2-b]pyridine 4,4-dioxide Aqueous 30% hydrogen peroxide solution (431 μL) and sodium tungstate dihydrate (9.1 mg) were added in that order to an acetic acid (1 mL) solution of the compound (51.2 mg, 0.014 mmol) obtained in the above (1), and stirred at room temperature for 12 hours. With cooling with ice, the reaction solution was poured little by little into aqueous 21% sodium hydrogensulfite solution (3 mL), and then stirred for 4 hours with cooling with ice. This was extracted twice with chloroform added thereto, and the organic layer was dried with magnesium sulfate, and the solvent was evaporated off under reduced pressure. The obtained residue was again dissolved in chloroform, and washed with aqueous saturated sodium hydrogencarbonate solution. The organic layer was dried with magnesium sulfate, and the solvent was concentrated under reduced pressure. The obtained residue was purified by silica gel column chromatography (chloroform/methanol=9/1) to obtain the intended compound (42 mg, 74%) as a white solid.

$^1$H-NMR (400 MHz, CDCl$_3$, δ) δ: 1.11 (3H, d, J=6.3 Hz), 1.22 (3H, d, J=6.8 Hz), 1.38-1.51 (1H, m), 1.64-2.40 (8H, m), 2.95-3.06 (1H, m), 3.16-3.25 (1H, m), 3.76-3.88 (1H, m), 4.03-4.13 (2H, m), 5.44 (1H, d, J=10.7 Hz), 6.94-7.03 (2H, m), 7.29-7.35 (2H, m), 7.36-7.42 (1H, m), 7.43-7.51 (1H, m), 8.44-8.48 (1H, m)
APCI-MS (m/e): 417.0 [M+H]$^+$ (3) Synthesis of the Entitled Compound The compound synthesized in the above (2) was optically resolved in normal-phase chiral HPLC (CHIRALPAK OJ, 2 cmφ×25 cmL (by Daicel Chemical Industry), mobile phase: hexane/ethanol/diethylamine=60/40/0.1, flow rate: 10 ml/min, isogradient) to obtain (2S*,3S*)-3-methyl-2-(4-{3-[(2R)-2-methylpyrrolidin-1-yl]propoxy}phenyl)-2,3-dihydro[1,4]oxathiino[3,2-b]pyridine 4,4-dioxide (retention time: 25.1 min) and (2R*,3R*)-3-methyl-2-(4-{3-[(2R)-2-methylpyrrolidin-1-yl]propoxy}phenyl)-2,3-dihydro[1,4]oxathiino[3,2-b]pyridine 4,4-dioxide (retention time: 30.1 min).

Example 52

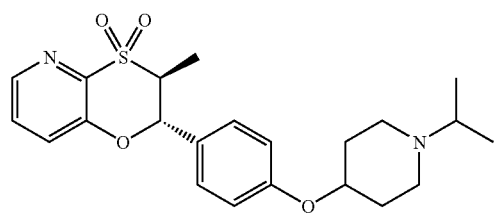

Synthesis of (2S*,3S*)-2-{4-[(1-isopropylpiperidin-4-yl)oxy]phenyl}-3-methyl-2,3-dihydro[1,4]oxathiino[3,2-b]pyridine 4,4-dioxide and (2R*,3R*)-2-{4-[(1-isopropylpiperidin-4-yl)oxy]phenyl}-3-methyl-2,3-dihydro[1,4]oxathiino[3,2-b]pyridine 4,4-dioxide (1) Synthesis of t-butyl 4-{4-[(2,3-trans)-3-methyl-2,3-dihydro[1,4]oxathiino[3,2-b]pyridin-2-yl]phenoxy}piperidine-1-carboxylate A crude product of the intended compound was obtained according to the method of Example 23(1) but using 4-[(2,3-trans)-3-methyl-2,3-dihydro[1,4]oxathiino[3,2-b]pyridin-2-yl]phenol synthesized in Reference Example 5 and N-(t-butoxycarbonyl)-4-piperidinol as the starting material.

(2) Synthesis of (2,3-trans)-3-methyl-2-[4-(piperidin-4-yloxy)phenyl]-2,3-dihydro[1,4]oxathiino[3,2-b]pyridine The crude product (6.4 g, corresponding to 14.5 mmol) of the compound obtained in the above (1) was dissolved in 4 N hydrochloric acid/ethyl acetate solution (21.8 cc) in the presence of anisole (3.1 cc), and stirred at room temperature for 24 hours. The solvent was evaporated off under reduced pressure, and the residue was washed with ethyl acetate to obtain a crude product (5.26 g) of the intended compound.

(3) Synthesis of (2,3-trans)-2-{4-[(1-isopropylpiperidin-4-yl)oxy]phenyl}-3-methyl-2,3-dihydro[1,4]oxathiino[3,2-b]pyridine A crude product of the intended compound was obtained according to the method of Example 23(3) but using the compound synthesized in the above (2) and acetone as the starting material.

(4) Synthesis of (2,3-trans)-2-{4-[(1-isopropylpiperidin-4-yl)oxy]phenyl}-3-methyl-2,3-dihydro[1,4]oxathiino[3,2-b]pyridine 4,4-dioxide The intended compound was obtained according to the method of Example 51(2) but using the compound synthesized in the above (3) as the starting material.
$^1$H-NMR (400 MHz, CDCl$_3$, δ) δ: 1.09 (6H, d, J=6.8 Hz), 1.23 (3H, d, J=6.8 Hz), 1.80-1.91 (2H, m), 2.02-2.14 (2H, m), 2.38-2.53 (2H, m), 2.73-2.87 (3H, m), 3.77-3.86 (1H, m), 4.32-4.41 (1H, m), 5.44 (1H, d, J=11.2 Hz), 6.95-7.01 (2H, m), 7.28-7.34 (2H, m), 7.36-7.41 (1H, m), 7.43-7.48 (1H, m).
ESI-MS (m/e): 417.1 [M+H]$^+$ (5) Synthesis of the Entitled Compound The compound synthesized in the above (4) was optically resolved in normal-phase chiral HPLC (CHIRALPAK OJ 2 cmφ×25 cmL (by Daicel Chemical Industry), mobile phase: hexane/ethanol/diethylamine=55/45/0.1, flow rate: 10 ml/min, isogradient) to obtain (2S*,3S*)-2-{4-[(1-isopropylpiperidin-4-yl)oxy]phenyl}-3-methyl-2,3-dihydro[1,4]oxathiino[3,2-b]pyridine 4,4-dioxide (retention time: 25.1 min) and (2R*,3R*)-2-{4-[(1-isopropylpiperidin-4-yl)oxy]phenyl}-3-methyl-2,3-dihydro[1,4]oxathiino[3,2-b]pyridine 4,4-dioxide (retention time: 30.7 min).

Example 53

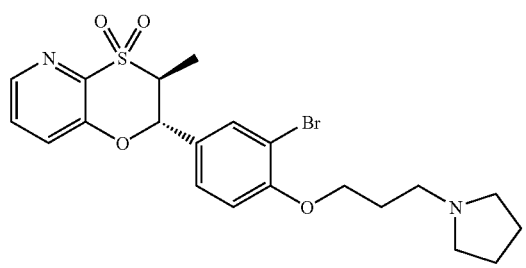

Synthesis of (2S*,3S)-2-[3-bromo-4-(3-pyrrolidin-1-ylpropoxy)phenyl]-3-methyl-2,3-dihydro[1,4]oxathiino[3,2-b]pyridine 4,4-dioxide (1) Synthesis of (2S*,3S*)-2-[3-bromo-4-(3-pyrrolidin-1-ylpropoxy)phenyl]-3-methyl-2,3-dihydro[1,4]oxathiino[3,2-b]pyridine The intended compound was obtained according to the method of Example 3 but using the compound synthesized in Reference Example 18-1 as the starting material.

$^1$H-NMR (400 MHz, CDCl$_3$, δ) δ: 1.12 (3H, d, J=6.8 Hz), 1.78-1.88 (4H, m), 2.06-2.16 (2H, m), 2.56-2.67 (4H, m), 2.71-2.79 (2H, m), 3.53-3.62 (1H, m), 4.11-4.17 (2H, m), 4.65 (1H, d, J=8.8 Hz), 6.91-6.98 (2H, m), 7.09-7.14 (1H, m), 7.20-7.25 (1H, m), 7.53-7.55 (1H, m), 8.08-8.13 (1H, m)
ESI-MS (m/e): 449.1 [M+H]$^+$ (2) Synthesis of the Entitled Compound The entitled compound was obtained according to the method of Example 51(2) but using the compound synthesized in the above (1) as the starting material.
$^1$H-NMR (400 MHz, CDCl$_3$, δ) δ: 1.24 (3H, d, J=7.3 Hz), 1.86-1.97 (4H, m), 2.17-2.28 (2H, m), 2.73-2.96 (6H, m), 3.73-3.83 (1H, m), 4.16-4.20 (2H, m), 5.42 (1H, d, J=11.2 Hz), 6.96-7.00 (1H, m), 7.26-7.31 (1H, m), 7.38-7.42 (1H, m), 7.45-7.51 (1H, m), 7.60-7.63 (1H, m), 8.46-8.49 (1H, m).
ESI-MS (m/e): 481.1 [M+H]$^+$ Example 54

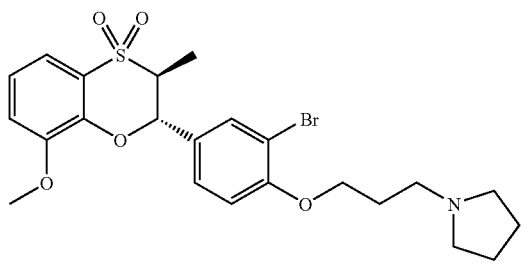

Synthesis of 1-(3-{2-bromo-4-[(2S*,3S*)-8-methoxy-3-methyl-4,4-dioxido-2,3-dihydro-1,4-benzoxathiin-2-yl]phenoxy}propyl)pyrrolidine (1) Synthesis of 1-(3-{2-bromo-4-[(2S*,3S*)-8-methoxy-3-methyl-2,3-dihydro-1,4-benzoxathiin-2-yl]phenoxy}propyl)pyrrolidine The intended compound was obtained according to the method of Example 3 but using the compound synthesized in Reference Example 17 and 1-(3-hydroxypropyl)pyrrolidine as the starting material.
$^1$H-NMR (400 MHz, CDCl$_3$, δ) δ: 1.14 (3H, d, J=6.7 Hz), 1.79-1.89 (4H, m), 2.03-2.11 (2H, m), 2.56-2.77 (6H, m), 3.40-3.49 (1H, m), 3.78 (3H, s), 4.05 (2H, t, J=6.3 Hz), 4.67 (1H, d, J=8.4 Hz), 6.53-6.58 (1H, m), 6.88-6.94 (2H, m), 7.08-7.12 (1H, m), 7.23-7.28 (2H, m)
ESI-MS (m/e): 478.1 [M+H]$^+$ (2) Synthesis of the Entitled Compound The entitled compound was obtained according to the method of Example 51(2) but using the compound synthesized in the above (1) as the starting material.
$^1$H-NMR (400 MHz, CDCl$_3$, δ) δ: 1.18 (3H, d, J=6.8 Hz), 1.78-1.86 (4H, m), 2.01-2.10 (2H, m), 2.52-2.72 (6H, m), 3.69-3.77 (1H, m), 3.79 (3H, s), 4.07 (2H, t, J=6.3 Hz), 5.32 (1H, d, J=10.7 Hz), 6.82-6.86 (1H, m), 6.94-7.00 (2H, m), 7.24-7.37 (3H, m).
ESI-MS (m/e): 510.1 [M+H]$^+$

Example 55

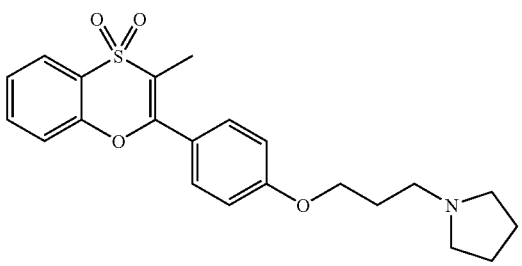

Synthesis of 1-{3-[4-(3-methyl-4,4-dioxido-1,4-benzoxathiin-2-yl)phenoxy]propyl}pyrrolidine (1) Synthesis of 4-(3-methyl-4,4-dioxido-1,4-benzoxathiin-2-yl)phenol M-chloroperbenzoic acid (content, 65% or more, 200 mg) was added to a chloroform (2 mL) solution of 4-(3-methyl-1,4-benzoxathiin-2-yl)phenol (100 mg, 0.39 mmol) synthesized in Reference Example 1-2, and stirred at room temperature for 90 minutes. Aqueous saturated sodium hydrogensulfite solution and aqueous saturated sodium hydrogencarbonate solution were added to the reaction solution, and stirred. The organic layer was collected, dried with magnesium sulfate, and concentrated under reduced pressure to obtain the entitled compound (106 mg, 94%).

$^1$H-NMR (CDCl$_3$) δ: 2.26 (3H, s), 5.36 (1H, s), 6.92-6.97 (2H, m), 7.25-7.30 (1H, m), 7.38-7.48 (3H, m), 7.58-7.63 (1H, m), 7.98-8.03 (1H, m)

ESI-MS (m/e): 289.1 [M+H]$^+$ (2) Synthesis of the Entitled Compound

The entitled compound was obtained according to the method of Example 3 but using the compound synthesized in the above (1) and 1-(3-hydroxypropyl)pyrrolidine as the starting material.

$^1$H-NMR (400 MHz, CDCl$_3$, δ) δ: 1.84-1.95 (4H, m), 2.09-2.19 (2H, m), 2.26 (3H, s), 2.64-2.84 (6H, m), 4.12 (2H, t, J=6.3 Hz), 6.97-7.03 (2H, m), 7.25-7.30 (1H, m), 7.37-7.43 (1H, m), 7.46-7.52 (2H, m), 7.57-7.62 (1H, m), 7.97-8.03 (1H, m)

ESI-MS (m/e): 400.1 [M+H]$^+$

Example 56

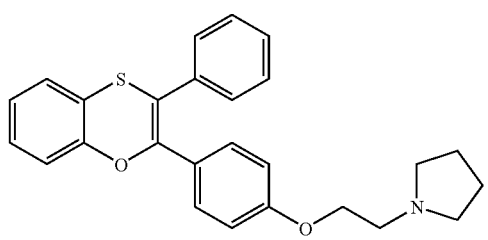

Synthesis of 1-{2-[4-(3-phenyl-1,4-benzoxathiin-2-yl)phenoxy]ethyl}pyrrolidine The entitled compound was obtained according to the method of Example 3 but using 4-(3-phenyl-1,4-benzoxathiin-2-yl)phenol synthesized in Reference Example 1-1 and 2-pyrrolidin-1-ylethanol as the starting material.

$^1$H-NMR (400 MHz, CDCl$_3$, δ) δ: 1.77-1.82 (4H, m), 2.60-2.2.63 (4H, m), 2.86-2.89 (2H, m), 4.05-4.08 (2H, m), 6.71-6.73 (2H, m), 7.00-7.26 (11H, m)

ESI-MS (m/e): 416.2 [M+H]$^+$

Example 57

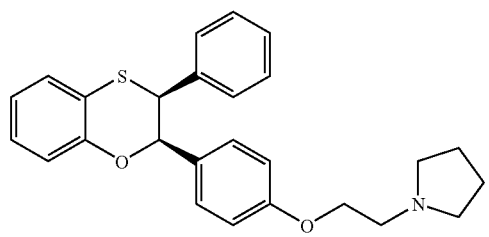

Synthesis of 1-(2-{4-[(2,3-cis)-3-phenyl-2,3-dihydro-1,4-benzoxathiin-2-yl]phenoxy}ethyl)pyrrolidine The entitled compound was obtained according to the method of Example 3 but using 4-[(2,3-cis)-3-phenyl-2,3-dihydro-1,4-benzoxathiin-2-yl]phenol synthesized in Reference Example 2-1 and 2-pyrrolidin-1-ylethanol as the starting material.

$^1$H-NMR (400 MHz, CDCl$_3$, δ) δ: 1.81-1.83 (4H, m), 2.62-2.66 (4H, m), 2.88-2.91 (2H, m), 4.05-4.08 (2H, m), 4.39 (1H, d, J=2.1 Hz), 5.53 (1H, d, J=2.1 Hz), 6.73-6.76 (2H, m), 6.87-7.20 (11H, m)

ESI-MS (m/e): 418.3 [M+H]$^+$

Example 58

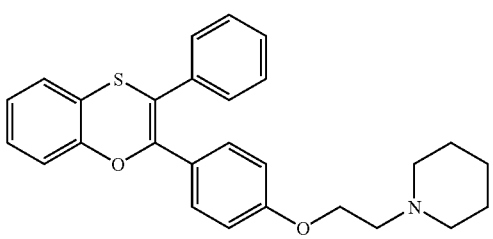

Synthesis of 1-{2-[4-(3-phenyl-1,4-benzoxathiin-2-yl)phenoxy]ethyl}piperidine The entitled compound was obtained according to the method of Example 3 but using 4-(3-phenyl-1,4-benzoxathiin-2-yl)phenol synthesized in Reference Example 1-1 and 2-piperidin-1-ylethanol as the starting material.

$^1$H-NMR (400 MHz, CDCl$_3$, δ) δ: 1.42-1.45 (2H, m), 1.56-1.62 (4H, m), 2.40-2.58 (4H, m), 2.73 (2H, t, J=6.1 Hz), 4.05 (2H, t, J=6.1 Hz), 6.69-6.7/(2H, m), 7.00-7.26 (11H, m).

ESI-MS (m/e): 430.2 [M+H]$^+$

Example 59

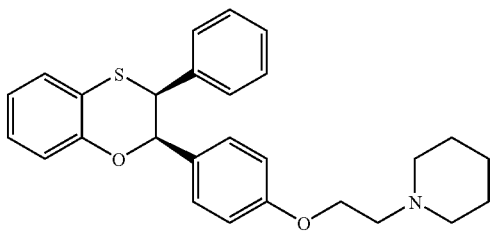

Synthesis of 1-(2-{4-[(2,3-cis)-3-phenyl-2,3-dihydro-1,4-benzoxathiin-2-yl]phenoxy}ethyl)piperidine The entitled compound was obtained according to the method of Example 3 but using 4-[(2,3-cis)-3-phenyl-2,3-dihydro-1,4-benzoxathiin-2-yl]phenol synthesized in Reference Example 2-1 and 2-piperidin-1-ylethanol as the starting material.

$^1$H-NMR (400 MHz, CDCl$_3$, δ) δ: 1.42-1.47 (2H, m), 1.57-1.66 (4H, m), 2.40-2.58 (4H, m), 2.72-2.75 (2H, m), 4.03-4.06 (2H, m), 4.39 (1H, d, J=2.2 Hz), 5.53 (1H, d, J=2.2 Hz), 6.71-6.75 (2H, m), 6.87-7.20 (11H, m)

ESI-MS (m/e): 432.2 [M+H]$^+$

Reference Example 1-1

Synthesis of 4-(3-phenyl-1,4-benzoxathiin-2-yl)phenol

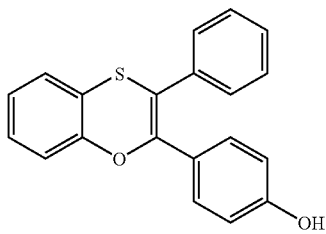

(1) Synthesis of 2-phenyl-1-{4-[(triisopropylsilyl)oxy]phenyl}ethanone

With cooling with ice, 60% oily sodium hydride (804 mg) was added to a THF (100 mL) solution of 1-(4-hydroxyphenyl)-2-phenylethanone (4.7 g, 22.1 mmol), and stirred for 10 minutes. With cooling with ice, chlorotriisopropylsilane (5.2 mL) was added to the reaction liquid, and stirred for 2 hours. Aqueous saturated ammonium chloride solution was added to the reaction liquid, then diluted with ethyl acetate and extracted. The organic layer was dried with magnesium sulfate, and concentrated under reduced pressure. The obtained residue was purified by silica gel column chromatography (hexane:ethyl acetate=20:1). The obtained crude product was recrystallized from ethanol to obtain the intended compound (3.8 g, 31%).

$^1$HNMR (400 MHz, CDCl$_3$, δ): 1.09-1.14 (18H, m), 1.24-1.32 (3H, m), 4.22 (2H, s), 6.89-6.91 (2H, m), 7.24-7.34 (5H, m), 7.92-7.94 (2H, m)

ESI-MS (m/e): 369.3 [M+H]$^+$ (2) Synthesis of 2-bromo-2-phenyl-1-{4-[(triisopropylsilyl)oxy]phenyl}ethanone With cooling with ice, a chloroform (8 mL) solution of bromine (512 μL) was added to a chloroform (75 mL) solution of the compound (3.66 g, 9.9 mmol) obtained in the above (1), and stirred for 3 hours with cooling with ice. The reaction liquid was concentrated under reduced pressure, then diluted with ethyl acetate, and extracted with aqueous saturated sodium hydrogencarbonate solution. The organic layer was dried with magnesium sulfate, and concentrated under reduced pressure to obtain a crude product (4.84 g) of the intended compound.

(3) Synthesis of 2-[(2-hydroxyphenyl)thio]-2-phenyl-1-{4-[(triisopropylsilyl)oxy]phenyl}ethanone With cooling with ice, N,N-diisopropylethylamine (2.0 mL) and 2-mercaptophenol (1.17 mL) were added in that order to a DMF (100 mL) solution of the compound (4.69 g) obtained in the above (2), and stirred for 2 hours with cooling with ice. The reaction liquid was diluted with ethyl acetate, and extracted with distilled water. The organic layer was dried with magnesium sulfate, and concentrated under reduced pressure. The obtained residue was purified by silica gel column chromatography (hexane:ethyl acetate=30:1) to obtain the intended compound (5.1 g, 99%) as a red oil.

$^1$HNMR (400 MHz, CDCl$_3$, δ): 1.43-1.18 (18H, m), 1.19-1.28 (3H, m), 4.23 (1H, s), 5.69 (1H, s), 6.65-6.69 (1H, m), 6.77-6.80 (2H, m), 6.89-6.93 (1H, m), 7.10-7.32 (6H, m), 7.79-7.95 (3H, m)

ESI-MS (m/e): 493.1 [M+H]$^+$ (4) Synthesis of triisopropyl[4-(3-phenyl-1,4-benzoxathiin-2-yl)phenoxy]silane P-toluenesulfonic acid monohydrate (179 mg, 1.04 mmol) was added to a toluene (130 mL) solution of the compound (2.6 g, 5.2 mmol) obtained in the above (3), and stirred at 130° C. for 3 hours. The reaction liquid was restored to room temperature, diluted with ethyl acetate, and extracted with aqueous saturated sodium hydrogencarbonate solution. The organic layer was dried with magnesium sulfate, and concentrated under reduced pressure. The obtained residue was purified by silica gel column chromatography (hexane:ethyl acetate=50:1) to obtain the intended compound (1.8 g, 73%).

(5) Synthesis of the Entitled Compound

With cooling with ice, acetic acid (386 μL) and tetrabutylammonium fluoride (1 M THF solution, 5.1 mL) were added in that order to a THF (40 mL) solution of the compound (1.6 g, 3.37 mmol) obtained in the above (4), and stirred for 2 hours with cooling with ice. The reaction liquid was diluted with ethyl acetate, and extracted with aqueous saturated sodium hydrogencarbonate solution. The organic layer was dried with magnesium sulfate, and concentrated under reduced pressure. The obtained residue was purified by silica gel column chromatography (hexane:ethyl acetate=6:1) to obtain the entitled compound (949 mg, 88%).

$^1$HNMR (400 MHz, CDCl$_3$, δ): 6.61-6.65 (2H, m), 7.00-7.06 (2H, m), 7.11-7.18 (4H, m), 7.22-7.26 (5H, m)

ESI-MS (m/e): 319.1 [M+H]$^+$

Reference Example 1-2

Synthesis of 4-(3-methyl-1,4-benzoxathiin-2-yl)phenol

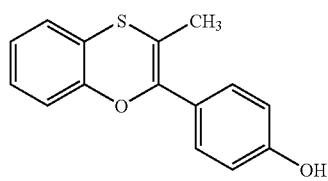

(1) Synthesis of 1-{4-[(triisopropylsilyl)oxy]phenyl}propan-1-one

The intended compound was obtained according to the method of Reference Example 1-1-(1), according to a method similar to it, and according to a combination of the method with an ordinary method, but using 4'-hydroxypropiophenone as the starting material.

$^1$H-NMR (400 MHz, CDCl$_3$, δ) δ: 1.21 (3H, t, J=7.1 Hz), 1.24-1.33 (3H, m), 2.95 (2H, q, J=7.3 Hz), 6.88-6.93 (2H, m), 7.85-7.92 (2H, m)

ESI-MS (m/e): 307.3 [M+H]$^+$

(2) Synthesis of 2-bromo-1-{4-[(triisopropylsilyl)oxy]phenyl}propan-1-one

A crude product of the intended compound was obtained according to the method of Reference Example 1-1-(2), according to a method similar to it, and according to a combination of the method with an ordinary method, but using the compound synthesized in the above (1) as the starting material.

(3) Synthesis of 2-[(2-hydroxyphenyl)thio]-1-{4-[(triisopropylsilyl)oxy]phenyl}propan-1-one The intended compound was obtained according to the method of Reference Example 1-1-(3) but using the compound synthesized in the above (2) as the starting material.

$^1$HNMR (400 MHz, CDCl$_3$, ppm): 1.09-1.19 (18H, m), 1.21-1.32 (3H, m), 1.48 (3H, d, J=6.8 Hz), 4.56-4.60 (1H, m), 6.79-6.96 (4H, m), 7.21-7.38 (2H, m), 7.81-7.84 (2H, m)

ESI-MS (m/e): 431.2 [M+H]$^+$

(4) Synthesis of the Entitled Compound

The entitled compound was obtained according to the method of Reference Example 1-1-(4), (5), according to a method similar to it, and according to a combination of the method with an ordinary method, but using the compound synthesized in the above (3) as the starting material.

$^1$HNMR (400 MHz, CDCl$_3$, δ): 1.98 (3H, s), 6.83-6.85 (2H, m), 6.92-7.13 (4H, m), 7.33-7.35 (2H, m)

ESI-MS (m/e): 257.1 [M+H]$^+$

Reference Example 1-3

Synthesis of 4-(3-ethyl-1,4-benzoxathiin-2-yl)phenol

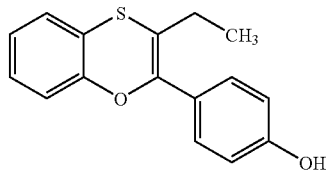

(1) Synthesis of 2-[(2-hydroxyphenyl)thio]-1-{4-[(triisopropylsilyl)oxy]phenyl}butan-1-one The intended compound was obtained according to the method of Reference Example 1-1-(1), (2), (3), according to a method similar to it, and according to a combination of the method with an ordinary method, but using 4'-hydroxybutyrophenone as the starting material. $^1$HNMR (400 MHz, CDCl$_3$, ppm): 1.02-1.19 (18H, m), 1.21-1.32 (3H, m), 1.80-2.05 (2H, m), 4.36 (1H, t, J=6.9 Hz), 6.77-7.02 (4H, m), 7.22-7.37 (2H, m), 7.77-7.79 (2H, m)

ESI-MS (m/e): 445.2 [M+H]$^+$

(2) Synthesis of the Entitled Compound

The entitled compound was obtained according to the method of Reference Example 1-1-(4), (5), according to a method similar to it, and according to a combination of the method with an ordinary method, but using the compound obtained in (1) as the starting material.

$^1$HNMR (400 MHz, CDCl$_3$, ppm): 1.14 (3H, t, J=7.4 Hz), 2.31-2.33 (2H, m), 6.83-6.85 (2H, m), 6.92-6.94 (2H, m), 7.01-7.03 (2H, m), 7.09-7.11 (2H, m), 7.30-7.32 (2H, m)

ESI-MS (m/e): 271.1 [M+H]$^+$

Reference Example 2-1

Synthesis of 4-[(2,3-cis)-3-phenyl-2,3-dihydro-1,4-benzoxathiin-2-yl]phenol

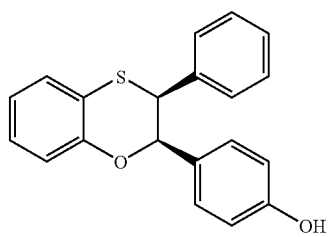

(1) Synthesis of triisopropyl[4-[(2,3-cis)-3-phenyl-2,3-dihydro-1,4-benzoxathiin-2-yl]phenoxy}silane In a nitrogen atmosphere with cooling with ice, trifluoroacetic acid and triethylsilane were dropwise added in that order to a dichloromethane solution of the compound (2.8 g, 5.6 mmol) obtained in Reference Example 1-1-(1), and stirred for 2 hours with cooling with ice, then restored to room temperature and further stirred for 9 hours. The reaction liquid was extracted with aqueous saturated sodium hydrogencarbonate solution. The organic layer was dried with magnesium sulfate, and concentrated under reduced pressure. The obtained residue was purified by silica gel column chromatography (hexane:ethyl acetate=50:1) to obtain a crude product (2.2 g) of the intended compound as an orange oil.

(2) Synthesis of the Entitled Compound

The entitled compound was obtained according to the method of Reference Example 1-1-(5) but using the compound obtained in the above (1) as the starting material.

$^1$HNMR (400 MHz, CDCl$_3$, δ): 4.39 (1H, d, J=2.3 Hz), 5.53 (1H, d, J=2.3 Hz), 6.65-6.68 (2H, m), 6.86-7.00 (6H, m), 7.06-7.20 (5H, m)

ESI-MS (m/e): 321.1 [M+H]$^+$

Reference Example 2-2

Synthesis of 4-[(2,2-cis)-3-methyl-2,3-dihydro-1,4-benzoxathiin-2-yl]phenol

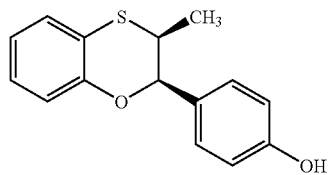

The entitled compound was obtained according to the method of Reference Example 2-1, according to a method similar to it, and according to a combination of the method with an ordinary method, but using 2-[(2-hydroxyphenyl)thio]-1-{4-[(triisopropylsilyl)oxy]phenyl}propan-1-one obtained in Reference Example 1-2 as the starting material.

$^1$HNMR (400 MHz, CDCl$_3$, δ): 1.23 (3H, d, J=7.0 Hz), 3.32-3.38 (1H, m), 4.92 (1H, brs), 5.42 (1H, d, J=1.6 Hz), 6.86-7.11 (6H, m), 7.29-7.33 (2H, m)

ESI-MS (m/e): 259.1 [M+H]$^+$

Reference Example 2-3

Synthesis of 4-[(2,3-cis)-3-ethyl-2,3-dihydro-1,4-benzoxathiin-2-yl]phenol

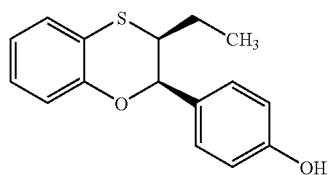

The entitled compound was obtained according to the method of Reference Example 2-1, according to a method similar to it, and according to a combination of the method with an ordinary method, but using 2-[(2-hydroxyphenyl)thio]-1-{4-[(triisopropylsilyl)oxy]phenyl}butan-1-one obtained in Reference Example 1-3 as the starting material.

$^1$HNMR (400 MHz, CDCl$_3$, δ): 0.97 (3H, t, J=7.2 Hz), 1.40-1.61 (2H, m), 3.08-3.12 (1H, m), 4.81 (1H, brs), 5.49 (1H, d, J=1.8 Hz), 6.85-6.93 (4H, m), 7.01-7.12 (2H, m), 7.31-7.33 (2H, m)

ESI-MS (m/e): 273.1 [M+H]$^+$

Reference Example 2-4

Synthesis of 4-(2,3-dihydro-1,4-benzoxathiin-2-yl)phenol

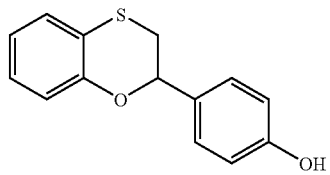

(1) Synthesis of 1-{4-[(triisopropylsilyl)oxy]phenyl}ethanone

The intended compound was obtained according to the method of Reference Example 1-1-(1) but using 4'-hydroxyacetophenone as the starting material.

$^1$HNMR (400 MHz, CDCl$_3$, δ): 1.05-1.12 (18H, m), 1.25-1.30 (3H, m), 2.55 (3H, s), 6.90-6.92 (2H, m), 7.87-7.89 (2H, m)

(2) Synthesis of 2-bromo-1-{-4-[(triisopropylsilyl)oxy]phenyl}ethanone

Copper(II) bromide (5.95 g) was added to an ethyl acetate (15 mL)/chloroform (15 mL) mixed solution of the compound (3.5 g, 15.67 mmol) obtained in the above (1), and stirred at 90° C. for 2.5 hours. The insoluble matter was filtered away, then aqueous saturated sodium hydrogencarbonate solution was added to the mother liquid and stirred for a while, and then concentrated under reduced pressure. The obtained residue was diluted with ethyl acetate, and washed with aqueous saturated sodium hydrogencarbonate solution and aqueous saturated sodium chloride solution in that order. The organic layer was dried with sodium sulfate, and concentrated under reduced pressure to obtain a crude product of the intended compound (4.16 g).

(3) Synthesis of 2-[(2-hydroxyphenyl)thio]-1-{4-[(triisopropylsilyl)oxy]phenyl}ethanone The intended compound was obtained according to the method of Reference Example 1-1-(3) but using the compound obtained in the above (2) as the starting material.

$^1$HNMR (400 MHz, CDCl$_3$, δ): 1.05-1.11 (18H, m), 1.24-1.31 (3H, m), 4.18 (2H, s), 6.80-6.90 (3H, m), 6.96-6.98 (1H, m), 7.24-7.28 (1H, m), 7.49-7.51 (1H, m), 7.83-7.85 (1H, m), 8.15 (1H, brs)

ESI-MS (m/e): 417.2 [M+H]$^+$ (4) Synthesis of the Entitled Compound

The entitled compound was obtained according to the method of Reference Example 2-1, according to a method similar to it, and according to a combination of the method with an ordinary method, but using the compound obtained in the above (3) as the starting material.

¹HNMR (400 MHz, CDCl₃, δ): 3.04 (1H, dd, J=2.0 Hz, 13.2 Hz), 3.27 (1H, dd, J=9.6 Hz, 13.2 Hz), 4.99 (1H, brs), 5.12 (1H, dd, J=2.0 Hz, 9.6 Hz), 6.85-6.92 (4H, m), 6.99-7.04 (1H, m), 7.10-7.12 (1H, m), 7.27-7.31 (2H, m)

ESI-MS (m/e): 245.1 [M+H]⁺

Reference Example 3-1

Synthesis of 4-[(2,3-trans)-3-methyl-2,3-dihydro-1,4-benzoxathiin-2-yl]phenol

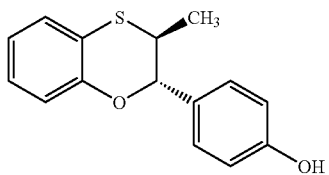

(1) Synthesis of 2-[(2-hydroxy-1-methyl-2-{4-[(triisopropylsilyl)oxy]phenyl}ethyl)thio]phenol With cooling with ice, sodium borohydride (5.5 g, 134 mmol) was added to a dichloromethane (500 mL)/methanol (500 mL) mixed solution of 2-[(2-hydroxyphenyl)thio]-1-{4-[(triisopropylsilyl)oxy]phenyl}propan-1-one (48 g, 112 mmol) obtained in Reference Example 1-2, and stirred for 2 hours with cooling with ice, then restored to room temperature, and further stirred for 40 minutes. Aqueous saturated ammonium chloride solution was added, and stirred for a while, and then the solvent was almost completely evaporated off under reduced pressure. The residue was diluted with ethyl acetate, and extracted with aqueous saturated ammonium chloride solution. The organic layer was dried with sodium sulfate, and concentrated under reduced pressure to obtain a crude product (51.4 g) of the intended compound.

(2) Synthesis of triisopropyl {4-[(2,3-trans)-3-methyl-2,3-dihydro-1,4-benzoxathiin-2-yl]phenoxy}silane Amberlyst 15 (15.4 g) was added to a toluene (750 mL) solution of the compound (51.4 g) obtained in the above (1), and stirred at room temperature for 10 hours. The reaction liquid was filtered, and the mother liquid was concentrated under reduced pressure to obtain a crude product (47.0 g) of the intended compound as a yellow oil.

(3) Synthesis of the Entitled Compound

With cooling with ice, acetic acid (6.5 mL) and tetrabutylammonium fluoride (1 M THF solution, 136 mL) were added in that order to a THF (900 mL) solution of the compound (47.0 g) obtained in the above (2), and stirred for 5 hours with cooling with ice. The reaction liquid was concentrated under reduced pressure, and the obtained residue was diluted with ethyl acetate, and extracted with aqueous saturated sodium hydrogencarbonate solution. The organic layer was dried with sodium sulfate, and concentrated under reduced pressure. The obtained residue was purified by silica gel column chromatography (chloroform:ethyl acetate=20:1) to obtain a crude product (24.6 g) of the entitled compound. Further, this was dissolved in diethyl ether (120 mL), and hexane (140 mL) was added thereto, and the precipitated powder was collected by filtration to obtain a crude product (13.7 g) of the entitled compound. Further, this was recrystallized from ethyl acetate (80 mL) and hexane (500 mL) to obtain the entitled compound (7.7 g, 27% in 3 steps) as a colorless crystal.

¹HNMR (400 MHz, CDCl₃, δ): 1.07 (3H, d, J=6.8 Hz), 3.42-3.46 (1H, m), 4.67 (1H, d, J=8.6 Hz), 4.90 (1H, brs), 6.86-6.90 (4H, m), 6.97-7.02 (1H, m), 7.08-7.10 (1H, m), 7.22-7.24 (2H, m)

ESI-MS (m/e): 259.1 [M+H]⁺

Reference Example 3-2

Synthesis of 4-[(2,3-trans)-3-ethyl-2,3-dihydro-1,4-benzoxathiin-2-yl]phenol

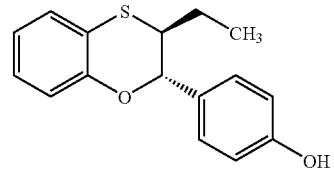

The entitled compound was obtained according to the method of Reference Example 3-1, according to a method similar to it, and according to a combination of the method with an ordinary method, but using 2-[(2-hydroxyphenyl)thio]-1-{4-[(triisopropylsilyl)oxy]phenyl}butan-1-one obtained in Reference Example 1-3 as the starting material.

¹HNMR (400 MHz, CDCl₃, δ): 0.95 (3H; t, J=7.4 Hz), 1.36-1.51 (2H, m), 3.32-3.37 (1H, m), 4.78 (1H, d, J=8.2 Hz), 4.88 (1H, brs), 6.85-6.90 (4H, m), 6.97-7.01 (1H, m), 7.10-7.12 (1H, m), 7.21-7.23 (2H, m)

ESI-MS (m/e): 273.1 [M+H]⁺

Example 4-1

Synthesis of 4-[(2,3-cis)-2-methyl-2,3-dihydro-1,4-benzoxathiin-3-yl]phenol

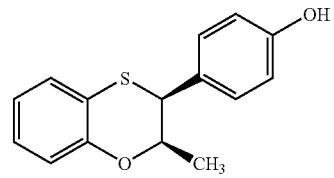

(1) Synthesis of 1-{4-[(triisopropylsilyl)oxy]phenyl}acetone

The intended compound was obtained according to the method of Reference Example 1-1(1) but using 4-hydroxyphenylacetone as the starting material.

¹HNMR (400 MHz, CDCl₃, δ): 1.06-1.11 (18H, m), 1.23-1.25 (3H, m), 2.11 (3H, s), 3.60 (2H, s), 6.83-6.85 (2H, m), 7.04-7.06 (2H, m)

ESI-MS (m/e): 307.3 [M+H]⁺

(2) Synthesis of 1-bromo-1-{4-[(triisopropylsilyl)oxy]phenyl}acetone

A crude product of the intended compound was obtained according to the method of Reference Example 1-1(2) but using the compound synthesized in the above (1) as the starting material.

(3) Synthesis of 1-[(2-hydroxyphenyl)thio]-1-{4-[(triisopropylsilyl)oxy]phenyl}acetone A crude product of the intended compound was obtained according to the method of Reference Example 1-1(3) but using the compound synthesized in the above (2) as the starting material.

(4) Synthesis of the Entitled Compound

The entitled compound was obtained according to the method of Reference Example 2-1-(1) and (2), according to a method similar to it, and according to a combination of the method with an ordinary method, but using the compound synthesized in the above (3) as the starting material.

$^1$HNMR (400 MHz, CDCl$_3$, δ): 1.22 (3H, d, J=6.4 Hz), 4.26 (1H, d, J=2.5 Hz), 4.54-4.59 (1H, m), 4.98 (1H, brs), 6.74-6.92 (4H, m), 7.00-7.22 (4H, m)

ESI-MS (m/e): 259.1 [M+H]$^+$

Reference Example 5

Synthesis of 4-[(2,3-trans)-3-methyl-2,3-dihydro[1,4]oxathiino[3,2-b]pyridin-2-yl]phenol

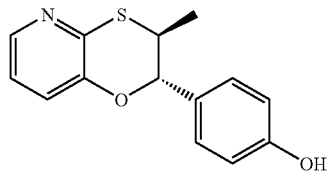

(1) Synthesis of 2-[(4-methoxybenzyl)thio]pyridin-3-ol

4-Methoxy-α-toluenethiol (9.4 mL), potassium fluoride (3.34 g) and potassium carbonate (10.3 g) were added to a DMF (100 mL) solution of 2-bromo-3-hydroxypyridine (10 g, 57.5 mmol), and stirred at 150° C. for 3 days. The reaction liquid was diluted with ethyl acetate, and washed three times with distilled water. The organic layer was dried with magnesium sulfate, and concentrated under reduced pressure. The obtained residue was crystallized from ethyl acetate and hexane to obtain the intended compound (6.2 g, 43%) as a white solid.

$^1$HNMR (400 MHz, CDCl$_3$, δ): 3.77 (3H, s), 4.27 (2H, s), 6.30 (1H, brs), 6.75-6.80 (2H, m), 7.05-7.18 (4H, m), 8.16-8.19 (1H, m).

ESI-MS (m/e): 248.1 [M+H]$^+$

(2) Synthesis of 2-mercaptopyridin-3-ol

Trifluoroacetic acid (120 mL) and anisole (14.7 mL) were added to the compound (6.7 g, 27.1 mmol) synthesized in the above (1), and stirred at 70° C. for 10 hours. The reaction liquid was concentrated under reduced pressure, and the obtained residue was washed with hexane to obtain the intended compound (2.76 g, 88%) as an orange solid.

$^1$HNMR (400 MHz, CD$_3$OD, δ): 6.78-6.82 (1H, m), 7.06-7.08 (1H, m), 7.32-7.34 (1H, m).

ESI-MS (m/e): 128.0 [M+H]$^+$

(3) Synthesis of 1-(4-hydroxyphenyl)-2-[(3-hydroxypyridin-2-yl)thio]propan-1-one N,N-diisopropylethylamine (4.8 mL) was added to a DMF (170 mL) solution of the compound (9.6 g, 24.9 mmol) synthesized in Reference Example 1-2-(2), and a DMF (30 mL) solution of 2-mercaptopyridin-3-ol (3.3 g) synthesized in the above (2) was dropwise added with cooling with ice, and further stirred for 1.5 hours with cooling with ice. The reaction liquid was diluted with ethyl acetate, and washed three times with distilled water. The organic layer was dried with sodium sulfate, and concentrated under reduced pressure. The obtained residue was purified by silica gel column chromatography (hexane:ethyl acetate=20:1 to 4:1), and the solvent was evaporated off under reduced pressure. With cooling with ice, acetic acid (1.9 mL) and tetrabutylammonium fluoride (1 M THF solution, 27 mL) were added in that order to a THF (120 mL) solution of the obtained residue (8.1 g), and stirred for 2 hours with cooling with ice. The reaction liquid was diluted with ethyl acetate, and extracted with aqueous saturated sodium hydrogencarbonate solution. The organic layer was dried with magnesium sulfate, and concentrated under reduced pressure to obtain a crude product (6.5 g) of the intended compound.

(4) Synthesis of 2-{[2-hydroxy-2-(4-hydroxyphenyl)-1-methylethyl]thio}pyridin-3-ol A crude product (5.7 g) of the intended compound was obtained according to the method of Reference Example 3-1-(1) but using the compound (6.5 g) synthesized in the above (3) as the starting material.

(5) Synthesis of the Entitled Compound

The compound (5.7 g) synthesized in the above (4) was dissolved in trifluoroacetic acid (50 mL), and stirred at room temperature for 2 hours. The reaction liquid was concentrated under reduced pressure, then the residue was dissolved in chloroform, and extracted with aqueous saturated sodium hydrogencarbonate solution. The aqueous layer was washed twice with chloroform, then the organic layer was collected, dried with magnesium sulfate, and concentrated under reduced pressure. The obtained residue was washed with ethyl acetate to obtain the entitled compound (2.1 g, 32% in 4 steps) as a white solid.

$^1$HNMR (400 MHz, DMSO-d$_6$, δ): 1.04 (3H, d, J=6.8 Hz), 3.77-3.80 (1H, m), 4.79 (1H, d, J=8.4 Hz), 6.80-6.82 (2H, m), 7.05-7.08 (1H, m), 7.23-7.27 (3H, m), 8.05-8.07 (1H, m), 9.60 (1H, s)

ESI-MS (m/e): 260.2 [M+H]$^+$

Reference Example 6

Synthesis of 1-cyclobutylpiperidin-4-ol

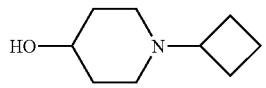

A methanol solution (48 mL) of 0.3 N sodium cyanoborohydride/0.15 N zinc(II) chloride was added to a methanol (50 mL) solution of 4-hydroxypiperidine (1.1 g, 1.0 mmol) and cyclobutanone (1 g), and stirred at room temperature for 24 hours. The solvent was concentrated under reduced pressure, distilled water was added, and extracted eight times with chloroform. The organic layer was dried with magnesium sulfate, and concentrated under reduced pressure to obtain the entitled compound (1.68 g, 98%) as a yellow oil.

$^1$HNMR (400 MHz, CDCl$_3$, δ): 1.52-1.75 (4H, m), 1.81-2.08 (8H, m), 2.61-2.75 (3H, m), 3.62-3.76 (1H, m).

ESI-MS (m/e): 156.2 [M+H]$^+$

Reference Example 7

Synthesis of 3-[(3S)-3-methylpiperidin-1-yl]propan-1-ol

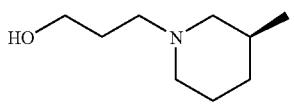

(3S)-3-methylpiperidin(S)-(+)-mandelate (19.9 g, 79.1 mmol), 3-bromo-1-propanol (10 g, 71.9 mmol) and potassium carbonate (14.9 g, 108 mmol) were mixed in THF (200 mL), and heated under reflux for 30 hours. The insoluble matter was separated by filtration, the filtrate was concentrated, and ethyl acetate and hexane were added to the residue. The resulting insoluble matter was separated by filtration, the filtrate was concentrated and evaporated under reduced pressure to obtain the intended product (9.6 g, 85%) as a colorless oil. (3S)-3-methylpiperidin (S)-(+)-mandelate was synthesized according to the method described in a reference (J. Org. Chem., 1987, Vol. 52, p. 5466).

Reference Example 8

Synthesis of 4-[(2,3-trans)-8-methoxy-3-methyl-2,3-dihydro-1,4-benzoxathiin-2-yl]phenol

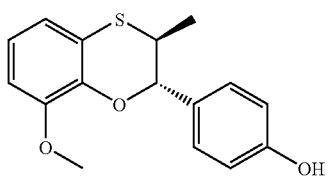

(1) Synthesis of 1-methoxy-2-(methoxymethoxy)benzene

Potassium tert-butoxide (67.9 g, 605 mmol) was dissolved in a mixed solvent of DMF (500 mL) and THF (500 mL), then with cooling with ice, 2-methoxyphenol (68.28 g, 550 mmol) was dropwise added. This was stirred at room temperature for 2 hours, and then chloromethyl methyl ether (46 mL, 605 mmol) was added. After stirred for 5 hours at room temperature, aqueous saturated ammonium chloride solution was added to the reaction solution, and extracted with ethyl acetate. The organic layer was washed with saturated saline, then dried with sodium sulfate, and concentrated. Purified by silica gel column chromatography, the intended compound (97.66 g, 100%) was obtained as a pale yellow oil.

(2) Synthesis of 3-methoxy-2-(methoxymethoxy)phenyl dimethyldithiocarbamate

At −78° C., 2.66 M n-BuLi/hexane solution (129 mL, 342 mmol) was dropwise added to an ether (500 mL) solution of the compound (48 g, 285 mmol) synthesized in the above (1), and stirred at 0° C. for 2 hours. At −78° C., a THF suspension of tetramethylthiuram disulfide (82.23 g, 342 mmol) was dropwise added, and stirred at room temperature for 14 hours. Aqueous saturated ammonium chloride solution was added to the reaction liquid, and extracted with ethyl acetate. The organic layer was washed with saturated saline, then dried with sodium sulfate, and concentrated. Purified by silica gel column chromatography, the intended compound (70.49 g, 86%) was obtained as a white solid.

(3) Synthesis of 2-hydroxy-3-methoxyphenyl dimethyldithiocarbamate

4 N hydrogen chloride/dioxane solution (50 mL) was added to a methanol (200 mL) solution of the compound (70.49 g) synthesized in the above (2), and stirred at room temperature for 2 hours. The reaction liquid was concentrated and extracted with chloroform. The organic layer was washed with saturated saline, then dried with sodium sulfate, and concentrated to obtain the intended compound (46.65 g, 78%) as a brown solid.

(4) Synthesis of 2-mercapto-6-methoxyphenol

With cooling with ice, lithium aluminium hydride (11.9 g, 288 mmol) was added to a THF (300 mL) solution of the compound (46.65 g, 192 mmol) synthesized in the above (3). After stirred at room temperature for 3 hours, 4 N NaOH was added, and filtered. The filtrate was concentrated and distilled under reduced pressure to obtain the intended compound (24.11 g, 80%) as a pale yellow oil.

$^1$HNMR (400 MHz, CDCl$_3$, δ): 3.70 (1H, s), 3.88 (3H, s), 5.99 (1H, s), 6.67-6.71 (1H, m), 6.73-6.79 (1H, m), 6.84-6.88 (1H, m)

(5) Synthesis of the Entitled Compound

The entitled compound was obtained according to the method of Reference Example 1-1-(3) and Reference Example 3-1, according to a method similar to it, and according to a combination of the method with an ordinary method, but using the compound synthesized in the above (4) and 2-bromo-1-{4-[(triisopropylsilyl)oxy]phenyl}propan-1-one synthesized in Reference Example 1-2-(2) as the starting material.

$^1$HNMR (400 MHz, CDCl$_3$, δ): 1.08 (3H, d, J=6.8 Hz), 3.46-3.54 (1H, m), 3.83 (3H, s), 4.67 (1H, d, J=8.3 Hz), 5.81 (1H, brs), 6.62-6.68 (3H, m), 6.70-6.74 (1H, m), 6.81-6.87 (1H, m), 7.06-7.12 (2H, m)

ESI-MS (m/e): 289.1 [M+H]$^+$

Reference Example 9

Synthesis of 4-[(2,3-trans)-5-methoxy-3-methyl-2,3-dihydro-1,4-benzoxathiin-2-yl]phenol

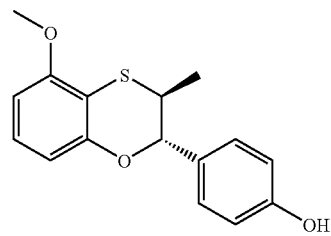

(1) Synthesis of 1-methoxy-3-(methoxymethoxy)benzene

The intended compound was obtained according to the method of Reference Example 8-(1) but using 3-methoxyphenol as the starting material.

(2) Synthesis of 2-methoxy-6-(methoxymethoxy)phenyl dimethyldithiocarbamate

The intended compound was obtained according to the method of Reference Example 8-(2) but using the compound obtained in the above (1) as the starting material.

(3) Synthesis of 2-hydroxy-6-methoxyphenyl dimethyldithiocarbamate

The intended compound was obtained according to the method of Reference Example 8-(3) but using the compound obtained in the above (2) as the starting material.

(4) Synthesis of 2-mercapto-3-methoxyphenol

The intended compound was obtained according to the method of Reference Example 8-(4) but using the compound obtained in the above (3) as the starting material.

$^1$HNMR (400 MHz, CDCl$_3$, δ): 3.03 (1H, s), 3.89 (3H, s), 6.09 (1H, brs), 6.47-6.51 (1H, m), 6.59-6.64 (1H, m), 7.10-7.16 (1H, m)

(5) Synthesis of the Entitled Compound

The entitled compound was obtained according to the method of Reference Example 1-1-(3) and Reference Example 3-1, according to a method similar to it, and according to a combination of the method with an ordinary method, but using the compound obtained in the above (4) and 2-bromo-1-{4-[(triisopropylsilyl)oxy]phenyl}propan-1-one synthesized in Reference Example 1-2-(2) as the starting material.

$^1$HNMR (400 MHz, CDCl$_3$, δ): 1.09 (3H, d, J=6.8 Hz), 3.32-3.41 (1H, m), 3.89 (3H, s), 4.62 (1H, d, J=8.8 Hz), 6.46-6.51 (1H, m), 6.56-6.60 (1H, m), 6.83-6.89 (2H, m), 6.94-7.03 (1H, m), 7.20-7.25 (2H, m)

ESI-MS (m/e): 289.1 [M+H]$^+$

Reference Example 10

Synthesis of 4-[(2,3-trans)-6-methoxy-3-methyl-2,3-dihydro-1,4-benzoxathiin-2-yl]phenol

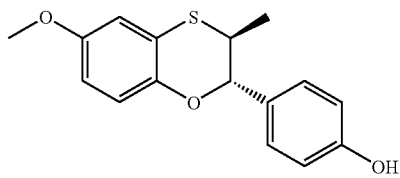

The entitled compound was obtained according to the method of Reference Example 1-1-(3) and Reference Example 3-1, according to a method similar to it, and according to a combination of the method with an ordinary method, but using 2-bromo-1-{4-[(triisopropylsilyl)oxy]phenyl}propan-1-one synthesized in Reference Example 1-2-(2) and 2-mercapto-4-methoxyphenol synthesized in Reference Example 19 as the starting material.

$^1$HNMR (400 MHz, CDCl$_3$, δ): 1.06 (3H, d, J=6.8 Hz), 3.41-3.49 (1H, m), 3.75 (3H, s), 4.59 (1H, d, J=8.8 Hz), 4.90 (1H, brs), 6.55-6.59 (1H, m), 6.61-6.64 (1H, m), 6.80-6.83 (1H, m), 6.84-6.90 (2H, m), 7.20-7.25 (2H, m)

ESI-MS (m/e): 289.1 [M+H]$^+$

Reference Example 11

Synthesis of 4-[(2,3-trans)-7-methoxy-3-methyl-2,3-dihydro-1,4-benzoxathiin-2-yl]phenol

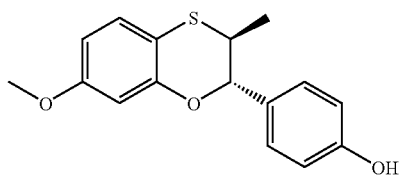

The entitled compound was obtained according to the method of Reference Example 1-1-(3) and Reference Example 3-1, according to a method similar to it, and according to a combination of the method with an ordinary method, but using 2-bromo-1-{4-[(triisopropylsilyl)oxy]phenyl}propan-1-one synthesized in Reference Example 1-2-(2) and 2-mercapto-5-methoxyphenol synthesized in Reference Example 20 as the starting material.

$^1$HNMR (400 MHz, CDCl$_3$, δ): 1.07 (3H, d, J=6.8 Hz), 3.35-3.43 (1H, m), 3.73 (3H, s), 4.70 (1H, d, J=8.3 Hz), 6.48-6.56 (2H, m), 6.84-6.89 (2H, m), 6.95-7.00 (1H, m), 7.20-7.24 (2H, m)

ESI-MS (m/e): 289.0 [M+H]$^+$

Reference Example 12

Synthesis of 5-[(2,3-trans)-3-methyl-2,3-dihydro-1,4-benzoxathiin-2-yl]pyridin-2-ol

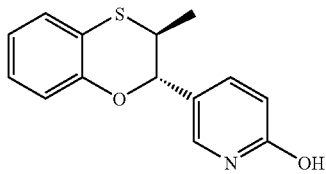

(1) Synthesis of 1-[6-(benzyloxy)pyridin-3-yl]propan-1-ol

In a nitrogen atmosphere at −78° C., 2.71 M n-BuLi/hexane solution (18.8 mL) was dropwise added to a THF solution of 2-(benzyloxy)-5-bromopyridine (12.2 g, 46.2 mmol) synthesized according to the method described in a reference (J. Org. Chem., 1995, Vol. 60, p. 1408), and stirred at −78° C. for 1 hour. At −78° C., propionaldehyde (4.3 mL) was dropwise added, and stirred at −78° C. for 30 minutes and then at room temperature for 3 hours. Aqueous saturated ammonium chloride solution was added to the reaction liquid, and extracted with ethyl acetate. The organic layer was washed with saturated saline, then dried with magnesium sulfate and concentrated. This was purified by silica gel column chromatography to obtain the intended compound (7.15 g, 64%) as a yellow oil.

$^1$HNMR (400 MHz, CDCl$_3$, δ): 0.91 (3H, t, J=7.6 Hz), 1.64-1.90 (2H, m), 4.57 (1H, t, J=6.8 Hz), 5.36 (2H, s), 6.78-6.84 (1H, m), 7.29-7.41 (3H, m), 7.43-7.48 (2H, m), 7.59-7.64 (1H, m), 8.07-8.10 (1H, m)

ESI-MS (m/e): 244.2 [M+H]$^+$ (2) Synthesis of 1-[6-(benzyloxy)pyridin-3-yl]propan-2-one Manganese dioxide (31.8 g) was added to a chloroform solution of the compound (7.1 g, 29.2 mmol) synthesized in the above (1), and stirred at 60° C. for 5 hours. The reaction liquid was filtered through Celite, and the mother liquid was concentrated to obtain the intended compound (6.27 g, 89%) as a yellow solid.

$^1$HNMR (400 MHz, CDCl$_3$, δ): 1.23 (3H, t, J=7.3 Hz), 2.95 (2H, q, J=7.3 Hz), 5.45 (2H, s), 6.82-6.87 (1H, m), 7.30-7.41 (3H, m), 7.43-7.49 (2H, m), 8.14-8.19 (1H, m), 8.78-8.82 (1H, m)

ESI-MS (m/e): 242.1 [M+H]$^+$ (3) Synthesis of 2-bromo-1-(6-hydroxypyridin-3-yl)propan-1-one Phenyltrimethylammonium tribromide (9.28 g) was added to a THF solution of the compound (5.67 g, 23.5 mmol) synthesized in the above (2), and stirred at 80° C. for 3 hours. Aqueous saturated sodium thiosulfate solution was added to the reaction liquid, and extracted three times with chloroform. After dried with magnesium sulfate, this was concentrated under reduced pressure. The obtained residue was crystallized from ethyl acetate and hexane to obtain the entitled compound (2.3 g, 42%) as a white solid.

$^1$H-NMR (400 MHz, DMSO-d$_6$, δ): 1.70 (3H, d, J=6.8 Hz), 5.66 (1H, q, J=6.5 Hz), 6.38-6.43 (1H, m), 7.86-7.91 (1H, m), 8.35-8.39 (1H, m), 12.31 (1H, brs)

(4) Synthesis of the Entitled Compound

The entitled compound was obtained according to the method of Reference Example (3), (4), (5), according to a method similar to it, and according to a combination of the method with an ordinary method, but using the compound synthesized in the above (3) and 2-mercaptopyridin-3-ol synthesized in Reference Example 5-(2) as the starting material.

$^1$HNMR (400 MHz, CDCl$_3$, δ): 1.19 (3H, d, J=6.8 Hz), 3.34-3.42 (1H, m), 4.60 (1H, d, J=8.3 Hz), 6.64-6.69 (1H, m), 6.83-6.93 (2H, m), 6.99-7.04 (1H, m), 7.05-7.09 (1H, m), 7.38-7.42 (1H, m), 7.47-7.52 (1H, m)

ESI-MS (m/e): 260.3 [M+H]$^+$

Reference Example 13

Production of 3-[(2R)-2-methylpyrrolidin-1-yl]propan-1-ol

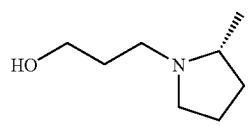

The entitled compound was obtained as a colorless oil according to the method of Reference Example 7, according to a method similar to it, and according to a combination of the method with an ordinary method, but using (2R)-2-methylpyrrolidine hydrobromide produced from L-prolinol according to the method described in a reference (J. Org. Chem., 1989, Vol. 54, p. 209).

$^1$H-NMR (400 MHz, CDCl$_3$) δ: 1.14 (3H, d, J=5.9 Hz), 1.33-1.43 (1H, m), 1.50-1.58 (1H, m), 1.66-1.77 (2H, m), 1.86-1.97 (2H, m), 2.09 (1H, q, J=8.9 Hz), 2.25-2.34 (1H, m), 2.38-2.43 (1H, m), 2.99 (1H, td, J=12.0, 3.4 Hz), 3.31-3.37 (1H, m), 3.81 (2H, dd, J=7.8, 2.4 Hz)

Reference Example 14

Synthesis of 4-[(2S*,3S*)-8-methoxy-3-methyl-2,3-dihydro-1,4-benzoxathiin-2-yl]phenol

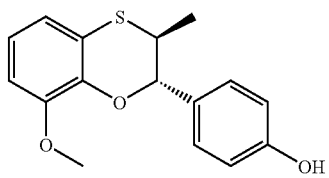

(1) Synthesis of 4-((1E)-1-{4-[(triisopropylsilyl)oxy]phenyl}prop-1-en-1-yl)morpholine Titanium tetrachloride (28 mL) and morpholine (mL) were added in that order to a toluene (1.5 L) solution of 1-{4-[(triisopropylsilyl)oxy]phenyl}propan-1-one (130 g, 0.424 mol) synthesized in Reference Example 1-2-(1), and stirred at 130° C. for 12 hours. After cooled with ice, the insoluble matter in the reaction liquid was removed by filtration through Celite, and the mother liquid was concentrated to obtain a crude product (193 g) of the intended compound.

(2) Synthesis of triisopropylsilyl {4-[(1E)-prop-1-en-1-yl]phenoxy}silane

With cooling with ice, borane/dimethyl sulfide complex (47.2 mL) was dropwise added to a THF (470 mL) solution of the crude product (193 g) of the compound obtained in the above (1) over 10 minutes. Next, this was restored to room temperature and stirred for 90 minutes. This was again cooled with ice, and methanol (58 mL) was dropwise added over 15 minutes. Next, this was restored to room temperature, and stirred for 12 hours. A sufficient amount of Celite was added to the reaction solution, and stirred for a while, and then filtered. The mother liquid was concentrated under reduced pressure, and the obtained residue was dissolved in THF (470 mL), and with cooling with ice, aqueous 30% hydrogen peroxide (59.1 g) was dropwise added over 30 minutes. Next, this was restored to room temperature and stirred for 2.5 hours. Aqueous saturated sodium sulfite solution was added to the reaction solution, stirred for a while, and the organic layer was collected. The aqueous layer was back-extracted once with ethyl acetate. The organic layers were collected, dried with magnesium sulfate, and the solvent was concentrated under reduced pressure. The obtained residue was purified by silica gel column chromatography (hexane/ethyl acetate=100/4) to obtain the intended compound (87.7 g, 64% in 2 steps).

$^1$H-NMR (CDCl$_3$): 1.09 (18H, d, J=6.8 Hz), 1.19-1.30 (3H, m), 1.84 (3H, dd, J=6.6, 1.7 Hz), 6.02-6.13 (1H, m), 6.32 (1H, dd, J=15.9, 1.7 Hz), 6.76-6.84 (2H, m), 7.15-7.21 (2H, m)

ESI-MS (m/e): 291.3 [M+H]$^+$ (3) Synthesis of (1R*,2R*)-1-{4-[(triisopropylsilyl) oxy]phenyl}propane-1,2-diol ADmix-β (by Aldrich, 241 g) and methanesulfonamide (16.4 g) were added to a mixed solvent of t-butanol (860 mL) and distilled water (860 mL), and stirred to be homogeneous at room temperature. Next, with cooling with ice, the compound obtained in the above (2) was added, and stirred for 7 hours with the inner temperature kept at from 0° C. to 5° C. Sodium sulfite (260 g) was added, then restored to room temperature, and stirred for 40 minutes. Ethyl acetate (500 mL) and water (900 mL) were added, then the organic layer was collected, and the aqueous layer was back-extracted once with ethyl acetate (750 mL). The organic layers were collected, extracted twice with aqueous 2 N potassium hydroxide solution (600 mL), then the organic layer was dried with magnesium sulfate, and the solvent was evaporated off under reduced pressure to obtain the intended compound (59.3 g, 100%).

$^1$H-NMR (CDCl$_3$): 1.00 (3H, d, J=6.3 Hz), 1.09 (18H, d, J=7.3 Hz), 3.76-3.84 (1H, m), 4.28 (1H, d, J=7.8 Hz), 6.80-6.88 (2H, m), 7.13-7.20 (2H, m)

(4) Synthesis of triisopropyl{4-[(2R*,3R*)-3-methyloxylan-2-yl]phenoxy}silane

Trimethoxyethane (28 mL) and chlorotrimethylsilane (28.3 mL) were added in that order at room temperature to a chloroform (850 mL) solution of the compound (59.3 g, 171.7 mmol) obtained in the above (3), and stirred at room temperature for 75 minutes. The reaction solvent was evaporated off under reduced pressure, the obtained residue was dissolved in methanol (1 L), then potassium carbonate (23.7 g) was added and stirred at room temperature for 4.5 hours. The insoluble matter in the reaction solution was removed by filtration, the mother liquid was concentrated under reduced pressure. The residue was dissolved in ethyl acetate (350 mL), and extracted once with distilled water (400 mL) and once with saturated saline. The organic layer was dried with magnesium sulfate, and the solvent was concentrated under reduced pressure. The obtained residue was purified by NH silica gel column chromatography (hexane 100%) to obtain the intended compound (37.1 g, 70%).

$^1$H-NMR (CDCl$_3$): 1.09 (18H, d, J=7.4 Hz), 1.18-1.30 (3H, m), 1.43 (3H, d, J=5.1 Hz), 3.01-3.07 (1H, m), 3.51 (1H, d, J=1.6 Hz), 6.82-6.87 (2H, m), 7.07-7.13 (2H, m)

ESI-MS (m/e): 307.2 [M+H]$^+$ (5) Synthesis of 2-[((1S*,2R*)-2-hydroxy-1-{4-[(triisopropylsilyl)oxy]phenyl}propyl)thio]-6-methoxyphenol N-ethyldiisopropylamine (12.9 mL) and 2-mercapto-6-methoxyphenol (9.8 g) synthesized in Reference Example 8(4) were added in that order to a methanol (180 mL) solution of the compound obtained in the above (4), and stirred at room temperature for 14 hours. The reaction solvent was evaporated off under reduced pressure, the residue was dissolved in ethyl acetate, and extracted twice with distilled water. The organic layer was dried with magnesium sulfate, and the solvent was evaporated off under reduced pressure. The obtained residue was purified by NH silica gel column chromatography (chloroform 100%) to obtain the intended compound (28.7 g, 100%).

$^1$H-NMR (CDCl$_3$): 1.02-1.16 (21H, m), 1.17-1.30 (3H, m), 3.88 (3H, s), 3.93-4.01 (1H, m), 4.03 (1H, d, J=4.9 Hz), 6.54 (1H, brs), 6.70-6.77 (1H, m), 6.78-6.87 (3H, m), 6.92-6.97 (1H, m), 7.19-7.25 (2H, m)

(6) Synthesis of triisopropyl {4-[(2S*,3S*)-8-methoxy-3-methyl-4,4-dioxido-2,3-dihydro-1,4-benzoxathiin-2-yl]phenoxy}silane Amberlyst 15 (by Aldrich, 21.6 g) was added to a toluene solution of the compound obtained in the above (5), and stirred at 45° C. for 20 hours. The insoluble matter in the reaction liquid was separated by filtration, and the mother liquid was concentrated to obtain a crude product of the intended compound.

(7) Synthesis of the Entitled Compound

The entitled compound was obtained according to the method of Reference Example 3-1, according to a Method similar to it, and according to a combination of the method with an ordinary method, but using the compound obtained in the above (6) as the starting material.

Reference Example 15

Synthesis of 3-(methoxymethoxy)pyridine-2-thiol

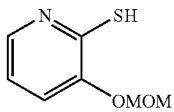

(1) Synthesis of 2,2-dithiodipyridin-3-ol

With cooling with ice, sulfuryl chloride (1.07 mL, 13.3 mmol) was added to a chloroform solution (50 mL) of the compound (3.07 g, 24.1 mmol) synthesized in Reference Example 5(2), and stirred at room temperature for 2 hours. Aqueous saturated sodium hydrogencarbonate solution was added to the reaction liquid, and filtered. The obtained solid was dried at 50° C. for 2 hours to obtain the entitled compound (2.86 g, 94%).

$^1$H-NMR (400 MHz, DMSO-$d_6$, δ): 7.15 (2H, dd, J=8.0, 4.6 Hz), 7.21 (2H, dd, J=1.5, 8.0 Hz), 7.94 (2H, dd, J=4.4, 1.5 Hz)

(2) Synthesis of 2,2'-dithiobis[3-(methoxymethoxy)pyridine]

With cooling with ice, t-BuOK (1.59 g, 14.2 mmol) was added to a DMF solution (100 mL) of the compound (1.49 g, 5.9 mmol) synthesized in the above (1), and stirred at room temperature for 30 minutes. With cooling with ice, chloromethyl methyl ether (1.12 mL, 14.8 mmol) was added, and stirred at room temperature for 14 hours. Water was added to the reaction liquid, and extracted with ethyl acetate. After washed with saturated saline, this was dried with sodium sulfate. The solvent was removed under reduced pressure, and the residue was purified by silica gel flash column chromatography (hexane/ethyl acetate=2/1) to obtain the intended compound (1.51 g, 75%).

$^1$H-NMR (400 MHz, CDCl$_3$, δ): 3.55 (6H, s), 5.29 (4H, s), 7.02 (2H, dd, J=8.3, 4.9 Hz), 7.32 (2H, dd, J=8.3, 1.5 Hz), 8.10 (2H, dd, J=4.8, 1.4 Hz)

(3) Synthesis of the Entitled Compound

Saturated sodium hydrosulfite (1 mL) was added to a THF (5 mL) solution of the compound (170 mg, 0.5 mmol) synthesized in the above (2), and stirred for 2 hours. The reaction liquid was extracted with ethyl acetate, washed with saturated saline, and dried with sodium sulfate. The solvent was removed under reduced pressure, and the residue was purified by silica gel flash column chromatography (hexane/ethyl acetate=2/1) to obtain the entitled compound (157 mg, 92%).

$^1$H-NMR (400 MHz, CDCl$_3$, δ): 3.54 (3H, s), 5.34 (2H, s), 6.74 (1H, dd, J=7.8, 6.3 Hz), 7.26 (1H, dd, J=7.3, 1.4 Hz), 7.36 (1H, dd, J=6.3, 1.5 Hz)

Reference Example 16-1

Synthesis of 4-[(2S*,3S*)-3-methyl-2,3-dihydro[1,4] oxathiino[3,2-b]pyridin-2-yl]phenol

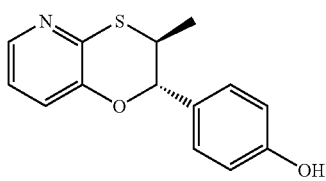

(1) Synthesis of 1-{4-[(4-methoxybenzyl)oxy]phenyl}propan-1-one

4'-Hydroxypropiophenone (50.0 g, 0.33 mol), potassium carbonate (69.0 g, 0.50 mol), and sodium iodide (25.0 g, 0.17 mol) were suspended in 2-butanone (500 mL), and with stirring at room temperature, 4-methoxybenzyl chloride (57.4 g, 0.37 mol) was added at room temperature. The reaction solution was stirred at 60° C. for 12 hours. The reaction solution was poured into water, extracted with ethyl acetate, the organic layer was washed with saturated saline, and dried with magnesium sulfate. The solvent was removed under reduced pressure, and the resulting pale yellow solid was washed with hexane to obtain the entitled compound (86.3 g, 96%) as a milky white solid.

$^1$H-NMR (400 MHz, CDCl$_3$, δ): 1.21 (3H, t, J=7.3 Hz), 2.95 (2H, q, J=7.3 Hz), 3.82 (3H, s), 5.05 (2H, s), 6.93 (2H, d, J=8.8 Hz), 7.00 (2H, d, J=8.8 Hz), 7.36 (2H, d, J=8.8 Hz), 7.95 (2H, d, J=8.8 Hz)

(2) Synthesis of t-butyl[((1Z)-1-{4-[(4-methoxybenzyl)oxy]phenyl}prop-1-en-1-yl)oxy]dimethylsilane With cooling with ice, potassium hexamethyldisilazide (0.5 M toluene solution, 89 mL) was dropwise added to a stirring THF (100 mL) solution of the compound (10.0 g, 37.0 mmol) synthesized in the above (1) and t-butyldimethylchlorosilane (6.13 g, 40.7 mmol), and then the reaction solution was stirred at room temperature for 12 hours. The reaction solution was poured into water, extracted with ethyl acetate, the organic layer was washed with saturated saline, and dried with magnesium sulfate. The solvent was removed under reduced pressure, and the residue was purified by silica gel flash column chromatography (hexane) to obtain the entitled compound (13.5 g, 95%) as a white solid.

$^1$H-NMR (400 MHz, CDCl$_3$, δ): −0.04 (6H, s), 1.02 (9H, s), 1.75 (3H, d, J=8.0 Hz), 3.86 (3H, s), 5.01 (2H, s), 5.12 (1H, q, J=8.0 Hz), 6.95 (4H, m), 7.39 (4H, m)

(3) Synthesis of (2R*)-2-hydroxy-1-{4-[(4-methoxybenzyl)oxy]phenyl}propan-1-one Ad-mix-β (28.0 g) and methanesulfonamide (1.90 g, 20 mmol) were suspended in t-butanol (100 mL) and water (100 mL), then the compound (7.7 g, 20 mmol) synthesized in the above (2) was added under stirring with cooling with ice. The reaction solution was stirred for 15 hours with cooling with ice, then sodium sulfite (20 g, 0.16 mol) was added, and further stirred at room temperature for 1 hour. The reaction solution was poured in water, extracted with chloroform, and the organic layer was washed with saturated ammonium chloride and dried with magnesium sulfate. The solvent was removed under reduced pressure, and the resulting pale yellow solid was washed with diisopropyl ether and n-heptane to obtain the entitled compound (5.1 g, 89%) as a milky white solid.

$^1$H-NMR (400 MHz, CDCl$_3$, δ): 1.45 (3H, d, J=6.8 Hz), 3.83 (3H, s), 5.07 (2H, s), 5.10 (1H, q, J=6.8 Hz), 6.94 (2H, d, J=8.8 Hz), 7.04 (2H, d, J=9.3 Hz), 7.36 (2H, d, J=8.8 Hz), 7.92 (2H, d, J=8.8 Hz)

(4) Synthesis of (1R*)-2-{4-[(4-methoxybenzyl)oxy]phenyl}-1-methyl-2-oxoethyl methanesulfonate The compound (1.53 g, 5.34 mmol) synthesized in the above (3) was dissolved in dichloromethane (15 mL), and with cooling with ice, methanesulfonyl chloride (0.62 mL, 8.0 mmol) and triethylamine (1.11 mL, 8.0 mmol) were added in that order. The reaction solution was stirred for 20 minutes with cooling with ice. The reaction solution was poured into aqueous saturated sodium hydrogencarbonate solution, and extracted with chloroform. The organic layer was washed with aqueous saturated ammonium chloride solution and water in that order, then dried with magnesium sulfate. The solvent was removed under reduced pressure, and the resulting pale yellow solid was washed with chloroform and n-hexane to obtain the entitled compound (1.8 g, 93%) as a white solid.

$^1$H-NMR (400 MHz, CDCl$_3$, δ): 1.65 (3H, d, J=8.0 Hz), 3.12 (3H, s), 3.81 (3H, s), 5.04 (2H, s), 6.00 (1H, q, J=8.0 Hz), 6.93 (2H, d, J=8.0 Hz), 7.04 (2H, d, J=8.0 Hz), 7.35 (2H, d, J=8.0 Hz), 7.93 (2H, d, J=8.0 Hz)

(5) Synthesis of (2S*)-1-{4-[(4-methoxybenzyl)oxy]phenyl}-2-{[3-(methoxymethoxy)pyridin-2-yl]thio}propan-1-one Dried cesium fluoride (5.31 g, 35.0 mmol) and 3-(methoxymethoxy)pyridine-2-thiol (6.0 g, 35.0 mmol) synthesized in Reference Example 15 were dissolved in DMF (120 mL), and under stirring with cooling with ice, (1R*)-2-{4-[(4-methoxybenzyl)oxy]phenyl}-1-methyl-2-oxoethyl methanesulfonate (11.58 g, 31.8 mmol) synthesized in the above (4) was added. The reaction solution was stirred for 20 hours with cooling with ice, then 2 N HCl (20 mL) and water (180 mL) were added, and further stirred for 20 minutes with cooling with ice. The formed solid was collected by filtration, washed with water, and dried under reduced pressure to obtain the entitled compound (13.3 g, containing 20% side product) as a milky white solid.

$^1$H-NMR (400 MHz, CDCl$_3$, δ): 1.63 (3H, d, J=7.3 Hz), 3.47 (3H, s), 3.82 (3H, s), 5.03 (2H, s), 5.20 (2H, s), 5.77 (1H, q, J=7.3 Hz), 6.99-6.91 (5H, m), 7.27-7.25 (1H, m), 7.34 (2H, d, J=8.8 Hz), 8.06 (2H, d, J=9.3 Hz), 8.08 (1H, dd, J=4.9, 1.5 Hz)

(6) Synthesis of (2S*)-1-{4-[(4-methoxybenzyl)oxy]phenyl}-2-([3-(methoxymethoxy)pyridin-2-yl]thio}propan-1-ol The compound (11.5 g, 26.2 mmol, purity 80%) synthesized in the above (5) was dissolved in THF (100 mL), and under stirring at 0° C., lithium borohydride (2 M THF solution, 15.8 mL) was dropwise added. The reaction solution was stirred for 2 hours with cooling with ice, and aqueous saturated ammonium chloride solution was added. The reaction solution was poured into water, extracted with ethyl acetate. The organic layer was washed with saturated saline, then dried with magnesium sulfate. The solvent was removed under reduced pressure to obtain a crude product of the entitled compound as a pale green foamy solid. Not further purified, this was used in the next reaction directly as such.

$^1$H-NMR (400 MHz, CDCl$_3$, δ): 1.24 (3H, d, J=8.0 Hz), 3.51 (3H, s), 3.82 (3H, s), 3.99 (1H, m), 4.60 (1H, d, J=8.0 Hz), 4.99 (2H, s), 5.25 (2H, s), 6.97-6.91 (4H, m), 7.04 (1H, m), 7.39-7.32 (5H, m), 8.11 (1H, brd, J=4.0 Hz)

(7) Synthesis of the Entitled Compound

The compound synthesized in the above (6) was mixed with anisole (8.52 mL, 78.8 mmol) and trifluoroacetic acid (20 mL, 0.26 mol) under cooling with ice, and stirred for 15 minutes under cooling with ice. Aqueous saturated sodium hydrogencarbonate solution was added, then the reaction solution was extracted with ethyl acetate. The organic layer was washed with aqueous saturated sodium hydrogencarbonate solution, water and saturated saline in that order, and dried with magnesium sulfate. The solvent was removed under reduced pressure, and the residue was purified by silica gel flash column chromatography (hexane/ethyl acetate=1/1), and further recrystallized (ethyl acetate/n-heptane) to obtain the entitled compound (1.9 g, 35% in 2 steps) as a white solid.

$^1$H-NMR (400 MHz, DMSO-d$_6$, δ): 1.02 (3H, d, J=6.8 Hz), 3.80-3.73 (1H, m), 4.77 (1H, d, J=8.8 Hz), 6.79 (2H, d, J=8.3 Hz), 7.05 (1H, dd, J=8.3, 4.4 Hz), 7.23-7.21 (1H, m), 7.24 (2H, d, J=8.8 Hz), 8.04 (1H, dd, J=4.4, 1.5 Hz), 9.59 (1H, s)

Reference Example 16-2

Synthesis of 4-[(2R*,3R*)-3-methyl-2,3-dihydro[1,4]oxathiino[3,2-b]pyridin-2-yl]phenol

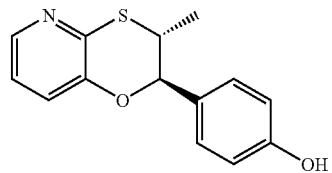

The entitled compound was obtained according to the method of Reference Example 16-1, according to a method similar to it, and according to a combination of the method with an ordinary method, but using ADmix-α (by Aldrich) in place of ADmix-β (by Aldrich) in the synthesis in Reference Example 16-1-(3) and using 4'-hydroxypropiophenone as the starting material.

Reference Example 17

Synthesis of 2-bromo-4-[(2S*,3S*)-8-methoxy-3-methyl-4,4-dioxido-2,3-dihydro-1,4-benzoxathiin-2-yl]phenol

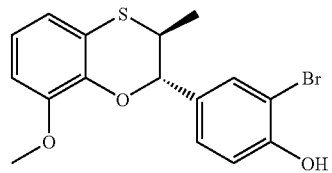

4-[(2S*,3S*)-8-methoxy-3-methyl-2,3-dihydro-1,4-benzoxathiin-2-yl]phenol synthesized in Reference Example 14 was dissolved in a mixed solvent of methanol (12 mL) and chloroform (6 mL), and with cooling with ice, a methanol (6 mL) solution of phenyltrimethylammonium tribromide (304 mg) was dropwise added over 5 minutes, and thereafter with cooling with ice, this was stirred for 1.5 hours. Aqueous saturated sodium thiosulfate solution (4 mL) and aqueous saturated sodium hydrogencarbonate solution (4 mL) were added, and then immediately back-extracted twice with chloroform. The organic layer was collected, washed with saturated saline, dried with magnesium sulfate, and the solvent was evaporated off under reduced pressure. The obtained residue was purified by reversed-phase HPLC (0.1% TFA acetonitrile/H$_2$O=10% to 95%, gradient) to obtain the entitled compound (146 mg, 52%) as a white solid.

$^1$H-NMR (400 MHz, CDCl$_3$, δ) δ: 1.13 (3H, d, J=6.8 Hz), 3.42-3.51 (1H, m), 3.80 (3H, s), 4.64 (1H, d, J=8.3 Hz), 5.29 (1H, s), 6.54-6.59 (1H, m), 6.73-6.79 (2H, m), 7.09-7.13 (1H, m), 7.14-7.19 (2H, m)

ESI-MS (m/e): 367.0 [M+H]$^+$

Reference Example 18-1

Synthesis of 2-bromo-4-[(2S*,3S*)-3-methyl-2,3-dihydro[1,4]oxathiino[3,2-b]pyridin-2-yl]phenol

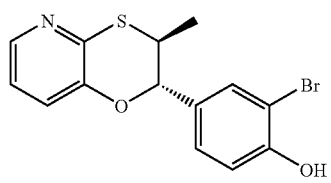

The entitled compound was obtained according to the method of Reference Example 17, according to a method similar to it, and according to a combination of the method with an ordinary method, but using 4-[(2S*,3S*)-3-methyl-2,3-dihydro[1,4]oxathiino[3,2-b]pyridin-2-yl]phenol synthesized in Reference Example 16-1 as the starting material.

$^1$H-NMR (400 MHz, DMSO-d$_6$, δ) δ: 3.74-3.84 (1H, m), 4.82 (1H, d, J=8.3 Hz), 6.93-6.99 (1H, m), 7.02-7.07 (1H, m), 7.19-7.28 (2H, m), 7.54-7.59 (1H, m), 8.00-8.05 (1H, m), 10.46 (1H, brs)

ESI-MS (m/e): 377.9 [M+H]$^+$

Reference Example 18-2

Synthesis of 2-bromo-4-[(2R*,3R*)-3-methyl-2,3-dihydro[1,4]oxathiino[3,2-b]pyridin-2-yl]phenol

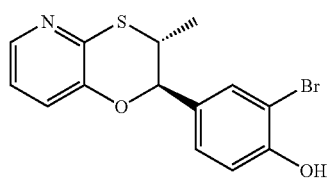

The entitled compound was obtained according to the method of Reference Example 17, according to a method similar to it, and according to a combination of the method with an ordinary method, but using 4-[(2R*,3R*)-3-methyl-2,3-dihydro[1,4]oxathiino[3,2-b]pyridin-2-yl]phenol synthesized in Reference Example 16-2 as the starting material.

Reference Example 19

Synthesis of 2-mercapto-4-methoxyphenol

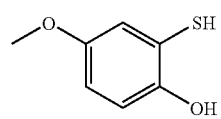

(1) Synthesis of 5-methoxy-1,3-benzoxathiol-2-one

With cooling with ice, 60% oily sodium hydride (3.14 g) was added to a 1,2-dimethoxyethane (100 mL) solution of 5-hydroxy-1,3-benzoxathiol-2-one (10 g, 59.5 mmol), and stirred for 10 minutes. With cooling with ice, methyl iodide (37 mL) was added to the reaction liquid, and stirred for 2 hours with cooling with ice and further for 6 hours at room temperature. Aqueous saturated ammonium chloride solution was added to the reaction liquid, and extracted three times with chloroform. The organic layer was dried with magnesium sulfate, and concentrated under reduced pressure. The obtained residue was purified by silica gel column chromatography (hexane/ethyl acetate=3/2) to obtain the intended compound (7.8 g, 72%) as a white solid.

5-Hydroxy-1,3-benzoxathiol-2-one was synthesized according to the method described in a reference (J. Org. Chem., 1968, Vol. 33, p. 4426.

$^1$HNMR (400 MHz, CDCl$_3$, δ): 3.82 (3H, s), 6.83-6.87 (1H, m), 6.92-6.94 (1H, m), 7.17-7.21 (1H, m)

(2) Synthesis of the Entitled Compound

Aqueous 2 N sodium hydroxide solution (44.7 mL) was added to an ethanol solution of the compound (7.76 g, 42.6 mmol) synthesized in the above (1), and stirred in a nitrogen atmosphere at 65° C. for 1.5 hours. The reaction liquid was neutralized with aqueous 5 N hydrochloric acid solution, and extracted twice with chloroform. The organic layer was dried with magnesium sulfate, and concentrated under reduced pressure to obtain the entitled compound (7.4 g, 100%) as a yellow oil.

$^1$HNMR (400 MHz, CDCl$_3$, δ): 3.12 (1H, s), 3.75 (3H, s), 5.74 (1H, brs), 6.76-6.80 (1H, m), 6.85-6.89 (1H, m), 6.97-7.00 (1H, m)

Reference Example 20

Synthesis of 2-mercapto-5-methoxyphenol

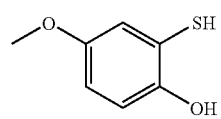

The entitled compound was obtained according to the method of Reference Example 11, according to a method similar to it, and according to a combination of the method with an ordinary method, but using 6-hydroxy-1,3-benzoxathiol-2-one as the starting material.

$^1$HNMR (400 MHz, CDCl$_3$, δ): 2.80-2.82 (1H, m), 3.77 (3H, s), 6.39-6.47 (2H, m), 6.53-6.56 (1H, m), 7.34-7.38 (1H, m)

Pharmacological test examples are shown below in which (2S*,3S*)-2,3-dihydro-3-methyl-2-[4-[3-(1-pyrrolidinyl)propoxy]phenyl]-1,4-benzoxathiin-4,4-dioxide synthesized in Example 27 was used as the test compound.

Pharmacological Test Example 1

Histamine Analogue-Binding Inhibition Test

A cDNA sequence coding for a human histamine-H3 receptor [see WO00/39164] was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see Proceedings of the National Academy of Sciences of the United States of America, Vol., 84, p. 7413 (1987)] to obtain histamine-H3 receptor expression cells.

A membrane specimen prepared from the cells having expressed a histamine-H3 receptor was incubated in an assay buffer (50 mM Tris buffer, pH 7.4) along with the test compound and 20,000 cpm [$^3$H]N-α-methylhistamine (by NEN) therein, at 25° C. for 2 hours, and then filtered through a glass filter GF/C. After washed with 50 mM Tris buffer (pH 7.4), the radioactivity on the glass filter was determined. The nonspecific binding was determined in the presence of 10 μM thioperamide (by Sigma), and the 50% inhibitory concentration ($IC_{50}$) of the test compound to the specific N-alpha-methylhistamine binding was calculated [Molecular Pharmacology, Vol. 55, p. 1101 (1999)]. As a result, $IC_{50}$ of (2S*,3S*)-2,3-dihydro-3-methyl-2-[4-[3-(1-pyrrolidinyl)propoxy]phenyl]-1,4-benzoxathiin-4,4-dioxide was 0.35 nM.

As in the above, the compound of the invention strongly inhibited the binding of N-alpha-methylhistamine (histamine analogue) to histamine-H3 receptor.

Pharmacological Test Example 2

Test for Antagonistic Effect to Water-Drinking Action Induced by Histamine-H3 Receptor Selective Agonist, R-α-Methylhistamine Under anesthesia with ketamine xylazine (74 and 11 mg/kg intraabdominal single administration), a brain stereotaxic device was set in the third ventricle of a male DS rat (7 to 10-week age, 200 to 300 g), and a chronic guide cannula (26 gauge, length 11 mm) was inserted into it and fixed with a dental resin. The position of the tip of the guide cannula is at 2.2 mm after the bregma on the midline, and at a depth of 8 mm from the surface of the skull. After a restoration term of about 1 week, R-α-methylhistamine (0.3 μg/1 μL/head, 30% propylene glycol liquid) was administered into the third ventricle. The test compound suspended in an aqueous 0.5% methyl cellulose solution was orally administered to the rat before 2 hours before the R-α-methylhistamine administration; and after the R-α-methylhistamine administration, the amount of water drunk by the rat for 1 hour was measured. As a result, (2S*,3S*)-2,3-dihydro-3-methyl-2-[4-[3-(1-pyrrolidinyl)propoxy]phenyl]-1,4-benzoxathiin-4,4-dioxide at a dose of 10 mg/kg significantly inhibited the increase in the water drinking induced by the administration of R-α-methylhistamine in the third ventricle of the rat.

Pharmacological Test Example 3

Test for Brain/Cerebrospinal Fluid Transition

The test compound was orally or intravenously administered to an SD male rat (7 to 10-week age, 200 to 400 g), and under anesthesia with ether for a predetermined period of time, the whole blood was collected from it through the abdominal aorta thereof using a heparin-processed syringe. Next, the head skin was cut, and a dental 30 G needle was stuck into the cervical spine to run through the subarachnoid cavity. Via a tube connected to the dental 30 G needle, from 50 to 100 μL of the cerebrospinal fluid was collected in a 1-mL syringe, and then the brain was taken out. The blood sample was centrifuged (4° C., 6000 revolutions, 10 minutes), and the resulting plasma was stirred with ethanol (containing an internal standard substance) in an amount of three times thereof added to it. The brain sample was homogenized with 2 mL of water added thereto; and a part of it was taken out and stirred with ethanol (containing an internal standard substance) in an amount of three times thereof added to it. The cerebrospinal fluid was stirred with ethanol (containing an internal standard substance) in an amount of three times thereof added to it. The above samples were left at −20° C. for 20 minutes, then centrifuged (4° C., 12,000 g, 10 minutes), and the supernatant was analyzed through LC/MS/MS. According to a relative calibration curve method, the compound concentration in the plasma, in the brain and in the cerebrospinal fluid was determined. As a result, the concentration of (2S*,3S*)-2,3-dihydro-3-methyl-2-[4-[3-(1-pyrrolidinyl)propoxy]phenyl]-1,4-benzoxathiin-4,4-dioxide in the brain was 6.96 nmol/g, that in the cerebrospinal fluid was 0.174 μM and that in the plasma was 0.98 μM, after 2 hours after the oral administration (10 mg/kg).

INDUSTRIAL APPLICABILITY

The invention provides a noble substance that acts as a histamine-H3 receptor antagonist or inverse-agonist. Specifically, the benzoxathiin derivative of the formula (I) or the pharmaceutically-acceptable salt thereof has a strong histamine-H3 receptor antagonistic effect or inverse-agonistic effect, and is therefore useful for prevention or treatment for metabolic system diseases such as obesity, diabetes, hormone secretion disorder, hyperlipemia, gout and fatty liver, for circulatory system diseases such as stenocardia, acute/congestive cardiac insufficiency, cardiac infarction, coronary arteriosclerosis, hypertension, nephropathy and electrolyte disorder, for central and peripheral nervous system diseases such as sleep disorder, various diseases accompanied by sleep disorder (for example, idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression anxiety, schizophrenia), bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism, tremor, et al.

The invention claimed is:
1. A compound of the formula (I):

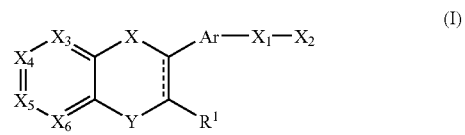

wherein:
R$^1$ represents methyl or ethyl;
R$^2$ each independently represents a hydrogen atom, a lower alkyl group (wherein the lower alkyl group may be substituted with a halogen atom), a lower alkoxy group (wherein the lower alkoxy group may be substituted with a halogen atom), or a halogen atom;

X is an oxygen atom;
Y is a sulfanyl group, a sulfinyl group or a sulfonyl group;
Ar represents a divalent group derived from a benzene ring, a pyridine ring, a pyrimidine ring, a pyrazine ring or a pyridazine ring by removing two hydrogen atoms therefrom (wherein the divalent group may be substituted with a halogen atom, a hydroxyl group, a lower alkoxy group, wherein the lower alkoxy group may be substituted with a halogen atom, a lower alkyl group, wherein the lower alkyl group may be substituted with a halogen atom);
$X_1$ represents a carbon atom, a nitrogen atom, a sulfur atom or an oxygen atom;
$X_2$ represents a group of a formula (III):

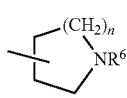

(III)

wherein the point of attachment of group of the formula (III) is other than through the nitrogen atom, and wherein $R^6$ represents a lower alkyl group (wherein the lower alkyl group may be substituted with a halogen atom), or a cycloalkyl group (wherein the cycloalkyl group may be substituted with a lower alkyl group or a halogen atom), n indicates from 0 to 4, $X_3$ to $X_6$ each independently represent —$CR^2$— or a nitrogen atom, n indicates from 0 to 4; however, not more than one of $X_3$ to $X_6$ is a nitrogen atom;
the formula (V):

(V)

indicates a single bond or a double bond;
or a pharmaceutically acceptable salt thereof.

2. The compound of claim 1, wherein $R^2$ each independently represents a hydrogen atom, or a lower alkyl group (wherein the lower alkyl group may be substituted with a halogen atom).

3. A compound of the formula (I-1):

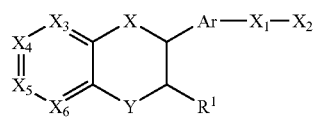

(I-1)

wherein:
$R^1$ represents methyl or ethyl;
$R^2$ each independently represents a hydrogen atom, a lower alkyl group (wherein the lower alkyl group may be substituted with a halogen atom), a lower alkoxy group (wherein the lower alkoxy group may be substituted with a halogen atom), or a halogen atom;
X is an oxygen atom;
Y is a sulfanyl group, a sulfinyl group or a sulfonyl group;
Ar represents a divalent group derived from a benzene ring, a pyridine ring, a pyrimidine ring, a pyrazine ring or a pyridazine ring by removing two hydrogen atoms therefrom (wherein the divalent group may be substituted with a halogen atom, a lower alkoxy group (wherein the lower alkoxy group may be substituted with a halogen atom), a lower alkyl group (wherein the lower alkyl group may be substituted with a halogen atom), or a hydroxyl group);
$X_1$ represents a carbon atom, a nitrogen atom, a sulfur atom or an oxygen atom;
$X_2$ represents a group of a formula (III):

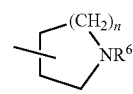

(III)

wherein the point of attachment of group of the formula (III) is other than through the nitrogen atom, and wherein $R^6$ represents a lower alkyl group (wherein the lower alkyl group may be substituted with a halogen atom), or a cycloalkyl group (wherein the cycloalkyl group may be substituted with a lower alkyl group or a halogen atom), n indicates from 0 to 4, $X_3$ to $X_6$ each independently represent —$CR^2$— or a nitrogen atom; however, 3 or more of $X_3$ to $X_6$ are not nitrogen atoms at the same time;
or a pharmaceutically acceptable salt thereof.

4. The compound of claim 3, wherein each of $X_3$ to $X_6$ are —$CR^2$—.

5. The compound of claim 3, wherein one of $X_3$ to $X_6$ is a nitrogen atom, and the remaining three are —$CR^2$—.

6. The compound of claim 3, wherein $R^6$ is a lower alkyl group or a cycloalkyl group, and n is 1 or 2.

7. The compound of claim 3, wherein X is an oxygen atom and Y is a sulfanyl group.

8. The compound of claim 3, wherein X is an oxygen atom and Y is a sulfonyl group.

9. A compound which is selected from the group consisting of:

(2,3-trans)-2,3-dihydro-3-ethyl-2-[4-[(1-cyclobutylpiperidin-4-yl)oxy]phenyl]-1,4-benzoxathiin, (2,3-trans)-2,3-dihydro-3-ethyl-2-[4-[(1-cyclobutylpiperidin-4-yl)oxy]phenyl]-1,4-benzoxathiin-4,4-dioxide, (2,3-trans)-2,3-dihydro-3-methyl-2-[4-[(1-cyclobutylpiperidin-4-yl)oxy]phenyl]-1,4-benzoxathiin-4,4-dioxide, (2,3-trans)-2,3-dihydro-8-methoxy-3-methyl-2-[4-[(1-cyclobutylpiperidin-4-yl)oxy]phenyl]-1,4-benzoxathiin-4,4-dioxide, (2S,3S)-2,3-dihydro-8-methoxy-3-methyl-2-[4-[(1-cyclobutylpiperidin-4-yl)oxy]phenyl]-1,4-benzoxathiin-4,4-dioxide, (2R,3R)-2,3-dihydro-8-methoxy-3-methyl-2-[4-[(1-cyclobutylpiperidin-4-yl)oxy]phenyl]-1,4-benzoxathiin-4,4-dioxide, (2,3-trans)-2,3-dihydro-5-methoxy-3-methyl-2-[4-[(1-cyclobutylpiperidin-4-yl)oxy]phenyl]-1,4-benzoxathiin-4,4-dioxide, (2S,3S)-2,3-dihydro-5-methoxy-3-methyl-2-[4-[(1-cyclobutylpiperidin-4-yl)oxy]phenyl]-1,4-benzoxathiin-4,4-dioxide, (2R,3R)-2,3-dihydro-5-methoxy-3-methyl-2-[4-[(1-cyclobutylpiperidin-4-yl)oxy]phenyl]-1,4-benzoxathiin-4,4-dioxide, (2R,3R)-2-{4-[(1-cyclobutylpiperidin-4-yl)oxy]phenyl}-3-methyl-2,3-dihydro[1,4]oxathiino[3,2-b]pyridine 4,4-dioxide, (2S,3S)-2-{4-[(1-cyclobutylpiperidin-4-yl)oxy]phenyl}-3-methyl-2,3-dihydro[1,4]oxathiino[3,2-b]pyridine 4,4-dioxide, (2S,3S)-2-{4-[(1-isopropylpiperidin-4-yl)oxy]phenyl}-3-methyl-2,3-dihydro[1,4]oxathiino[3,2-b]pyridine 4,4-dioxide, (2R,3R)-2-{4-[(1-isopropylpiperidin-4-yl)oxy]phenyl}-3-methyl-2,3-dihydro[1,4]oxathiino[3,2-b]pyridine 4,4-dioxide, or a pharmaceutically acceptable salt thereof.

10. The compound of claim 9 which is selected from the group consisting of:

(2R,3R)-2,3-dihydro-8-methoxy-3-methyl-2-[4-[(1-cyclobutylpiperidin-4-yl)oxy]phenyl]-1,4-benzoxathiin-4,4-dioxide; and (2S,3S)-2,3-dihydro-8-methoxy-3-methyl-2-[4-[(1-cyclobutylpiperidin-4-yl)oxy]phenyl]-1,4-benzoxathiin-4,4-dioxide;

or a pharmaceutically acceptable salt thereof.

11. The compound of claim 9 which is selected from the group consisting of:

(2R,3R)-2-{4-[(1-cyclobutylpiperidin-4-yl)oxy]phenyl}-3-methyl-2,3-dihydro[1,4]oxathiino[3,2-b]pyridine 4,4-dioxide; and (2S,3S)-2-{4-[(1-cyclobutylpiperidin-4-yl)oxy]phenyl}-3-methyl-2,3-dihydro[1,4]oxathiino[3,2-b]pyridine 4,4-dioxide;

or a pharmaceutically acceptable salt thereof.

12. A pharmaceutical composition which comprises a pharmaceutically acceptable additive and the compound of claim 1 or a pharmaceutical acceptable salt.

13. A pharmaceutical composition which comprises a pharmaceutically acceptable additive and the compound of claim 9 or a pharmaceutical acceptable salt.

\* \* \* \* \*